US009193936B2

(12) United States Patent
Allen et al.

(10) Patent No.: US 9,193,936 B2
(45) Date of Patent: *Nov. 24, 2015

(54) QUATERNIZED FATTY AMINES, AMIDOAMINES AND THEIR DERIVATIVES FROM NATURAL OIL METATHESIS

(75) Inventors: Dave R. Allen, Chicago, IL (US); Marcos Alonso, Chicago, IL (US); Randal J. Bernhardt, Antioch, IL (US); Aaron Brown, Chicago, IL (US); Sangeeta Ganguly-Mink, Chicago, IL (US); Andrew D. Malec, Chicago, IL (US); Teresa Manuel, West Chester, OH (US); Ronald A. Masters, Glenview, IL (US); Lawrence A. Munie, Grayslake, IL (US); Dennis S. Murphy, Libertyville, IL (US); Patti Skelton, Winder, GA (US); Brian Sook, Lawrenceville, GA (US); Michael R. Terry, Gurnee, IL (US); Jeremy Aaron Weitgenant, Grayslake, IL (US); Laura Lee Whitlock, Highland Park, IL (US); Michael Wiester, Chicago, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/879,786

(22) PCT Filed: Oct. 25, 2011

(86) PCT No.: PCT/US2011/057605
§ 371 (c)(1),
(2), (4) Date: May 15, 2013

(87) PCT Pub. No.: WO2012/061098
PCT Pub. Date: May 10, 2012

(65) Prior Publication Data
US 2013/0225409 A1  Aug. 29, 2013

Related U.S. Application Data

(60) Provisional application No. 61/406,547, filed on Oct. 25, 2010, provisional application No. 61/406,556, filed on Oct. 25, 2010, provisional application No. 61/406,570, filed on Oct. 25, 2010.

(51) Int. Cl.
*C11C 3/08* (2006.01)
*C07C 69/533* (2006.01)
(Continued)

(52) U.S. Cl.
CPC . *C11C 3/08* (2013.01); *A01N 25/02* (2013.01); *A01N 25/04* (2013.01); *A01N 25/30* (2013.01);
(Continued)

(58) Field of Classification Search
CPC .. C07C 209/16; C07C 209/28; C07C 209/64; C07C 211/63; C07C 237/16; C07C 303/32; C07C 309/17; C07C 313/02; C07C 209/12; C07C 211/21; C07C 219/08; C07C 219/12; C07C 231/12; C07C 303/18; A61N 25/02; A61N 25/30; A61N 33/04; A61N 33/12; A61N 37/02; A61N 37/18; A01N 25/02; A01N 25/04; A01N 25/30; A01N 33/04; A01N 33/12; A01N 37/02; A01N 37/18; A01N 37/44; A01N 41/04; C08K 5/01; C08K 5/20
USPC .......... 504/345, 319, 326; 560/155, 183, 186, 560/187, 205; 562/512, 553, 561, 564, 591; 564/281, 291, 296, 463, 468, 489, 509, 564/511
See application file for complete search history.

(56) References Cited

U.S. PATENT DOCUMENTS 2,653,970 A * 9/1953 Fessler .......................... 562/122
2,865,968 A  5/1955 Hansley et al.
(Continued)

FOREIGN PATENT DOCUMENTS

WO  WO-2008048522  4/2008

OTHER PUBLICATIONS

M.B. Smith et al., "March's Advanced Organic Chemistry", 2001, Wiley Interscience, John Wiley & Sons; 5th Ed., pp. 1549-1550.*
(Continued)

*Primary Examiner* — Jane C Oswecki
(74) *Attorney, Agent, or Firm* — Dilworth IP LLC

(57) ABSTRACT

Quaternary ammonium, betaine, or sulfobetaine compositions derived from fatty amines, wherein the fatty amine is made by reducing the amide reaction product of a metathesis-derived $C_{10}$-$C_{17}$ monounsaturated acid, octadecene-1,18-dioic acid, or their ester derivatives and a secondary amine, are disclosed. Quaternary ammonium, betaine, or sulfobetaine compositions derived from fatty amidoamines, wherein the amidoamine is made by reacting of a metathesis-derived $C_{10}$-$C_{17}$ monounsaturated acid, octadecene-1,18-dioic acid, or their ester derivatives and an aminoalkyl-substituted tertiary amine, are also disclosed. The quaternized compositions are advantageously sulfonated or sulfated. In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin. The quaternary ammonium, betaine, and sulfobetaine compositions and their sulfonated or sulfated derivatives are valuable for a wide variety of end uses, including cleaners, fabric treatment, hair conditioning, personal care (liquid cleansing products, conditioning bars, oral care products), antimicrobial compositions, agricultural uses, and oil field applications.

12 Claims, No Drawings

(51) Int. Cl.

| | |
|---|---|
| C07C 69/593 | (2006.01) |
| C11D 1/28 | (2006.01) |
| C11D 1/74 | (2006.01) |
| C07C 211/21 | (2006.01) |
| C07C 237/16 | (2006.01) |
| C08K 5/01 | (2006.01) |
| C08K 5/20 | (2006.01) |
| A01N 25/30 | (2006.01) |
| A01N 25/04 | (2006.01) |
| A01N 33/12 | (2006.01) |
| A01N 41/04 | (2006.01) |
| A01N 37/18 | (2006.01) |
| C07C 67/26 | (2006.01) |
| C07C 41/03 | (2006.01) |
| C07C 43/11 | (2006.01) |
| C07C 6/04 | (2006.01) |
| B01F 17/00 | (2006.01) |
| C11D 1/83 | (2006.01) |
| C11D 1/94 | (2006.01) |
| A01N 37/44 | (2006.01) |
| A61K 8/41 | (2006.01) |
| A61K 8/42 | (2006.01) |
| A61K 8/44 | (2006.01) |
| A61K 8/46 | (2006.01) |
| A61Q 5/12 | (2006.01) |
| A61Q 19/10 | (2006.01) |
| A62D 1/02 | (2006.01) |
| C11D 1/62 | (2006.01) |
| C11D 1/92 | (2006.01) |
| C11D 1/04 | (2006.01) |
| A01N 25/02 | (2006.01) |
| A61K 8/92 | (2006.01) |
| C11C 3/00 | (2006.01) |
| C11D 3/48 | (2006.01) |
| C07C 219/08 | (2006.01) |
| C07C 209/12 | (2006.01) |
| C07C 231/12 | (2006.01) |
| C07C 303/18 | (2006.01) |
| C11D 1/00 | (2006.01) |
| C08G 65/26 | (2006.01) |
| C09K 8/00 | (2006.01) |
| C09K 15/28 | (2006.01) |
| C11D 1/90 | (2006.01) |
| C11D 1/65 | (2006.01) |

(52) U.S. Cl.
CPC ............... *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 6/04* (2013.01); *C07C 41/03* (2013.01); *C07C 43/11* (2013.01); *C07C 67/26* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01); *C08K 5/20* (2013.01); *C11C 3/00* (2013.01); *C11D 1/002* (2013.01); *C11D 1/04* (2013.01); *C11D 1/28* (2013.01); *C11D 1/62* (2013.01); *C11D 1/74* (2013.01); *C11D 1/83* (2013.01); *C11D 1/92* (2013.01); *C11D 1/94* (2013.01); *C11D 3/48* (2013.01); *C09K 8/00* (2013.01); *C09K 15/28* (2013.01); *C11D 1/652* (2013.01); *C11D 1/90* (2013.01)

(56) References Cited

U.S. PATENT DOCUMENTS

| | | | |
|---|---|---|---|
| 3,169,142 A | | 2/1965 | Knaggs et al. |
| 3,193,586 A | | 7/1965 | Rittmeister et al. |
| 3,280,179 A | | 10/1966 | Ernst |
| 3,354,213 A | | 11/1967 | Miller, Jr. et al. |
| 3,497,555 A | | 2/1970 | Dudzinski et al. |
| 3,544,613 A | | 12/1970 | Knaggs et al. |
| 3,664,961 A | | 5/1972 | Norris |
| 4,087,457 A | | 5/1978 | Convers et al. |
| 4,148,821 A | | 4/1979 | Nussbaum et al. |
| 4,275,013 A | | 6/1981 | Tokosh et al. |
| 4,370,272 A | | 1/1983 | Wechsler et al. |
| 4,409,399 A | | 10/1983 | Swift et al. |
| 4,545,941 A | * | 10/1985 | Rosenburg ............... 554/163 |
| 4,594,455 A | | 6/1986 | Dudzinski |
| 4,743,660 A | | 5/1988 | Danner et al. |
| 4,744,977 A | | 5/1988 | Hensen et al. |
| 4,758,376 A | | 7/1988 | Hirota et al. |
| 4,796,702 A | | 1/1989 | Scherubel |
| 4,900,359 A | | 2/1990 | Gelbman |
| 4,913,841 A | | 4/1990 | Zeman |
| 4,994,622 A | | 2/1991 | Fong et al. |
| 5,124,491 A | | 6/1992 | Fleckenstein et al. |
| 5,211,883 A | | 5/1993 | Yamashina et al. |
| 5,482,908 A | | 1/1996 | Le-khac |
| 5,538,937 A | * | 7/1996 | Hasebe et al. ............ 504/358 |
| 5,556,615 A | | 9/1996 | Janchitraponvej et al. |
| 5,562,849 A | | 10/1996 | Wahl et al. |
| 5,574,179 A | | 11/1996 | Wahl et al. |
| 5,679,150 A | | 10/1997 | Kerkar et al. |
| 5,696,294 A | | 12/1997 | Abe et al. |
| 5,840,985 A | * | 11/1998 | Nepras et al. ............ 564/488 |
| 6,004,913 A | | 12/1999 | Iacobucci et al. |
| 6,010,991 A | | 1/2000 | Dabestani |
| 6,071,867 A | | 6/2000 | Purcell et al. |
| 6,239,093 B1 | | 5/2001 | Foley et al. |
| 6,268,324 B1 | | 7/2001 | Besse et al. |
| 6,322,778 B1 | | 11/2001 | Parr |
| 6,326,335 B1 | | 12/2001 | Kowalski et al. |
| 6,475,953 B1 | | 11/2002 | Ward et al. |
| 6,683,224 B1 | | 1/2004 | Hourticolon et al. |
| 6,821,943 B2 | | 11/2004 | Avery et al. |
| 6,919,074 B2 | | 7/2005 | Milbradt et al. |
| 7,074,395 B2 | | 7/2006 | Milbradt et al. |
| 7,208,643 B2 | | 4/2007 | Namba et al. |
| 7,244,698 B2 | | 7/2007 | Treybig et al. |
| 7,407,916 B2 | | 8/2008 | Chatterji et al. |
| 7,422,064 B1 | | 9/2008 | Yang |
| 7,449,435 B2 | | 11/2008 | Otterson et al. |
| 7,517,842 B2 | | 4/2009 | Barnhart et al. |
| 7,534,816 B2 | | 5/2009 | Koshti et al. |
| 7,576,227 B2 | | 8/2009 | Bicerano et al. |
| 7,618,926 B1 | | 11/2009 | Pakulski |
| 7,776,798 B2 | | 8/2010 | Subramanian et al. |
| 7,807,614 B2 | | 10/2010 | Llosas et al. |
| 7,951,762 B2 | | 5/2011 | Dol et al. |
| 7,960,599 B2 | | 6/2011 | Millis et al. |
| 8,067,610 B2 | | 11/2011 | Schrodi |
| 2004/0071653 A1 | | 4/2004 | Bratescu et al. |
| 2007/0010680 A1 | | 1/2007 | Yajima et al. |
| 2008/0033026 A1 | | 2/2008 | Zullo et al. |
| 2009/0188055 A1 | | 7/2009 | Bernhardt et al. |
| 2009/0264672 A1 | * | 10/2009 | Abraham et al. ............ 560/190 |
| 2009/0318294 A1 | | 12/2009 | Malec et al. |
| 2010/0016163 A1 | | 1/2010 | Keiper et al. |
| 2010/0120658 A1 | | 5/2010 | Schiedel et al. |
| 2010/0145086 A1 | | 6/2010 | Schrodi et al. |
| 2010/0282467 A1 | | 11/2010 | Hutchison et al. |
| 2011/0015071 A1 | | 1/2011 | Kisenwether et al. |

(56) References Cited

U.S. PATENT DOCUMENTS

| | | | |
|---|---|---|---|
| 2011/0113679 A1 | 5/2011 | Cohen et al. | |
| 2011/0210028 A1 | 9/2011 | Zhu | |
| 2011/0313180 A1 | 12/2011 | Uptain et al. | |
| 2012/0071676 A1 | 3/2012 | Schrodi et al. | |
| 2012/0157313 A1 | 6/2012 | Zhu et al. | |
| 2012/0197031 A1 | 8/2012 | Firth et al. | |
| 2012/0279715 A1 | 11/2012 | Nguyen et al. | |
| 2013/0035502 A1 | 2/2013 | Cohen et al. | |
| 2013/0035532 A1 | 2/2013 | Schrodi et al. | |
| 2013/0225408 A1* | 8/2013 | Allen et al. | 504/206 |
| 2013/0225473 A1* | 8/2013 | Allen et al. | 510/495 |

OTHER PUBLICATIONS

Fatty Amines, Kirk-Othmer Encyclopedia of Chemical Technology [online], [retrieved Dec. 4, 2014] Retrieved from the Internet: <URL: http://onlinelibrary.wiley.com/doi/10.1002/0471238961.0601202022091905.a01.pub2/abstract.*

Amidoamine, Wikipedia [online], [retrieved Dec. 4, 2014] Retrieved from the Internet: <URL: http://en.wikipedia.org/wiki/Amidoamine.*

J. Barrault, Catal. Today 37 (1997) 137.

S. Coan et al., J. Am. Chem. Soc. 77 (1955) 2402.

A. Blomquist et al., J. Am. Chem. Soc. 81 (1959) 678.

M. Olomucki, Doctoral Thesis, U. of Paris (1957) (in French).

Tetrahedron 68 2012, 1117.

Appl. Catal.A. 346 2009, 158.

J.C. Mol., Topics in Catalysis 27 2004, 97.

J. C. Mol., Green Chem., 4 2002, 5.

Smith, M.B. et al., "March's Advanced Organic Chemistry", 5th ed. 1541 2001, 1549-1550.

Org. Synth., Coll. vol. IV (1963) 635.

Larock, "Comprehensive Organic Transformations", 1989, 432-434.

* cited by examiner

US 9,193,936 B2

QUATERNIZED FATTY AMINES, AMIDOAMINES AND THEIR DERIVATIVES FROM NATURAL OIL METATHESIS

FIELD OF THE INVENTION

The invention relates to quaternized fatty amines, amidoamines, and derivative compositions that originate from natural resources, particularly natural oils and their metathesis products.

BACKGROUND OF THE INVENTION

"Fatty amines" generally have a nonpolar chain of six or more carbons, typically 6-30 carbons, and at least one polar end group comprising or derived from an amine, for example, a tertiary amine. Fatty amines have value in and of themselves, but they are commonly quaternized using a variety of alkylating agents to give fatty amine quats, betaines, sulfobetaines, or other quaternized derivatives having expanded utility.

Quaternized fatty amines have been used in a wide range of end-use applications, including fabric softening (see U.S. Pat. Nos. 5,574,179 and 6,004,913), shampoos and hair conditioning (U.S. Pat. Nos. 4,744,977, 6,322,778, and 7,951,762), hard surface cleaners (U.S. Pat. Nos. 6,268,324 and 6,821,943), cosmetics (U.S. Pat. Nos. 6,919,074 and 7,074,395), oral care (U.S. Pat. No. 7,534,816), antimicrobial handsoaps or cleaners (U.S. Pat. No. 6,010,991 and U.S. Pat. Appl. Publ. No. 2004/0071653), oilfield applications (U.S. Pat. Nos. 7,422,064 and 7,776,798) and agricultural uses (U.S. Pat. Appl. Publ. Nos. 2011/0015071 and 2010/0016163).

Quaternized fatty amines can be made by converting fatty esters or acids with a secondary amine to the amide derivative, followed by reduction of the carbonyl to give a terminal tertiary amine, which is then reacted with a quaternizing agent. In a preferred approach, the reduction step is avoided by reacting a fatty ester with an aminoalkyl-substituted tertiary amine. For instance, N,N-dimethyl-1,3-propanediamine (DMAPA) reacts with a fatty methyl ester to give a fatty amidoamine. The amidoamine has a terminal tertiary amine group that is easily quaternized. Common quaternizing agents are dimethyl sulfate, methyl chloride, benzyl chloride, ethylene oxide, and the like.

The fatty acids or esters used to make fatty amines and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, fatty amines and their derivatives made from these feedstocks appear to be unknown. Moreover, quaternized fatty amines and their derivatives have not been made from the $C_{18}$ unsaturated diesters that can be made readily by self-metathesis of a natural oil.

In sum, traditional sources of fatty acids and esters used for making quaternized fatty amines and their derivatives generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). New $C_{18}$ difunctional quaternized fatty amines and derivatives are also potentially available from oil or $C_{10}$ unsaturated acid or ester self-metathesis. In addition to an expanded variety of precursors, the unsaturation present in the precursors allows for further functionalization, e.g., by sulfonation or sulfitation.

SUMMARY OF THE INVENTION

In one aspect, the invention relates to a quaternary ammonium, betaine, or sulfobetaine composition derived from a fatty amine, wherein the fatty amine is made from a metathesis-derived $C_{10}$-$C_{17}$ monounsaturated acid, octadecene-1,18-dioic acid, or their ester derivatives. In another aspect, the invention relates to a quaternary ammonium, betaine, or sulfobetaine composition derived from a fatty amidoamine, wherein the amidoamine is made by reacting a metathesis-derived $C_{10}$-$C_{17}$ monounsaturated acid, octadecene-1,18-dioic acid, or their ester derivatives and an aminoalkyl-substituted tertiary amine such as DMAPA. The invention includes derivatives made by sulfonating or sulfitating the quaternized fatty amines or amidoamines. In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin. The quaternary ammonium, betaine, and sulfobetaine compositions and their sulfonated or sulfated derivatives are valuable for a wide variety of end uses, including cleaners, fabric treatment, hair conditioning, personal care (liquid cleansing products, conditioning bars, oral care products), antimicrobial compositions, agricultural uses, and oil field applications.

DETAILED DESCRIPTION OF THE INVENTION

In one aspect, the invention relates to a quaternary ammonium, betaine, or sulfobetaine composition derived from a fatty amine. The fatty amine is made from a metathesis-derived $C_{10}$-$C_{17}$ monounsaturated acid, octadecene-1,18-dioic acid, or their ester derivatives.

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived quaternized compositions of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoue and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts differential physical properties to quaternary ammonium, betaine, or sulfobetaine compositions made from them, including, for example, modified physical form, melting range, compactability, and other important properties. These differences should allow formulators that use the quaternary compositions greater latitude or expanded choice as they use them in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, usually by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive quaternized fatty amine or amidoamine compositions.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive quaternized fatty amine or amidoamine compositions.

An alternative to using a natural oil as a feedstock to generate the $C_{10}$-$C_{17}$ monounsaturated acid, octadecene-1, 18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

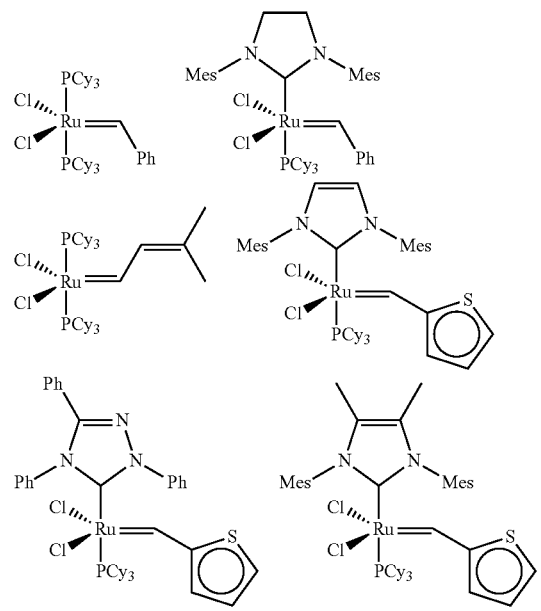

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

Fatty amines used to make the quaternized compositions of the invention can be made by reacting a metathesis-derived $C_{10}$-$C_{17}$ monounsaturated acid, octadecene-1,18-dioic acid, or their ester derivatives with a secondary amine, followed by reduction of the resulting fatty amide. They can also be made reducing a metathesis-derived acid or ester derivative to a fatty alcohol, followed by amination of the fatty alcohol. Thus, intermediates to the fatty amines are metathesis-derived fatty alcohols or fatty amides.

In one aspect, the ester derivative is a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make fatty amide precursors for the fatty amines or it can be purified to isolate particular alkyl esters prior to making fatty amides.

In another aspect, the ester derivative is the metathesis-derived triglyceride discussed in the preceding paragraph. Instead of transesterifying the metathesis-derived triglyceride with a lower alkanol to generate lower alkyl esters as described above, the metathesis-derived triglyceride, following olefin stripping, is reacted directly with a secondary amine to make a fatty amide mixture, which is then reduced to give a fatty amine. Alternatively, the metathesis-derived triglyceride, following olefin stripping, is reduced to give a fatty alcohol mixture, which is then aminated to give the fatty amine mixture.

The skilled person will appreciate that "ester derivative" here encompasses other acyl equivalents, such as acid chlorides, acid anhydrides, or the like, in addition to the lower alkyl esters and glyceryl esters discussed above.

In one synthetic approach, the metathesis-derived acid or ester derivative is reacted with a secondary amine to give a fatty amide, followed by reduction of the fatty amide to give the fatty amine.

Suitable secondary amines have a hydrogen and two hydrocarbyl groups attached to nitrogen. The hydrocarbyl groups are preferably linear, branched, or cyclic $C_1$-$C_{20}$ alkyl, $C_6$-$C_{20}$ aryl, or $C_7$-$C_{20}$ arylalkyl. More preferably, both of the hydrocarbyl groups are $C_1$-$C_6$ alkyl groups. Suitable secondary amines include, for example, N,N-dimethylamine, N,N-diethylamine, N,N,-dipropylamine, diisopropylamine, N,N-dibutylamine, N-methyl-N-cyclohexylamine, N-methyl-N-phenylamine, N-methyl-N-benzylamine, or the like, and mixtures thereof. N,N-Dimethylamine is cost-effective and is particularly preferred.

Suitable secondary amines include etheramines. Thus, amines that are reaction products of ammonia or primary amines and an alkylene oxide, for example 0.1 to 20 molar equivalents of ethylene oxide, propylene oxide, or the like, can be used. The amine can be, for instance, a monoalkylated derivative of a Jeffamine® M series polyether amine (product of Huntsman). In some instances of using an etheramine, it may be necessary to mask any hydroxyl functionality as an appropriate derivative, either before or after formation of the amide, so as to enable the subsequent reduction of this amide.

Although the fatty amides are made using a well-known process, the product mixture is unique because of the unconventional starting mixture of acid or ester derivatives. The reactants are typically reacted, with or without a catalyst under conditions effective to convert the starting acid, ester, or other derivative to an amide. The reaction temperature is typically within the range of 40° C. to 300° C., preferably from 50° C. to 250° C., and more preferably from 50° C. to 200° C.

Reduction of the fatty amide to give a terminal amine is accomplished using well-known methods, including reactions with a hydride reducing agent (boranes, aluminum hydrides, borohydrides, or the like), or catalytic hydrogenation. Suitable reducing reagents include, for example, borane, borane dimethylsulfide, sodium borohydride/iodine, lithium cyanoborohydride, aluminum hydride, lithium aluminum hydride, diisobutylaluminum hydride, and the like. For additional examples, see R. Larock, *Comprehensive Organic Transformations: A Guide to Functional Group Preparations* (1989), pp. 432-434, and M. Smith and J. March, *March's Advanced Organic Chemistry*, $5^{th}$ ed. a (2001), pp. 1549-1550.

In an alternative synthetic approach, the fatty amine is made by first reducing the metathesis-derived acid or ester derivative to give a fatty alcohol, followed by amination of the fatty alcohol. The metathesis-derived acid or ester derivative is reduced to a fatty alcohol using a metal hydride reagent (sodium borohydride, lithium aluminum hydride, or the like), catalytic hydrogenation, or other well-known techniques for generating the fatty alcohol (see, e.g., U.S. Pat. Nos. 2,865,968; 3,193,586; 5,124,491; 6,683,224; and 7,208,643, the teachings of which are incorporated herein by reference). Amination is then preferably performed in a single step by reacting the fatty alcohol with ammonia or a primary or secondary amine in the presence of an amination catalyst. Suitable amination catalysts are well known. Catalysts comprising copper, nickel, and/or alkaline earth metal compounds are common. For suitable catalysts and processes for amination, see U.S. Pat. Nos. 5,696,294; 4,994,622; 4,594,455; 4,409,399; and 3,497,555, the teachings of which are incorporated herein by reference.

In a preferred aspect of the invention, the fatty amine is a fatty amidoamine made by reacting a metathesis-derived $C_{10}$-$C_{17}$ monounsaturated acid, octadecene-1,18-dioic acid, or their ester derivatives with an aminoalkyl-substituted tertiary amine. This provides a product having tertiary amine functionality without the need to reduce a fatty amide to a fatty amine with a strong reducing agent. Suitable aminoalkyl-substituted tertiary amines have a primary amino group at one terminus, an alkylene group, and a tertiary amine group at the other end of the molecule. The alkylene group is preferably a $C_2$-$C_6$ linear or branched diradical such as ethylene, propylene, butylene, or the like. Thus, suitable aminoalkyl-substituted tertiary amines include, for example, N,N-dimethyl-1,2-ethanediamine, N,N-dimethyl-1,3-propanediamine (DMAPA), N,N-diethyl-1,3-propanediamine, N,N-dimethyl-1,4-butanediamine, and the like. DMAPA is particularly preferred. The primary amine group exhibits good reactivity with the acid or ester derivative, while the terminal tertiary amine is preserved in the product and provides a site for quaternization.

The relative amounts of secondary amine or aminoalkyl-substituted tertiary amine reacted with the ester or acid reactants depends on the desired stoichiometry and is left to the skilled person's discretion. In general, enough of the secondary amine (or aminoalkyl-substituted tertiary amine) is used to react with most or all of the available acid or ester groups, i.e., preferably greater than 90%, and more preferably greater than 95%, of the available acid or ester groups.

The tertiary amine group of the fatty amine or fatty amidoamine is quaternized to give a quaternary ammonium, betaine, or sulfobetaine composition. Suitable quaternizing methods and reagents are well known in the art. Common reagents include, for example, alkyl halides (methyl chloride, methyl bromide), dialkyl sulfates, carbonates, or phosphates (dimethyl sulfate, diethyl sulfate, dimethyl carbonate), benzyl chloride, acetyl chloride, ethylene oxide, and the like. Betaines are typically made by reacting the fatty amine or amidoamine with an w-haloalkylcarboxylic acid or alkali metal salt thereof (e.g., sodium monochloroacetate or potassium monochloropropionate) in the presence of a strong base. Sulfobetaines can be made by combining the fatty amine or amidoamine with epichlorohydrin, followed by sulfation with sodium bisulfite. An alternative procedure is outlined below in which epichlorohydrin is first reacted with sodium bisulfite in the presence of sodium hydroxide, and the fatty amine is added to that reaction mixture, followed by warming and neutralization, to give the sulfobetaine. In yet another approach, the sulfobetaine is made by reacting the fatty amine or amidoamine with an alkane sultone, as in U.S. Pat. No. 3,280,179. Detailed procedures are also provided below for making the quats using dimethyl sulfate as the quaternizing agent, and for making betaines using sodium monochloroacetate. Additional quaternization details appear in U.S. Pat. Nos. 3,280,179, 3,354,213, 4,743,660, 4,913,841, 5,679,150, 7,449,435, and 7,807,614, the teachings of which are incorporated herein by reference.

Some quaternary ammonium compositions from the fatty amines have the formula:

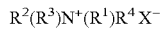

wherein:
$R^1$ is —$C_{10}H_{18}$—$R^5$ or —$C_{18}H_{34}$—$N^+(R^2)(R^3)R^4$ $X^-$; each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; and $R^5$ is hydrogen or $C_1$-$C_7$ alkyl. Preferably, $R^1$ is —$(CH_2)_8$—CH=$CHR^5$ or —$(CH_2)_8$—CH=CH—$(CH_2)_8$—$N^+(R^2)(R^3)R^4$ $X^-$.

Some betaines or sulfobetaine compositions have the formula:

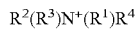

wherein:
$R^1$ is —$C_{10}H_{18}$—$R^5$ or —$C_{18}H_{34}$—$N^+(R^2)(R^3)R^4$; each of $R^2$ and $R^3$ is independently substituted or unsubstituted alkyl, aryl, alkenyl, oxyalkylene, or polyoxyalkylene; $R^4$ is $C_2$-$C_4$ alkylene carboxylate, $C_2$-$C_4$ alkylene sulfonate, or $C_2$-$C_4$ hydroxyalkylene sulfonate; and $R^5$ is hydrogen or $C_1$-$C_7$ alkyl. Preferably, $R^1$ is —$(CH_2)_8$—CH=$CHR^5$ or —$(CH_2)_8$—CH=CH—$(CH_2)_8$—$N^+(R^2)(R^3)R^4$.

Some quaternary ammonium compositions from the fatty amidoamines have the formula:

wherein: $R^1$ is —$C_9H_{16}$—$R^5$ or —$C_{16}H_{30}$-(CO)NH$(CH_2)_n$$(R^2)(R^3)R^4$ $X^-$;
each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; $R^5$ is hydrogen or $C_1$-$C_7$ alkyl; and n=2 to 8. Preferably, $R^1$ is —$(CH_2)_7$—CH=CH—$R^5$ or —$(CH_2)_7$—CH=CH—$(CH_2)_7$—(CO)NH$(CH_2)_n$$N^+(R^2)(R^3)R^4$ $X^-$.

Some amidoamine betaine or sulfobetaine compositions have the formula:

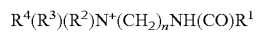

wherein:
$R^1$ is —$C_9H_{16}$—$R^5$ or —$C_{16}H_{30}$-(CO)NH$(CH_2)_n$$N^+(R^2)(R^3)R^4$; each of $R^2$ and $R^3$ is independently substituted or unsubstituted alkyl, aryl, alkenyl, oxyalkylene, or polyoxyalkylene; $R^4$ is $C_2$-$C_4$ alkylene carboxylate, $C_2$-$C_4$ alkylene sulfonate, or $C_2$-$C_4$ hydroxyalkylene sulfonate; $R^5$ is hydrogen or $C_1$-$C_7$ alkyl; and n=2 to 8. Preferably, $R^1$ is —$(CH_2)_7$—CH=CH—$R^5$ or —$(CH_2)_7$—CH=CH—$(CH_2)_7$—(CO)NH$(CH_2)_n$$N^+(R^2)(R^3)R^4$.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Specific examples of $C_{10}$, $C_{12}$, $C_{14}$, and $C_{16}$-based quaternized fatty amines and fatty amidoamines appear below:

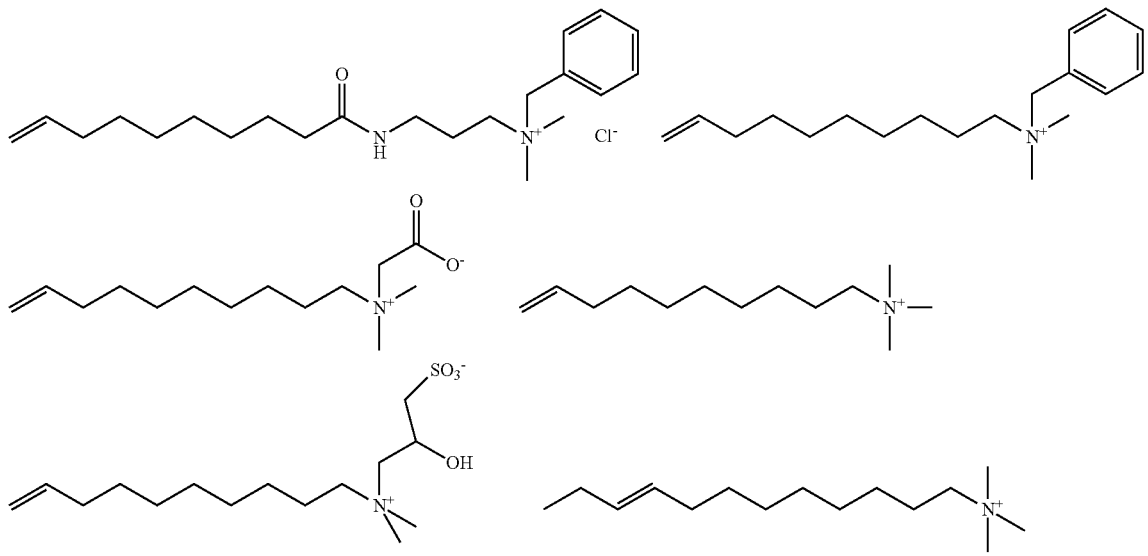

-continued
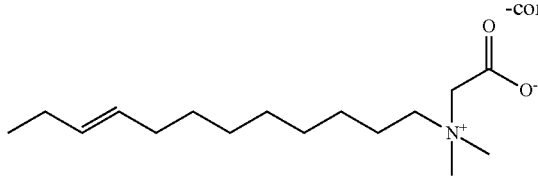
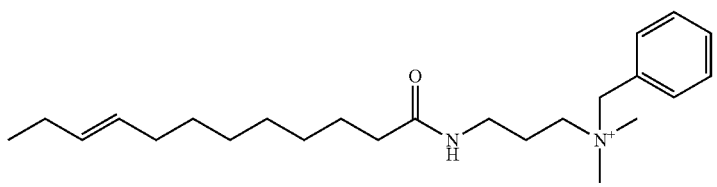
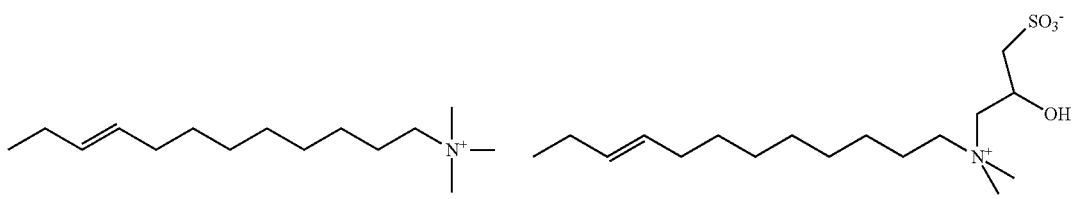
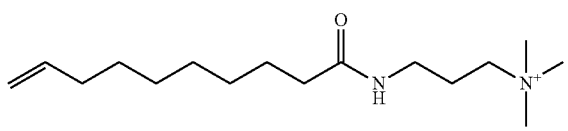
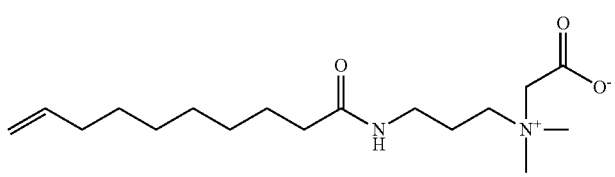
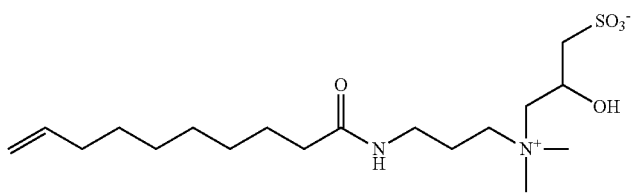
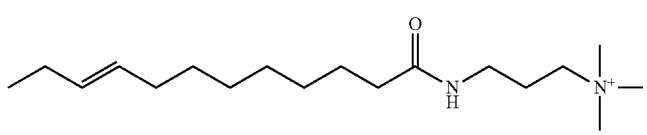
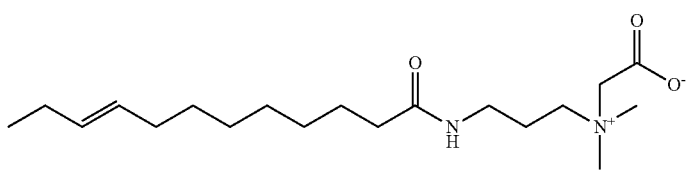
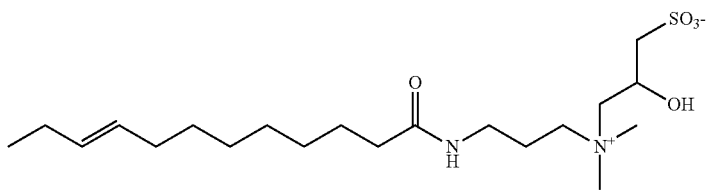
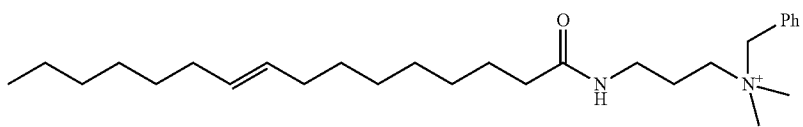

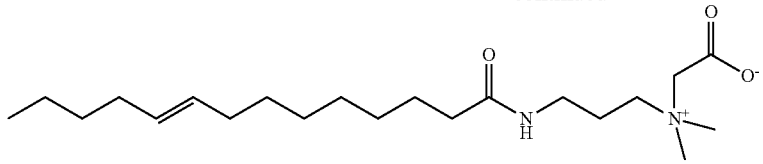

Some specific examples of $C_{18}$-based quaternized fatty amines and fatty amidoamines:

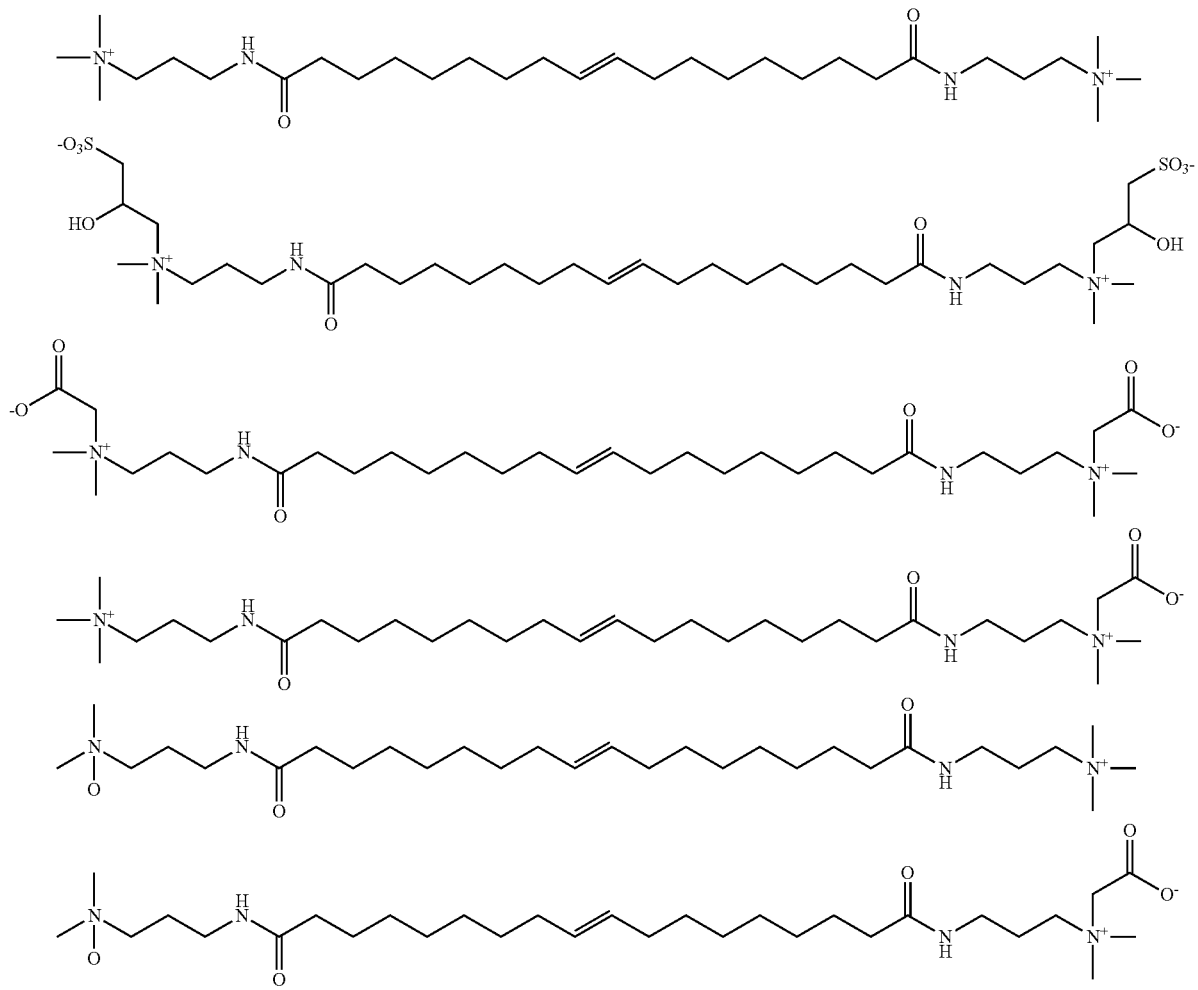

The quaternized fatty amine or fatty amidoamine product mixture can be complex when the ester derivative reacted with the secondary amine or aminoalkyl-substituted tertiary amine is a modified triglyceride made by self-metathesis of a natural oil and separation to remove olefins (see, e.g., the MTG and PMTG products described below) or an unsaturated triglyceride made by cross-metathesis of a natural oil and an olefin and separation to remove olefins (see, e.g., the UTG and PUTG products described below). As is evident from the reaction schemes, the quaternized MTG and PMTG products from DMAPA include an unsaturated $C_{18}$ quaternized diamidoamine as a principal component, while the UTG and PUTG products include a $C_{10}$ unsaturated quaternized amidoamine and one or more $C_{11}$ to $C_{17}$ unsaturated quaternized amidoamine components. (For example, with 1-butene as the cross-metathesis reactant, as illustrated, a $C_{12}$ unsaturated amidoamine component results.) Other components of the product mixtures are glycerin and saturated or unsaturated quaternized DMAPA amides. Despite the complexity, purification to isolate a particular species is often neither economical nor desirable for good performance.

Thus, in one aspect, a fatty amidoamine is quaternized. The fatty amidoamine is produced by reacting an aminoalkyl-substituted tertiary amine with a modified triglyceride made by self-metathesis of a natural oil. Self-metathesis of the natural oil provides a mixture of olefins and a modified triglyceride that is enriched in a $C_{18}$ unsaturated diester component along with $C_{18}$-$C_{18}$ saturated diesters. The olefins are stripped out, usually with heat and reduced pressure. When the modified triglyceride is reacted directly with DMAPA, a complex mixture results in which primary amino groups of DMAPA completely or partially displace glycerin from the glyceryl esters to form amidoamine functionalities. Representative amidoamine products below are made by reacting DMAPA with MTG-0 (modified triglyceride from soybean oil) or PMTG-0 (modified triglyceride from palm oil) followed by quaternization. One example is the MTG DMAPA sulfobetaine ("MTG-11"):

the product. The reaction is considered complete when the residual glyceride content of the product reaches the desired level.

The quaternized fatty amines or amidoamines and their derivatives have unsaturation that can be sulfonated or sulfated if desired. Sulfonation is performed using well-known methods, including reacting the olefin with sulfur trioxide. Sulfonation may optionally be conducted using an inert sol-

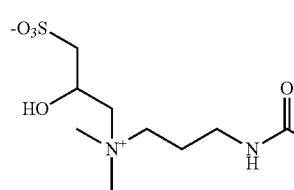

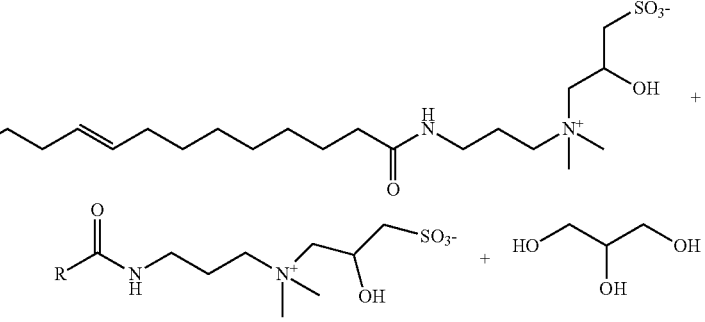

R = C16, C18 Sat. + Unsat.

In another aspect, the fatty amidoamine is produced by reacting an aminoalkyl-substituted tertiary amine with an unsaturated triglyceride made by cross-metathesis of a natural oil with an olefin. Cross-metathesis of the natural oil and olefin provides a mixture of olefins and an unsaturated triglyceride that is rich in $C_{10}$ and $C_{12}$ unsaturated esters as well as $C_{16}$-$C_{18}$ saturated esters. The olefins are stripped out, usually with heat and reduced pressure. When the unsaturated triglyceride is reacted directly with DMAPA, a complex mixture results in which primary amino groups of DMAPA completely or partially displace glycerin from the glyceryl esters to form amidoamine functionalities. Representative amidoamine products below are made by reacting DMAPA with UTG-0 (unsaturated triglyceride from cross-metathesis of soybean oil and 1-butene) or PUTG-0 (unsaturated triglyceride from cross-metathesis of palm oil with 1-butene), followed by quaternization. One example is the PUTG DMAPA dimethyl sulfate quat product ("PUTG-13"):

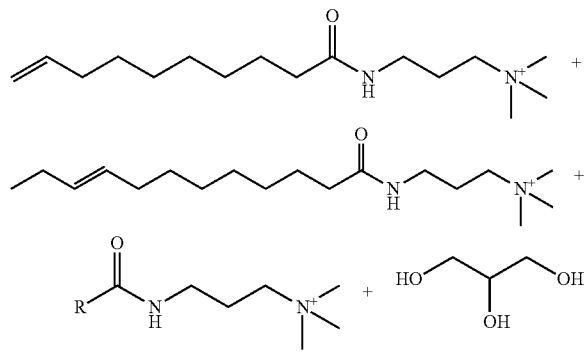

R = C16, C18 Sat.

The reaction to form the amidoamines from lower alkyl esters can be performed under a nitrogen sparge or under vacuum to remove liberated alcohol. When glyceride esters are reactants, the liberated glycerin need not be removed from vent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

The quaternized fatty amines, fatty amidoamines, and their sulfonated or sulfated derivatives can be incorporated into many compositions for use as, for example, surfactants, emulsifiers, skin-feel agents, film formers, rheological modifiers, biocides, biocide potentiators, solvents, release agents, and conditioners. The compositions find value in diverse end uses, such as personal care (liquid cleansing products, conditioning bars, oral care products), household products (liquid and powdered laundry detergents, liquid and sheet fabric softeners, hard and soft surface cleaners, sanitizers and disinfectants), and industrial or institutional cleaners.

The quaternized fatty amines or amidoamines and their derivatives can be used in emulsion polymerizations, including processes for the manufacture of latex. They can be used as surfactants, wetting agents, dispersants, or solvents in agricultural applications, as inert ingredients in pesticides, or as adjuvants for delivery of pesticides for crop protection, home and garden, and professional applications. The quaternized fatty amines or amidoamines and their derivatives can also be used in oil field applications, including oil and gas transport, production, stimulation and drilling chemicals, reservoir conformance and enhancement uses, and specialty foamers. The compositions are also valuable as foam moderators or dispersants for the manufacture of gypsum, cement wall board, concrete additives and firefighting foams. The compositions are used as coalescents for paints and coatings, and as polyurethane-based adhesives.

In food and beverage processing, the quaternized fatty amines or amidoamines and their derivatives can be used to lubricate the conveyor systems used to fill containers. When combined with hydrogen peroxide, the quaternized fatty amines or amidoamines and their derivatives can function as low foaming disinfectants and sanitization agents, odor reducers, and as antimicrobial agents for cleaning and protecting food or beverage processing equipment. In industrial, institutional and laundry applications, the quaternized fatty amines or amidoamines and their derivatives, or their combination with hydrogen peroxide, can be used to remove soil and sanitize and disinfect fabrics and as antimicrobial film-forming compositions on hard surfaces.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

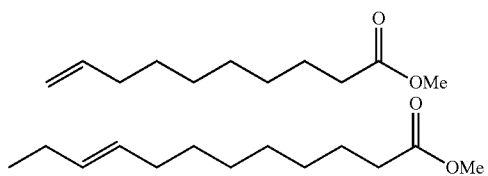

The procedures of U.S. Pat. Appl. Publ. No. 2011/0113679, the teachings of which are incorporated herein by reference, are used to generate feedstocks 010-0 and C12-0 as follows:

EXAMPLE 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt %), dimethyl 9-octadecenedioate (3.7 wt. %), and methyl 9-octadecenoate (1.8 wt. %).

EXAMPLE 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

EXAMPLE 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

EXAMPLE 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

EXAMPLE 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 ptorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

EXAMPLE 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

EXAMPLE 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 ptorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

| Isolation of C10-0 and C12-0 by Distillation | | | | | | |
|---|---|---|---|---|---|---|
| Distillation Fractions # | Head temp. (° C.) | Pot temp. (° C.) | Vacuum (μtorr) | Weight (g) | C10-0 (wt %) | C12-0 (wt %) |
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |

TABLE 1-continued

| Isolation of C10-0 and C12-0 by Distillation | | | | | | |
|---|---|---|---|---|---|---|
| Distillation Fractions # | Head temp. (° C.) | Pot temp. (° C.) | Vacuum (μtorr) | Weight (g) | C10-0 (wt %) | C12-0 (wt %) |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Precursor Syntheses:
C10-25: C10 DMA Amide

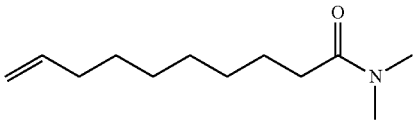

A round-bottom flask is charged with methyl ester feedstock C10-0 (235 g) and the mixture is degassed with nitrogen. Sodium methoxide (5 g of 30% solution in methanol) is added via syringe and the mixture is stirred for 5 min. Dimethylamine (67 g) is slowly added via sub-surface dip tube. After the addition, the mixture is heated to 60° C. and held overnight. The amide, C10-25, is recovered via vacuum distillation (120° C., 20 mm Hg). Yield: 241.2 g (96.3%). Iodine value=128.9 g $I_2$/100 g sample. $^1$H NMR (CDCl$_3$, δ (ppm)= 5.8 (CH$_2$=CH—); 4.9 (CH$_2$=CH—); 2.8-3.0 (—C(O)—N(CH$_3$)$_2$); 2.25 (—CH$_2$—C(O)—). Ester content (by $^1$H NMR): 0.54%.

C12-25: C12 DMA Amide

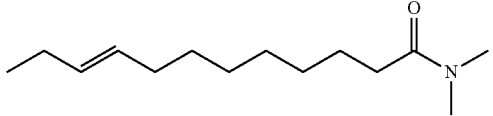 [SMILES: CC/C=C/CCCCCCCC(=O)N(C)C]

A round-bottom flask is charged with methyl ester C12-0 (900 g) and the feedstock is degassed with nitrogen at 60° C. Sodium methoxide (30 g of 30% solution in methanol) is added via syringe and the mixture is stirred for 5 min. Vacuum is then applied and the reaction vessel sealed. Dimethylamine (200 g) is slowly added via sub-surface dip tube against the static vacuum. After the addition, the remaining vacuum is released with nitrogen, and the mixture is heated to 70° C. for 1 h. The mixture is heated to 80° C., DMA is sparged through the liquid for 2 h, and the mixture is then heated to 90° C. for 1 h. The sparge is stopped, and the reaction is cooled to 75° C. Full vacuum is applied and held for 0.5 h. The vacuum is released, and 50% H$_2$SO$_4$ (16.3 g) and deionized water (200 mL) are added to quench the catalyst. The organic layer is washed with deionized water (2×300 mL, then 1×150 mL) and then 20% brine solution (50 mL). The organic layer is concentrated (full vacuum, 75° C.) and vacuum distilled (pot: 140-150° C.) to isolate amide C12-25. Iodine value: 112.8 g I$_2$/100 g sample; % moisture: 65 ppm. $^1$H NMR (CDCl$_3$), δ (ppm): 5.35 (—CH═CH—); 2.8-3.0 (—C(O)—N(CH$_3$)$_2$; 2.25 (—CH$_2$—C(O)—).

Amine Syntheses:

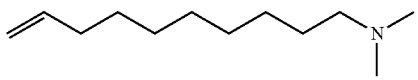

C10-38: C10 Amine

Amide C10-25 (475 g) is slowly added over 3 h to a stirring THF slurry of LiAlH$_4$ (59.4 g) under nitrogen while maintaining the temperature at 11-15° C. The mixture warms to room temperature and stirs overnight. The mixture is chilled in an ice bath, and water (60 g) is added cautiously, followed by 15% aq. NaOH solution (60 g) and then additional water (180 g) is added. The mixture warms to room temperature and is stirred for 1 h. The mixture is filtered, and the filter cake is washed with THF. The filtrates are combined and concentrated. NMR analysis of the crude product indicates that it contains approximately 16% 9-decen-1-ol, a side-product formed during the reduction of the amide. In order to sequester the alcohol, phthalic anhydride is to be added, thus forming the half-ester/acid. The product mixture is heated to 60° C. and phthalic anhydride (57.5 g) is added in portions. NMR analysis of the mixture shows complete consumption of the alcohol, and the mixture is vacuum distilled to isolate C10-38. Amine value: 298.0 mg KOH/g; iodine value: 143.15 g I$_2$/100 g sample; % moisture: 0.02%. $^1$H NMR (CDCl$_3$), δ (ppm): 5.8 (CH$_2$═CH—); 4.9 (CH$_2$═CH—); 3.7 (—CH$_2$—N(CH$_3$)$_2$).

C12-26: C12 Amine

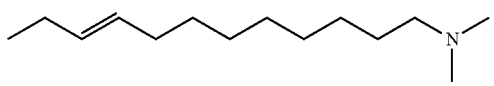

The procedure used to make C10-38 is generally followed with amide C12-25 (620 g) and LiAlH$_4$ (67.8 g). When the reaction is complete, water (68 g) and 15% aq. NaOH solution (68 g) and water (204 g) are used to quench the reaction. After the usual filtration and concentration steps, NMR analysis of the crude product shows approximately 16% 9-dodecen-1-ol to be present. And phthalic anhydride (30 g) is added in order to sequester the alcohol. The mixture is then vacuum distilled to give C12-26. Amine value: 258.1 mg KOH/g sample; iodine value: 120.0 g I$_2$/100 g sample. $^1$H NMR (CDCl$_3$), δ: 5.35 (—CH═CH—); 2.2 (—CH$_2$—N(CH$_3$)$_2$).

Amidoamine Syntheses:
C10-17: C10 DMAPA Amide

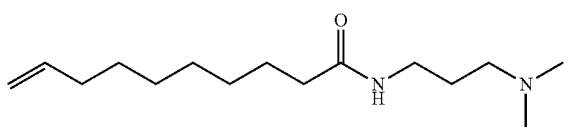 [SMILES: C=CCCCCCCCC(=O)NCCCN(C)C]

A round-bottom flask is charged with methyl ester C10-0 (500 g), DMAPA (331 g), and sodium methoxide/MeOH solution (0.5 wt. % sodium methoxide based on the amount of methyl ester). The contents are heated slowly to 140° C. and held for 6 h. The reaction mixture is vacuum stripped (110° C. to 150° C.). After cooling to room temperature, the product, C10-17, is analyzed. Amine value: 224.1 mg KOH/g; iodine value: 102.6 g I$_2$/100 g sample; titratable amines: 99.94%. $^1$H NMR (CDCl$_3$), δ (ppm): 5.75 (CH$_2$═CH—); 4.9 (CH$_2$═CH—); 3.3 (—C(O)—NH—CH$_2$—); 2.15 (—N(CH$_3$)$_2$).

C12-17: C12 DMAPA Amide

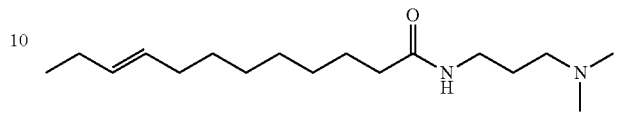

A round-bottom flask is charged with methyl 9-dodecenoate ("C12-0," 670 g). The mixture is stirred mechanically, and DMAPA (387 g) is added. A Dean-Stark trap is fitted to the reactor, and sodium methoxide (30 wt. % solution, 11.2 g) is added. The temperature is raised to 130° C. over 1.5 h, and methanol is collected. After 100 g of distillate is recovered, the temperature is raised to 140° C. and held for 3 h. $^1$H NMR shows complete reaction. The mixture is cooled to room temperature overnight. The mixture is then heated to 110° C. and DMAPA is recovered under vacuum. The temperature is slowly raised to 150° C. over 1.5 h and held at 150° C. for 1 h. The product, amidoamine C12-17, is cooled to room temperature. Amine value: 202.1 mg KOH/g; iodine value: 89.5 g I$_2$/100 g sample; free DMAPA: 0.43%; titratable amines; 100.3%. $^1$H NMR (CDCl$_3$), δ: 5.4 (—CH═CH—); 3.3 (—C(O)—NH—CH$_2$—); 2.2 (—N(CH$_3$)$_2$).

C10 Amine Derivatives:
C10-42: C10 Amine DMS Quat

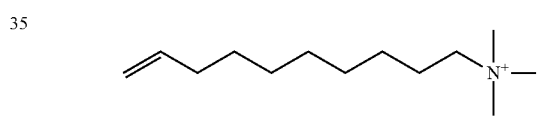

Amine C10-38 (90.1 g) and isopropyl alcohol (50 g) are charged to a flask under nitrogen, and the stirred mixture is warmed to 60° C. Dimethyl sulfate (59.23 g) is added dropwise with air cooling to maintain a reaction temperature of 60-70° C. Additional dimethyl sulfate (0.4 g) is added to ensure full conversion. The mixture is held at 70° C. for 3 h, then at 85° C. for 1 h. On cooling, C10-42 is analyzed: pH: 9.15 (1% in 9:1 IPA/water); free amine: 0.057 meq/g; moisture: 0.05 wt. %; IPA: 24.4 wt. %.

C10-40: C10 Benzyl Quat

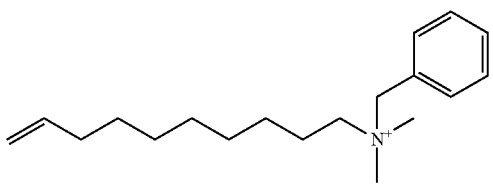 [SMILES: C=CCCCCCCCC[N+](C)(C)Cc1ccccc1]

A flask equipped with a condenser and nitrogen inlet is charged with C10-17 (86.56 g) and methanol (30 g). The mixture is warmed to 80° C. and benzyl chloride (56.37 g) is added. The temperature is raised to 82° C. for 1 h. On cooling, C10-40 is analyzed: pH: 8.6 (1% in 9:1 IPA/water); methanol: 17.5 wt. %; iodine value: 67.37; free amine: 0.065 meq/g; tertiary amine: 0.0169 meq/g; active alkyl quat: 2.645 meq/g.

C10-41: C10 Betaine

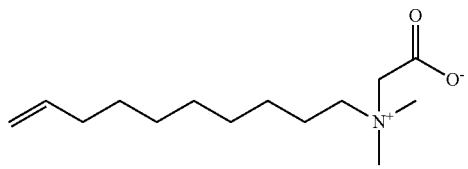 [SMILES: C=CCCCCCCCC[N+](C)(C)CC(=O)[O-]]

A flask is charged with C10-38 (114 g), water (180 mL), and sodium monochloroacetate (74.6 g). The mixture is heated to 100° C. and the pH is maintained at 7-9 by adding 50% NaOH. After 6 h, titration shows 9.7% chloride (theoretical: 10%). Upon cooling, C10-41 is analyzed: moisture: 49.58%; NaCl=9.95%. $^1$H NMR (D$_2$O), δ: 5.8 (CH$_2$=CH—); 4.9 (CH$_2$=CH—); 3.7 (—CH$_2$—N$^+$(CH$_3$)$_2$); 3.1 (—CH$_2$—N$^+$(CH$_3$)$_2$).

C10-43: C10 Amine Sulfobetaine

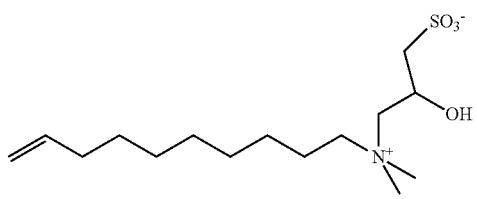

A flask equipped with nitrogen inlet is charged with sodium metabisulfite (50 g) and water (197 g), and the mixture is warmed to 40° C. Aqueous sodium hydroxide (0.6 g of 50% solution) is added. After stirring the mixture 5 min., epichlorohydrin (47.7 g) is added dropwise over 1 h, and the reaction exotherms to 70° C. The mixture is stirred at 70° C. for another 0.5 h. More aq. NaOH solution (0.6 g) is added and the mixture stirs briefly. Amine C10-38 (90 g) is added, and the temperature is increased to 90° C. After 1 h, the temperature is increased to 95° C. and held at 90-95° C. for 11.5 h. The pH is kept between 8.3 and 8.7 with 50% NaOH (aq) charges (2×1 g and 1×0.75 g). The reaction is judged complete when the NaCl level stabilizes at 7.60%. The mixture is cooled to give C10-43 as a clear solution (369.7 g). Analysis shows: pH: 7.53 (10% as is in DI water); NaCl: 7.82 wt. %; moisture: 48.8 wt. %. $^1$H NMR analysis supports the proposed structure (multiplet at ~4.7 for the methine proton, CH—OH).

C12 Amine Derivatives:

C12-45: C12 Amine DMS Quat

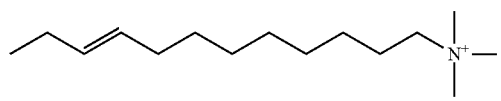 [SMILES: CC/C=C/CCCCCCCC[N+](C)(C)C]

A flask equipped with nitrogen inlet is charged with amine C12-26 (95.5 g), and the contents are warmed to 60° C. Dimethyl sulfate (54.28 g) is added dropwise. The mixture is cooled to maintain a temperature from 65-70° C. During the addition, a precipitate forms, and isopropyl alcohol (26.4 g) is added. The mixture is stirred at 70° C. for 3 h. Additional dimethyl sulfate (0.55 g) is added to ensure a complete conversion, and the mixture is stirred at 70° C. for 3 h, then at 85° C. for 1 h. The product, C12-45, is analyzed: pH: 6.36 (1% in 9:1 IPA/water); free amine: 0.040 meq/g; moisture: 0.4 wt. %; IPA: 11.6 wt. %.

C12-27: C12 Amine Benzyl Quat

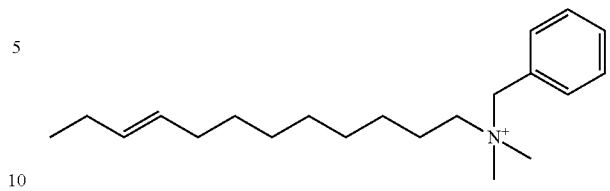

A round-bottom flask equipped with a magnetic stir bar, nitrogen inlet, thermocouple, condenser, and addition funnel is charged with amine C12-26 (92.77 g, 0.439 mol) and methanol (30 g). The mixture is warmed to 67° C. and benzyl chloride (52.77 g, 0.417 mol) is slowly added. More methanol (6.5 g) is added during the benzyl chloride addition. The reaction temperature is slowly raised to 82° C. After 2 h, free amine remains (by $^1$H NMR), so more benzyl chloride (1.6 g, 0.0126 mol) is added. The mixture stirs at 82° C. for 2 h. The product, C12-27, is cooled and analyzed: iodine value: 44.97; tertiary amine: 0.53%; methanol: 19.3 wt. %; free amine: 0.043 meq/g; moisture: 0.14 wt. %; active alkyl quat: 2.38 meq/g. $^1$H NMR analysis supports the proposed structure (singlet at ~4.9 ppm for the benzyl methylene).

C12-40: C12 Betaine

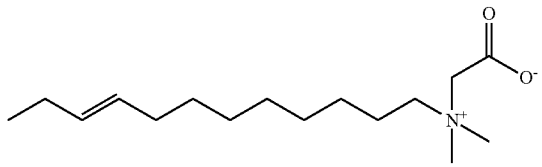 [SMILES: CC/C=C/CCCCCCCC[N+](C)(C)CC(=O)[O-]]

Amine C12-26 (117.7 g), water (342.9 g), and sodium monochloroacetate (66 g) are combined and heated to 100° C. The pH is maintained from 7-9 by adding 50% NaOH solution. After 7.5 h, titration shows 0.387% free amine. The mixture is cooled and neutralized to pH ~7 with 50% H$_2$SO$_4$. Analysis of the product, C12-40, shows: moisture: 63.8%; NaCl: 7.04%; free amine: 0.014 meq/g. $^1$H NMR (d$_4$-MeOH), δ: 5.3 (—CH=CH—); 3.7 (—C(O)—CH$_2$—N$^+$(CH$_3$)$_2$—); 3.1 (—C(O)—CH$_2$—N$^+$(CH$_3$)$_2$—).

C12-46: C12 Amine Sulfobetaine

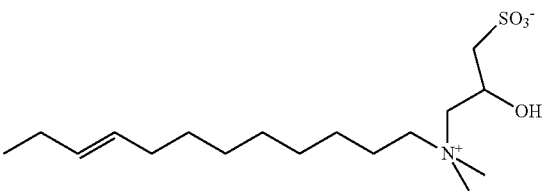

The procedure used to make sulfobetaine O10-43 is generally followed with amine C12-26 (100 g), sodium metabisulfite (48 g), water (203.5 g), 50% aq. NaOH (two 0.6-g portions), and epichlorohydrin (45.9 g). After addition of the tertiary amine, the reaction mixture is heated at 90-95° C. for a total of 10.5 hours while keeping the pH between 7.9 and 8.6 with 50% NaOH (aq) charges (2.3 g, 1 g, and 1 g) and monitoring NaCl level. After 8.5 h, the NaCl level stabilizes well below the expected theoretical value. 3-Chloro-2-hydroxypropanesulfonate, sodium salt hydrate (2.7 g) is added, and the mixture is held at 95° C. for an additional 2 h. The NaCl level stabilizes at 7.24% and the reaction is judged complete and cooled to room temperature. The pH of the product solution is adjusted to 8.1 with a small quantity of 50% H$_2$SO$_4$. The product, C12-46, is analyzed: pH: 7.53 (10% as is in deionized water); NaCl: 7.82 wt. %; moisture: 48.8 wt. %. $^1$H NMR analysis of a dried aliquot supports the proposed structure (multiplet at ~4.7 for the methine proton, CH—OH).

C10 Amidoamine Derivatives

C10-18: C10 DMAPA Quat

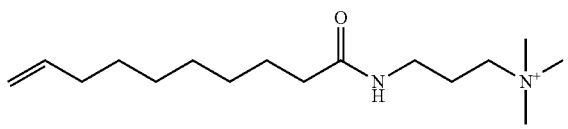 [SMILES: C=CCCCCCCCC(=O)NCCC[N+](C)(C)C]

A flask equipped with condenser and nitrogen inlet is charged with amidoamine C10-17 (151.3 g). After warming to 80° C., dimethyl sulfate (68.38 g) is added dropwise. The temperature is raised to 85° C. and the mixture is stirred for 2 h. Isopropyl alcohol (23.45 g) is added, and the mixture stirs for 1 h. The product, 010-18, is analyzed: IPA: 7.72 wt. %; pH: 8.41 (1% in 9:1 IPA/water); iodine value: 56.8; tertiary amine: 0.020 meq/g; moisture: 1.7 wt. %; quaternary actives: 91.2 wt. %.

C10-19: C10 DMAPA Quat Sulfonate

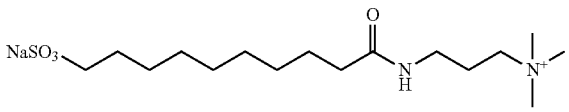

Methyl quat C10-18 (98.30 g) and water (216.3 g) are charged to a round-bottom flask equipped with stir bar, condenser, and thermocouple. The mixture is heated at 80° C. until homogeneous. Sodium metabisulfite (Na$_2$S$_2$O$_5$; 23.49 g, 1.03 eq. NaHSO$_3$) is added, and the mixture is held at 80° C. overnight. $^1$H NMR (D$_2$O) shows ~50% conversion to the sulfated product. The mixture is held at 80° C. for 48 h and then reanalyzed; there are no significant changes. Sulfur dioxide is bubbled through the mixture, which is then held at 80° C. overnight, but there are still no significant changes in the NMR spectrum. The reaction stirs at room temperature over the weekend. The pH is adjusted to 6.6 and the mixture is heated at 80° C. overnight. NMR analysis shows that olefin peaks have diminished. The pH has dropped to 3 and is adjusted with caustic to 7. After heating for another 24 h, NMR analysis shows no more changes, with ~4-5% olefin remaining. Additional sodium metabisulfite (0.91 g, 0.04 eq. NaHSO$_3$) is added, and the reaction mixture is heated overnight. The $^1$H NMR spectrum indicates complete conversion to the desired quat sulfonate, C10-19. Analysis shows: moisture: 60.1%; Na$_2$SO$_4$: 1.93%.

C10-31: C10 DMAPA Benzyl Quat

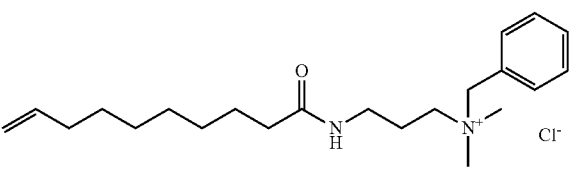 [SMILES: C=CCCCCCCCC(=O)NCCC[N+](C)(C)Cc1ccccc1 ; [Cl-]]

A round-bottom flask equipped with a stir bar, reflux condenser and thermocouple, is charged with amidoamine C10-17 (250.3 g) and methanol and heated to 67° C. Benzyl chloride (44 g) is added dropwise with heating removed at the start of the addition. The addition rate is adjusted to keep the temperature below 95° C. After benzyl chloride addition is complete, the temperature is adjusted to 82° C. and held for 2 h. Aqueous sodium hydroxide (0.33 g of 50% solution) is added, followed by more benzyl chloride (7 g), and the mixture is held at 82° C. for 2 h. $^1$H NMR shows the desired product benzyl quat. The mixture is cooled to room temperature and diluted with water (67 g). The resulting quat product, 010-31 (239 g), is analyzed: iodine value: 41.87; pH: 10.96 (as is); moisture: 27.9 wt. %; actives: 65.1 wt. %; tertiary amine: 0.0012 meq/g; methanol: 10.0 wt. %. $^1$H NMR analysis supports the proposed structure (singlet at ~4.3 ppm for the benzyl methylene).

C10-22: C10 DMAPA Betaine

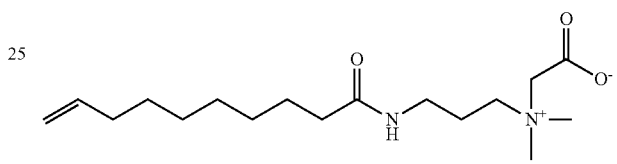

Amidoamine 010-17 (120 g), water (222.4 g), and sodium monochloroacetate (57.5 g) are charged to a round-bottom flask, and the contents are heated to 80° C. for 1 h. The pH (10% reaction mixture in water or isopropyl alcohol) is controlled between 8.5 and 10 using 50% aq. NaOH solution. The temperature is increased to 100° C. for 5 h with a condenser and nitrogen sparge included. Chloride titration is used to evaluate reaction completeness. After 5 h, hydrochloric acid is used to adjust pH to 7. The mixture is cooled and the product, 010-22, is analyzed: NaCl: 7.39%; free amine: 0.5%.

C10-23: C10 DMAPA Betaine Sulfonate

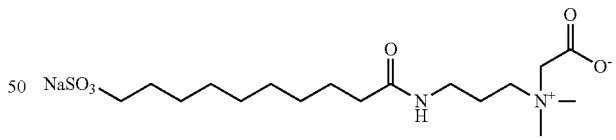

A round-bottom flask is charged with water (54 g) and sodium sulfite (14.3 g), and the pH adjusted to 6.6 with aqueous NaOH solution. The mixture is heated to 75° C. and tert-butylperoxybenzoate (36 μL) is added. After 30 min., betaine 010-22 (123 g) is added, followed by tert-butylperoxybenzoate (0.12 mL). The homogeneous mixture is maintained at pH=7 with sulfur dioxide. After 16 h, $^1$H NMR indicates complete consumption of starting material, and the betaine sulfonate product, 010-23, is cooled to room temperature. Analysis shows: moisture: 62.9%; Na$_2$SO$_4$: 1.96%; free NaCl: 4.54%; free sulfite: 0.65%.

C10-24: C10 DMAPA Sulfobetaine

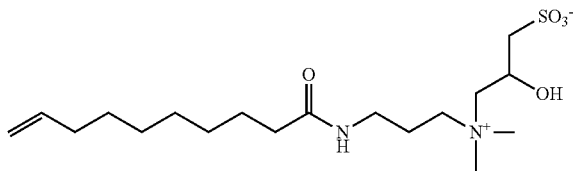

The procedure used to make sulfobetaine C10-43 is generally followed with amidoamine C10-17 (60 g), sodium metabisulfite (25.6 g), water (114 g), 50% aq. NaOH (two 0.3-g portions), and epichlorohydrin (24.4 g). Reaction continues at 75° C. for 3 h, and the pH (10% aqueous dilution) is kept between 8.2 and 8.9. After 3 h, the mixture cools to room temperature overnight. The mixture is reheated to 75° C. After 1 h, the pH has fallen to 8.1 and is increased with 50% NaOH (0.3 g). Reaction continues for 1 h. The reaction is judged complete when the NaCl level stabilizes at 6.55%. The mixture cools to room temperature, and the pH is adjusted to 6.95 with 50% $H_2SO_4$. The sulfobetaine product, C10-24, is analyzed: NaCl: 6.55 wt. %; solids: 51.8%; sulfobetaine actives (by solids-NaCl): 45.25%. $^1$H NMR analysis of a dried aliquot of the product mixture supports the proposed structure.

C12 Amidoamine Derivatives

C12-18: C12 DMAPA Quat

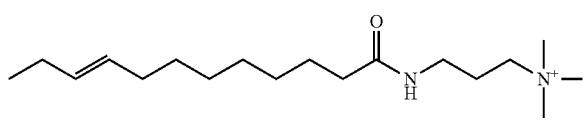 [SMILES: CC/C=C/CCCCCCCC(=O)NCCC[N+](C)(C)C]

A flask equipped with condenser and nitrogen inlet is charged with amidoamine C12-17 (155.8 g), which is warmed to 80° C. Dimethyl sulfate (68.38 g) is added dropwise. The reaction temperature is raised to 85° C. and held for 1 h, then to 95° C. for 3 h. Isopropyl alcohol (24.9 g) is added, and the mixture stirs for 1 h. Analysis of the quat product, C12-18, shows: IPA: 8.9 wt. %; iodine value: 53.95; pH: 8.07 (1% in 9:1 IPA/water); moisture: 0.6 wt. %.

C12-19: C12 DMAPA Quat Sulfonate

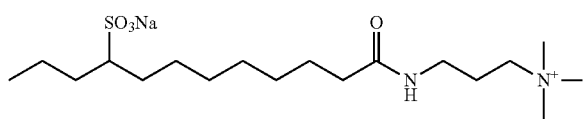

Methyl quat C12-18 (57.88 g) and water (115 g) are charged to a round-bottom flask and gently heated until homogeneous. Hydrogen peroxide (35% aq. $H_2O_2$, 4 drops) is added. Oxygen is bubbled through the solution, and $Na_2S_2O_5$ (12.62 g) is added in equal portions over 9 h. The mixture then stirs for 24 h. The pH is adjusted to 5 with dilute aq. NaOH. Analysis by $^1$H NMR shows 70% sulfate and 30% unreacted starting material. Analysis of the product shows: moisture: 60.1%; $Na_2SO_4$: 1.34%; free bisulfite: 10 mg/L.

C12-41: C12 DMAPA Benzyl Quat

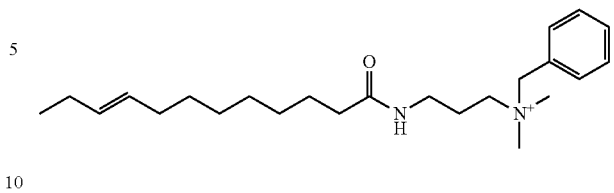

Amidoamine C12-17 (104.2 g) is charged to a reaction flask equipped with thermocouple, reflux condenser, mechanical stirrer, addition funnel, and nitrogen inlet. Methanol (28.1 g) is added, and the stirred solution is heated to 65° C. The heating mantle is removed, and benzyl chloride (40.99 g) is added dropwise, allowing the reaction temperature to increase on its own. After the benzyl chloride addition is complete, heating resumes, and the temperature is adjusted to 80° C. Reaction continues for 3.25 h. The mixture cools to room temperature overnight. The reaction mixture is rewarmed to 50° C. for 3 h. Additional benzyl chloride (0.92 g) is added, and the mixture is heated to 80° C. for 2 h. Deionized water (99 g) is added with stirring at 50° C., and the solution cools to room temperature. The benzyl quat, C12-41 (266.0 g) is analyzed: pH: 9.2 (1% in 9:1 IPA/water); free tertiary amine HCl: 0.089 wt. %; free amine: 0.47 wt. %; moisture: 35.9 wt. %; actives: 54.0 wt. %. $^1$H NMR analysis supports the proposed structure (singlet at ~4.5 ppm for the benzyl methylene group).

C12-22: C12 DMAPA Betaine

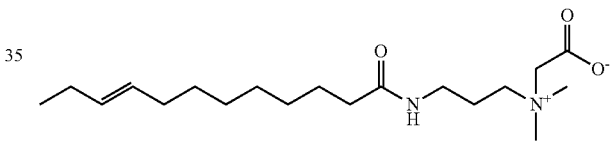

A round-bottom flask is charged with amidoamine C12-17 (210 g) and water (400 g). Sodium monochloroacetate (89 g) is added, and the mixture is heated to 80° C. The pH is maintained between 8 and 10 with 50% aq. NaOH (measuring pH as a 10% solution in water using pH strips). The temperature is raised to 100° C. and held for 4 h. The mixture is cooled to room temperature overnight. Water (100 g) is added to dilute the mixture, which is reheated to 100° C. for 4 h. Chloride titration shows 5.55% NaCl (expected 5.62%). The product, betaine C12-22, is cooled and analyzed: moisture: 62.13%; NaCl: 5.66%; free amine: 2.28%. $^1$H NMR ($d_4$-MeOH), δ: 5.4 (—CH=CH—); 3.8 (—C(O)—CH$_2$—N$^+$(CH$_3$)$_2$—); 3.2 (—C(O)—CH$_2$—N$^+$(CH$_3$)$_2$—).

C12-23: C12 DMAPA Betaine Sulfonate

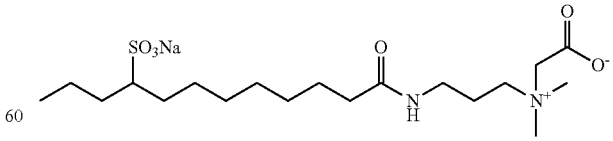

Betaine C12-22 (284.6 g) is combined with water and sodium sulfite (33 mg). Air is bubbled through the solution at 0.5 mL/min. With stirrring at room temperature, portions of sodium metabisulfite (5.99 g) are added every hour for 4 h, and the resulting solution stirs overnight. $^1$H NMR indicates 74% conversion. Additional sodium metabisulfite (2.39 g) is added, and the reaction is stirred overnight. $^1$H NMR shows 77% conversion. The product, sulfonate C12-23, is analyzed: moisture: 77.2%; Na$_2$SO$_4$: 1.6%; free bisulfite: 10 mg/L.

includes methyl 9-hexadecenoate. Fractional distillation at reduced pressure is used to isolate the desired product, methyl 9-hexadecenoate from other methyl esters.

C16-10: C16 DMAPA Quat

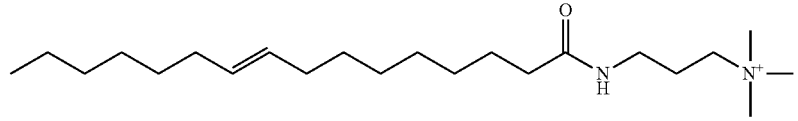

C12-24: C12 DMAPA Sulfobetaine

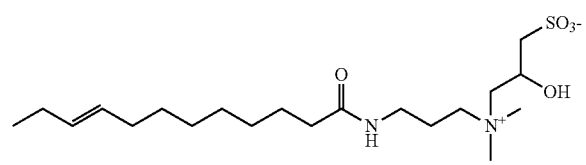

The procedure used to make sulfobetaine C10-24 is generally followed with amidoamine C12-17 (105 g), sodium metabisulfite (39.6 g), water (190 g), 50% aq. NaOH (two 0.6-g portions), and epichlorohydrin (37.8 g). Reaction continues at 80° C. for 3.5 h, and the pH (10% aqueous dilution) is kept between 8.2 and 8.6. After 3.5 h, the mixture cools to room temperature overnight. The mixture is reheated to 80° C. After 2 h, the pH is 8.5 and the NaCl level is 6.36%. The reaction is judged complete. The mixture cools to room temperature, and the pH is adjusted to 7.6 with 50% H$_2$SO$_4$. The sulfobetaine product, C12-24, is analyzed: NaCl: 6.34 wt. %; moisture: 49.7%; solids: 50.4%; sulfobetaine actives (by solids-NaCl): 44.0%. $^1$H NMR analysis of a dried aliquot of the product mixture supports the proposed structure.

Preparation of Methyl 9-Hexadecenoate ("C16-0") feedstock

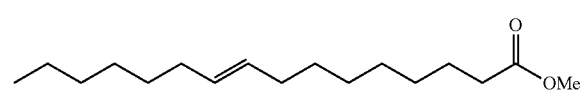 [SMILES: CCCCCC/C=C/CCCCCCCC(=O)OC]

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that A flask equipped with condenser and nitrogen inlet is charged with the corresponding C16 amidoamine C16-9 (105.5 g, prepared generally as in C12-17). After warming to 80° C., dimethyl sulfate (39.4 g) is added dropwise keeping the temperature <90° C. After the addition, IPA (20 g) is added to thin the product. The temperature is reduced to 70° C. and the mixture is stirred for 2 h. Analysis by perchloric acid titration (PAT) gives a value of 0.069 meq/g KOH (target=0.065 meq/g KOH) and the temperature is increased to 85° C. and held for 3 h. The product, C16-10, cools to room temperature, giving a waxy solid. Analysis shows: IPA: 10.6%; pH (90/10 IPA/H$_2$O): 6.7; moisture: 0.23%; free tertiary amine: 0.065 meq/g KOH; quat actives: 1.66 meq/g KOH.

C16-13: C16 DMAPA Betaine

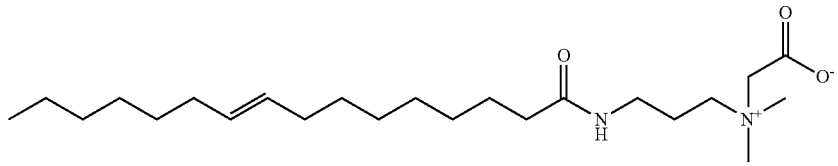 [SMILES: CCCCCC/C=C/CCCCCCCC(=O)NCCC[N+](C)(C)CC(=O)[O-]]

Amidoamine C16-9 (126.6 g, prepared generally as in C12-17), sodium monochloroacetate (SMCA, 44.7 g), and water (237 g) are charged to a round-bottom flask equipped with mechanical stirring, thermocouple, temperature controller, nitrogen inlet, and condenser. The mixture is heated to 80° C. with good agitation and becomes clear after approximately an hour. The pH (determined as 10% in water using test strips) is maintained between 8 and 10 by adding portions of 50% aq. NaOH as needed. As the reaction progresses, the mixture gels and water (100 g) is added to thin the mixture. The temperature is raised to 95° C. and held for 4 h. Analysis by $^1$H NMR shows complete conversion to DMAPA betaine C16-13. NaCl: 4.44%; moisture: 55.5%; free tertiary amine: 0.70%.

C16-14: C16 DMA Amide

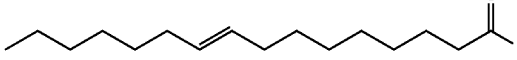

Methyl ester C16-0 (502 g, 1.8 mol) is charged to a vessel equipped with mechanical stirring, thermocouple, vacuum gauge and distillation sidearm. The material is heated to 50° C. and full vacuum is applied for 30 min. to dry and degas the system. The vessel is backfilled with nitrogen and sodium methoxide (30% solution in methanol, 20 g) is charged via syringe. The mixture is stirred 5 min. and then the pressure is reduced to approximately −25" Hg. The vessel is sealed under static vacuum and addition of dimethylamine (DMA) via sub-surface dip-tube is initiated. When the pressure in the vessel equalizes, the distillation sidearm is connected to a water trap/bubbler and charging continues at atmospheric pressure, adjusting the rate of addition to minimize blow-by (indicated by bubbling in scrubber). When a slight excess of DMA has been charged, the vessel is stirred for 3 h at 60° C. under nitrogen. $^1$H NMR analysis indicates complete consumption of the methyl ester, and the mixture is cooled to room temperature overnight. The mixture is reheated to 65° C. and vacuum-stripped to remove excess DMA and MeOH. When stripping is complete, the vessel is backfilled with nitrogen. Concentrated HCl is added in portions until a moistened pH test strip indicates a slightly acidic pH. After stirring 15 min., the neutralized mixture is washed with water (3×200 mL), adding 20% NaCl as needed to facilitate phase separation. The washed product is heated to 65° C. and vacuum is slowly applied to remove water. When stripping is complete, the vessel is backfilled with nitrogen and the stripped product is filtered through a plug of silica gel on a glass frit to remove a fine precipitate. The product remains hazy, and it is diluted with ethyl acetate and filtered again through a pad of diatomaceous earth, giving a clear yellow liquid. Volatiles are removed via rotary evaporator, then under high vacuum, affording dimethylamide C16-14 as a light yellow oil (509.4 g; 96.8% yield). $^1$H NMR analysis is consistent with the target structure and shows 0.8% methyl ester remaining. Further analysis shows: moisture: 0.04%; iodine value: 89.3 g I$_2$/100 g sample.

C16-15: C16 Amine

Amide C16-14 (358.8 g) is slowly added over 3 h to a stirring THF slurry of LiAlH$_4$ (37.5 g) under nitrogen while maintaining the temperature at 11-15° C. The mixture warms to approximately 20° C. and stirs 2 h. The mixture is chilled in an ice bath, and water (37.5 g) is added cautiously, followed by 15% aq. NaOH solution (37.5 g) and then additional water (112.5 g) is added. The mixture warms to room temperature and is stirred for 1 h. The mixture is filtered, and the filter cake is washed with THF. The filtrates are combined and concentrated. Phthalic anhydride (20 g) is added in portions, and the mixture is vacuum distilled to isolate C16-15. $^1$H NMR analysis of the product shows approximately 6.5% fatty alcohol by-product remaining, and the product is subsequently treated with additional phthalic anhydride, and then redistilled as above. Amine value: 187.8 mg KOH/g; iodine value: 94.4 g I$_2$/100 g sample; % moisture: 0.02%. $^1$H NMR (CDCl$_3$), δ (ppm): 5.8 (CH$_2$=CH—); 4.9 (CH$_2$=CH—); 3.7 (—CH$_2$—N(CH$_3$)$_2$).

C16-16: C16 Betaine

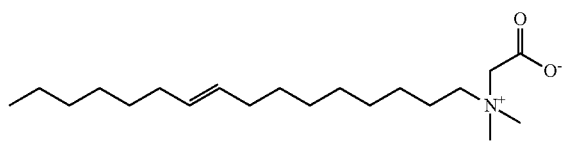 [SMILES: CCCCCC/C=C/CCCCCCCC[N+](C)(C)CC(=O)[O-]]

A round-bottom flask equipped with mechanical stirrer, thermocouple, temperature controller, heating mantle, and pH probe is charged with amine C16-15 (123.2 g), water (200 g), and sodium monochloroacetate (64.6 g). The milky reaction mixture is heated to 80° C. for 1 h, maintaining pH between 7 and 10 by addition of 50% aq. NaOH. The reaction mass is then heated to 95° C.; after an additional 1 h, the mixture becomes clear and begins to thicken. Additional water (50 g) is added and NaOH is added to maintain pH between 7 and 8. After 4 h total time at 95° C., the reaction mixture is allowed to cool. $^1$H NMR (sample dried, dissolved in MeOD) indicates complete consumption of sodium monochloroacetate and 75% conversion of amine to quaternary ammonium. The reaction mixture is re-heated to 95° C. and more sodium monochloroacetate (6 g) is added. Again, the pH is maintained between 7 and 8 by adding 50% aq. NaOH. After 1.5 h, $^1$H NMR indicates 85% conversion of amine and a trace of residual chloroacetate. Water (50 mL) and sodium monochloroacetate (7.2 g) are added to the thick mixture. After 1 h, NMR indicates 92% amine conversion. More sodium monochloroacetate (1.9 g) is added. After 1 h, conversion is 95.6%. The pH is adjusted to 7.6 with aq. NaOH, and the mixture is heated 4 h at 95° C. At this point, $^1$H NMR indicates 98.2% conversion of amine. The mixture is cooled to 60° C. and the light-colored, thick betaine product, C16-16, is analyzed: moisture: 60.0%; free tertiary amine: 0.024 meq/g; NaCl: 7.19%.

C16-17: C16 Amine Benzyl Quat

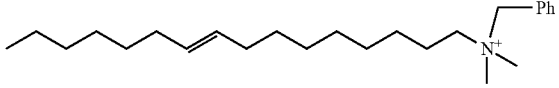 [SMILES: CCCCCC/C=C/CCCCCCCC[N+](C)(C)Cc1ccccc1]

Amine C16-15 (70.0 g) is charged to a flask equipped with a thermocouple, reflux condenser, mechanical stirrer, addition funnel, and nitrogen inlet. Methanol (25.2 g) is added with stirring, and the solution is heated to 65° C. Benzyl chloride (30.3 g) is added dropwise over ~45 min., allowing the internal temperature to increase to ~72° C. The reaction temperature is adjusted to 80° C., held for 4 h, then cooled to room temperature and allowed to stand overnight under nitrogen. On cooling, the reaction mixture gels, and additional methanol (5 g) is added. The mixture is heated to 50° C. Analysis by NMR shows no residual benzyl chloride, but indicates a small quantity of free tertiary amine. Additional benzyl chloride (0.94 g) is added and the mixture is stirred at 80° C. for 4 h. Analysis by $^1$H NMR confirms a complete reaction. The mixture is cooled and the benzyl quat, C16-17, is analyzed: moisture: 2.83%; free tertiary amine: 0.0015 meq/g; alkyl quaternary actives=2.28 meq/g.

Feedstock Synthesis

Preparation of Dimethyl 9-Octadecene-1,18-dioate ("Mix-0" or "C18-0")

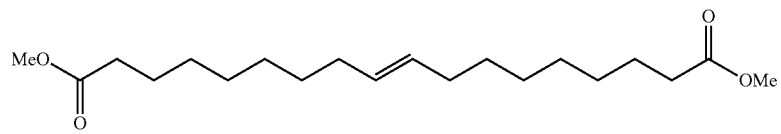 [SMILES: COC(=O)CCCCCCC/C=C/CCCCCCCC(=O)OC]

Eight samples of methyl 9-dodecenoate (10.6 g each, see Table 2) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenylidene)-(tricyclohexylphosphine), product of Materia) is added to the methyl 9-dodecenoate (amount indicated in Table 2) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 2. "Mix-0" is an 80:20 trans-/cis-isomer mixture obtained from the reaction mixture. Crystallization provides the all-trans-isomer feed, "C18-0."

180° C. for 2 h. The mixture is cooled to 110-120° C., concentrated HCl was added, and the contents are stirred vigorously for 15 min. The heating mantle is removed, and when the temperature reaches 90° C., deionized water is added to triturate the product. The slurry cools to room temperature and is filtered. The solids are washed several times with water. The diamide product, C18-26, is analyzed: melting point: 97-101° C.; amine value: 230.4 mg KOH/g; free DMAPA: 0.08%; moisture: 0.08%; titratable amines: 98.95%. $^1$H NMR (CDCl$_3$), δ (ppm): 5.35 (—CH=CH—); 3.3 (—C(O)—NH—CH$_2$—); 2.2 (—N(CH$_3$)$_2$).

MIX-26: C18 DiDMAPA Amide (80% trans, 20% cis)

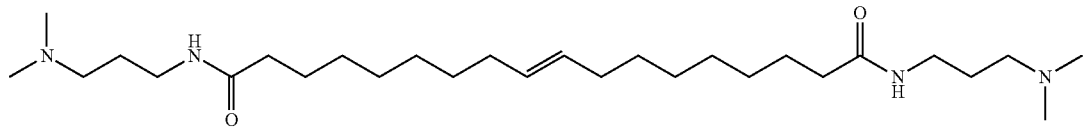

TABLE 2

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

C18-26: C18 DiDMAPA Amide (100% trans-)

Dimethyl ester C18-0 (824.3 g), DMAPA (519.5 g), and sodium methoxide solution (2.4 wt. % NaOMe based on methyl ester) are heated slowly to 140° C. and held for several hours. A subsurface nitrogen sparge is utilized at the end to facilitate the removal of methanol. The temperature is reduced to 100° C., and the contents are vacuum stripped. A solution made from deionized water (1.0 L) and 50% H$_2$SO$_4$ (11 g) is added slowly to the molten reaction product. The mixture cools, and the pasty solids are isolated by filtration. The solids are washed with deionized water, and the filtrate is extracted with chloroform (2×250 mL). The chloroform extracts are concentrated, and the resulting yellow oil is identified as the cis-enriched product by $^1$H NMR. The yellow oil is redissolved in CHCl$_3$, filtered through silica, and combined with the pasty solids. Additional CHCl$_3$ (100 mL) is added to the contents, and the mixture is swirled on a rotary evaporator at 70° C. until homogeneous. Vacuum is applied, and the CHCl$_3$ is removed, followed by water. Evaporation is discon-

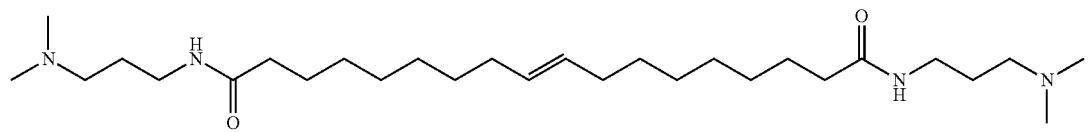

Dimethyl ester C18-0 (545.6 g), DMAPA (343.3), and sodium methoxide solution (1.1 wt. % NaOMe based on methyl ester) are combined, heated slowly to 150° C., and held 10.5 h. Additional DMAPA (100 mL) is added, and the mixture is heated to 150-160° C. for 4 h, then stirred overnight at 125° C. Additional 30% sodium methoxide in MeOH (10 g) is added, and the mixture is heated at 155-160° C. for 4 h. More DMAPA (50 mL) is added, and the mixture is heated at tinued when the product remains a solid at 98° C. The cooled product, Mix-26, is analyzed: amine value: 229.1 mg KOH/g sample; free DMAPA: 0.08%; moisture: 0.09%; total alkalinity: 4.08 meq/g. $^1$H NMR (CDCl$_3$), δ (ppm)=5.3 (—CH=CH—); 3.25 (—C(O)—NH—CH$_2$—); 2.2 (—N(CH$_3$)$_2$). $^{13}$C NMR (CDCl$_3$), δ (ppm)=130 (trans —CH=CH—); 129.5 (cis, —CH=CH—). Product ratio: 79.3% trans, 20.7% cis.

C18-27: C18 DiDMAPA DiQuat (100% trans-)

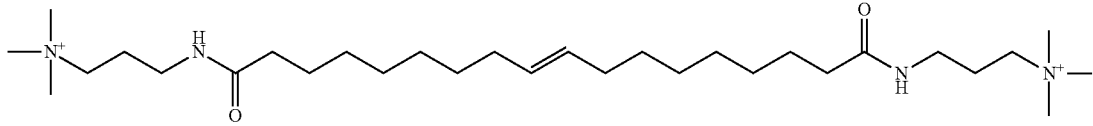

A flask equipped with nitrogen inlet is charged with diamide C18-26 (83.0 g) and isopropyl alcohol (68.8 g), and the mixture is warmed to 70° C. Additional IPA (49.11 g) is added to give a homogeneous solution. Dimethyl sulfate (92.0 g) is added. The outer flask is air cooled and the addition rate is adjusted to keep the reaction temperature ~70° C. The mixture stirs at 70° C. for 3 h, then at 85° C. for 3 h. The resulting diquat product, C18-27, is analyzed: iodine value: 14.52; pH: 7.72 (1% in 9:1 IPA/water); IPA: 28.1 wt. %; free amine: 0.055 wt. %; moisture: 0.48 wt. %; actives (alkyl quat): 73.0 wt. %.

MIX-27: C18 DiDMAPA DiQuat (80:20 trans-/cis-)

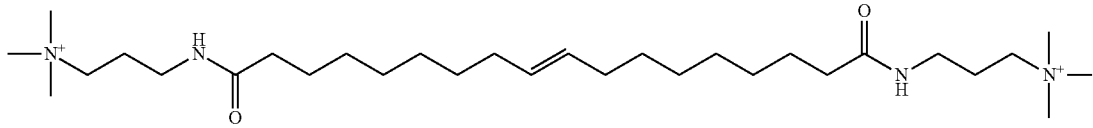

A flask equipped with condenser and nitrogen inlet is charged with diamide Mix-26 (157.3 g), which is warmed to 80° C. Dimethyl sulfate (68.38 g) is added dropwise. The reaction temperature is raised to 85° C. and the mixture is stirred for 2 h. Isopropyl alcohol (23.45 g) is added, and the mixture stirs for 1 h. The diquat product, Mix-27, is analyzed: IPA: 7.72 wt. %; pH: 8.41 (1% in 9:1 IPA/water); iodine value: 56.76; tertiary amine: 0.020 meq/g; moisture: 1.7 wt. %; quaternary actives: 91.2 wt. %.

C18-28: C18 DiDMAPA DiQuat Sulfonate (100% trans-)

A nitrogen-purged flask is charged with sodium metabisulfite (42.3 g) and water (190 g), and the mixture is warmed to 40° C. Aqueous sodium hydroxide (0.6 g of 50% solution) is added. The mixture stirs briefly, and epichlorohydrin (40.4 g) is added dropwise over 1 h. The mixture is allowed to exotherm to 60° C. The mixture stirs at 70° C. for 0.5 h, and more 50% NaOH (0.6 g) is added. After brief stirring, diamide C18-26 (100 g) is added in one portion. The ensuing exotherm warms the mixture to 80° C. The temperature is held at 80° C. and the mixture stirs for 3.5 h. The pH is kept between 8.2 and 8.6 with 50% NaOH. After 3.5 h, the NaCl content of the mixture is 6.75%. The mixture cools to room temperature overnight. The mixture is reheated to 80° C. After 0.5 h, the pH is 8.1, and 50% NaOH (aq.) is used to raise the pH to 9.1. After 1 h, the NaCl level remains at 6.75% and the reaction is judged complete. The mixture cools to room temperature and the pH is adjusted to 7.94 with 50% aq. H$_2$SO$_4$. Analysis of the sulfobetaine, C18-31, shows: NaCl: 6.83 wt. %; moisture: 51.0%; solids: 49.0%; sulfobetaine actives (by solids-NaCl): 42.2%. $^1$H NMR analysis of a dried aliquot of the product mixture supports the proposed structure.

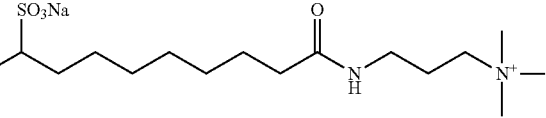

Diquat C18-27 (216.5 g), Na$_2$S$_2$O$_5$ (42.75 g), water (400.5 g), and t-butylperoxybenzoate (0.44 g) are combined and heated with stirring at 75° C. for 18 h. $^1$H NMR indicates 96% conversion. Isopropyl alcohol (from the C18-27 starting material) is stripped. The quat sulfonate, C18-28, is analyzed: moisture: 60.7%; Na$_2$SO$_4$: 2.85%; free sulfite: 1.48%.

C18-31: C18 DiSulfobetaine (100% trans-)

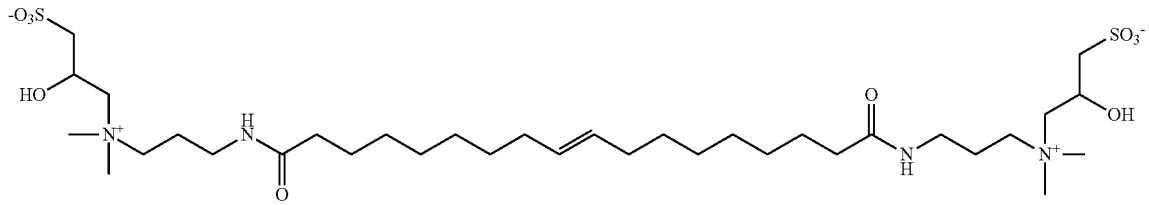

MIX-31: C18 DiSulfobetaine (80:20 trans-/cis-)

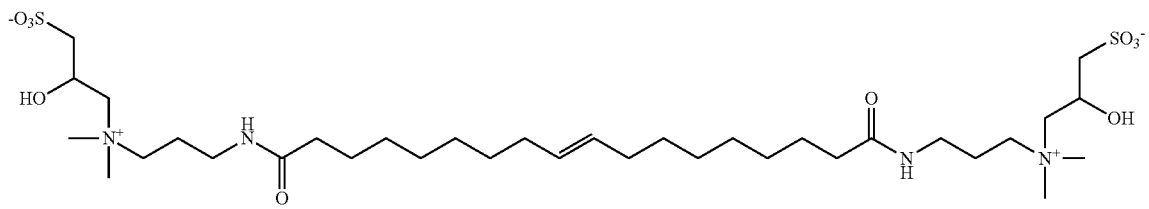

The procedure used to make C18-31 is generally followed with diamide Mix-26 (96 g), sodium metabisulfite (40.7 g), water (175 g), 50% aq. NaOH (two 0.5-g portions), and epichlorohydrin (38.8 g). The temperature is held at 75° C. and the mixture stirs for 3 h. The pH is kept between 8.3 and 8.7 with 50% NaOH. The mixture cools to room temperature overnight. The mixture is reheated to 75° C. After 0.5 h, the pH is 8.2, and 50% NaOH (aq.) is used to raise the pH to 8.8. The mixture stirs an additional 4.5 h at 75° C. The NaCl level is 6.81% and the reaction is judged complete. The mixture cools to room temperature and the pH is adjusted to 8.0 with 50% aq. $H_2SO_4$. Analysis of the sulfobetaine, Mix-31, shows: NaCl: 6.94 wt. %; moisture: 48.9%; solids: 51.1%; sulfobetaine actives (by solids-NaCl): 44.1%. $^1$H NMR analysis of a dried aliquot of the product mixture supports the proposed structure.

C18-32: C18 DiBetaine (100% trans-)

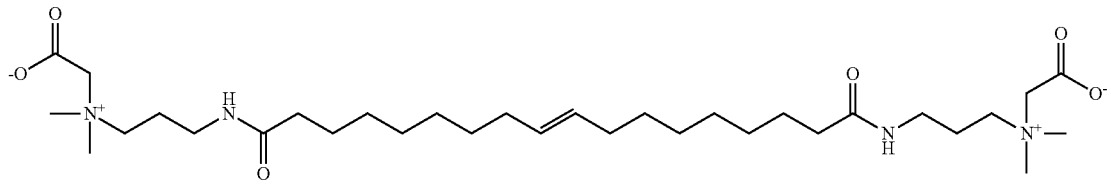

Diamide C18-26 (224.0 g) is charged to a flask, followed by water (614.3 g) and sodium monochloroacetate (106 g). The mixture is heated to 100° C. and the pH is kept from 7-9 by adding 50% NaOH. After 3 h, titration shows 0.038% free amine and 5.68% NaCl. The mixture is cooled, neutralized to pH ~8 with 50% $H_2SO_4$, and analyzed: moisture: 65.4%; NaCl: 5.68%; free amine: 1.4 meq/g. $^1$H NMR ($d_4$-MeOH), δ: 5.25(—CH═CH—); 3.7 (—C(O)—CH$_2$—N$^+$(CH$_3$)$_2$—); 3.05 (—C(O)—CH$_2$—N$^+$(CH$_3$)$_2$—).

MIX-32: C18 DiBetaine (80:20 trans-/cis-)

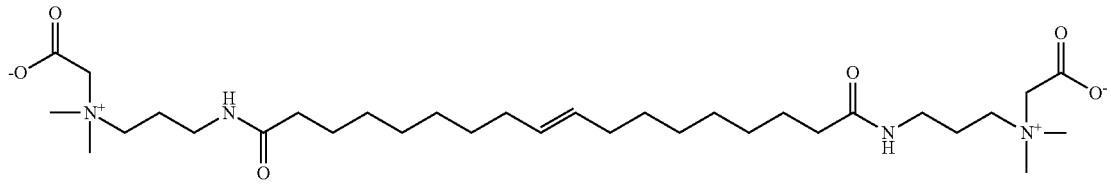

Diamide Mix-26 (128.17 g) is charged to a flask, followed by water (282.0 g) and sodium monochloroacetate (62.8 g). The mixture is heated to 100° C. and the pH is kept from 7-9 by adding 50% NaOH. After several hours, titration shows 6.53% free NaCl. The mixture is cooled, neutralized to pH ~8 with 50% $H_2SO_4$, and analyzed: moisture: 59.7%; NaCl: 6.68%; free amine: 0.031 meq/g.

C18-33: C18 DiBetaine Sulfonate (100% trans-)

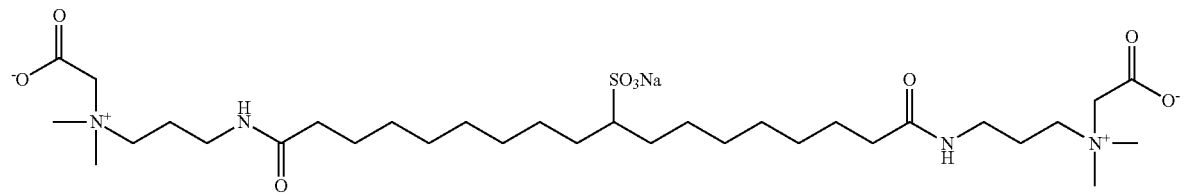

Dibetaine C18-32 (447.7 g of 32% active), $Na_2S_2O_5$ (23.45 g), water (197 g), $Na_2SO_3$ (0.78 g), and t-butylperoxybenzoate (0.24 g) are combined and stirred at 80° C. for 17.5 h while adjusting the pH to ~6 with periodic additions of NaOH. $^1$H NMR indicates 70% conversion. Water (100 mL) and additional catalyst are added and heating continues for 5.5 h, then overnight. $^1$H NMR indicates that conversion to the sulfonate is 82% complete. The sulfonate, C18-33, is analyzed: moisture: 68.8%; $Na_2SO_4$: 1.70%; NaCl: 4.18%; sulfites (by test strip): 200-400 mg sulfite/L.

C18-34: C18 DiDMAPA MonoQuat (100% trans-)

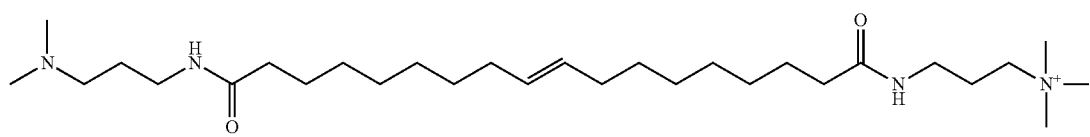

A round-bottom flask is charged with diamine C18-26 (225.8 g), which is purged with nitrogen and heated to 70° C. Isopropyl alcohol (105.26 g) is added. Dimethyl sulfate (DMS) (58.8 g) is then added slowly via addition funnel so that the temperature is maintained around 70° C. After the DMS addition is complete, the mixture is held at 70° C. for 3 h and then at 85° C. for 1 h. Free amine (by PAT): 1.199 meq/g. Theoretical expected PAT value for 50% quaternization of available tertiary amine is 1.196 meq/g.

MIX-34: C18 DiDMAPA MonoQuat (80:20 trans-/cis-)

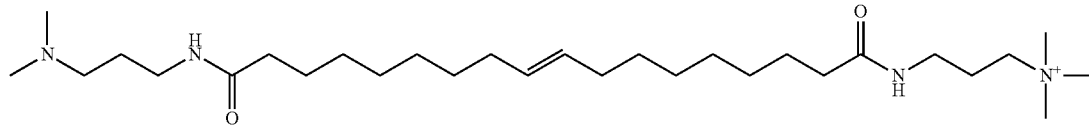

The procedure used to make C18-34 is generally followed with diamine Mix-26 (241.6 g), isopropyl alcohol (98.4 g), and dimethyl sulfate (60 g). After the DMS addition is complete, the reaction was held at 70° C. for 3 h and then at 85° C. for 3 h. Perchloric acid titration shows 1.317 meq/g of free amine. $^1$H NMR analysis ($CD_3OD$) shows 49% free amine and 51% quaternized amine, based on the integration of the methyl group signals at 2.25 and 3.11 ppm, respectively.

C18-35: C18 DiDMAPA Quat AO (100% trans-)

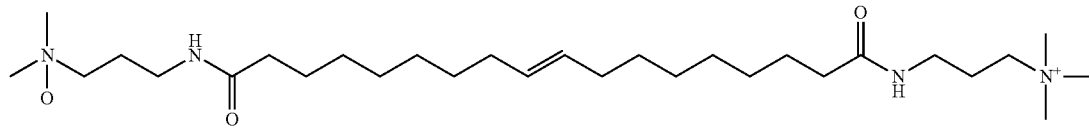

Amine monoquat C18-34 (75% solids, 192.3 g), deionized water (205.0 g), and Hamp-Ex 80 (0.5 g) are charged to a round-bottom flask. The mixture is heated to 70° C., adjusting pH to >8 with citric acid. Aqueous $H_2O_2$ (35%, 22.86 g) is added dropwise, maintaining temperature below 70° C. After peroxide addition is complete, the mixture is maintained at 70° C. for 20 h. $^1$H NMR indicates complete conversion of tertiary amine to amine oxide. The mixture is cooled to room temperature. Titration shows: amine oxide: 0.50 meq/g; free amine: 0.042 meq/g; cationic actives: 0.62 meq/g; free peroxide: 0.08%; and water: 55.8%.

MIX-35: C18 DiDMAPA Quat AO (80:20 trans-/cis-)

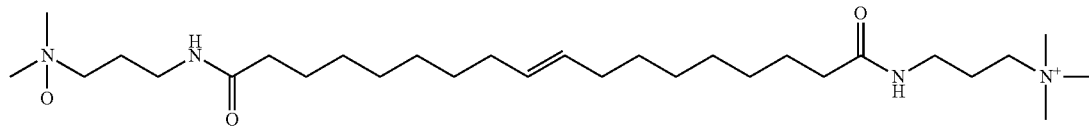

Mix-34 (186.9 g) is dissolved in deionized water (200 g) and stripped of isopropyl alcohol at 75° C. The concentrate (321.6 g) is transferred to a round-bottom flask and Hamp-Ex 80 (0.53 g) is added. The mixture is heated to 50° C. and a few pieces of dry ice are added until the mixture pH is 8-9. Aqueous $H_2O_2$ (35%, 18.23 g) is then added dropwise, maintaining temperature below 70° C. After peroxide addition is complete, the mixture is maintained at 85° C. for 16 h. Deionized water (75 g) is added. The mixture cools to room temperature. $^1$H NMR analysis is consistent with the proposed structure for quat amine oxide Mix-35 and shows no detectable free amine. Other analyses show: free peroxide: 0.002%; water: 59.2%.

C18-36: C18 DiDMAPA MonoBetaine (100% trans-)

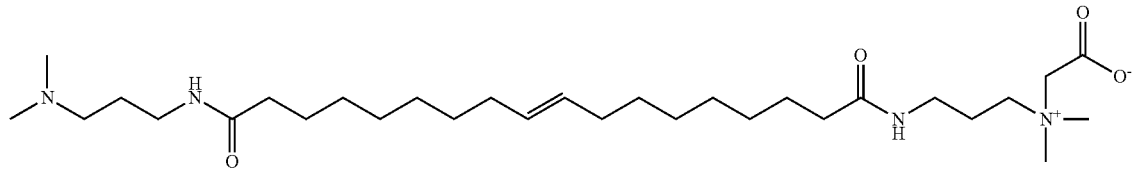 [SMILES: CN(C)CCCNC(=O)CCCCCCC/C=C/CCCCCCCC(=O)NCCC[N+](C)(C)CC(=O)[O-]]

Amidoamine C18-26 (348 g) and deionized water (500 g) are charged to a round-bottom flask. The mixture is heated to 80° C. and citric acid (2.5 g) is added. A solution made from sodium monochloroacetate (SMCA, 88.5 g) and deionized water (300 g) is added dropwise to the amidoamine solution over 1 h. After the addition is complete, the mixture is heated to 85° C. for 3 h and then 95° C. for 0.5 h. The mixture is then cooled to room temperature. Analysis by silver nitrate titration indicates 3.49% NaCl. Additional SMCA (1.5 g) is added and the mixture is reheated to 95° C. for 6 h. After 6 h, the NaCl content is 3.53%. $^1$H NMR analysis of a dried aliquot of product shows 45.7% free amine and 54.3% quaternized amine, based on the integration of the methyl group signals at 2.28 and 3.22 ppm, respectively.

MIX-36: C18 DiDMAPA MonoBetaine (80:20 trans-/cis-)

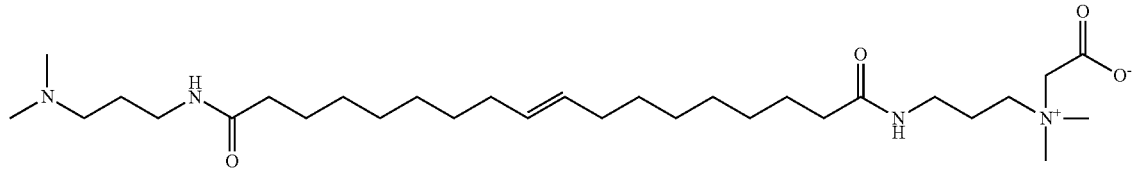 [SMILES: CN(C)CCCNC(=O)CCCCCCC/C=C/CCCCCCCC(=O)NCCC[N+](C)(C)CC(=O)[O-]]

The procedure used to make C18-36 is generally followed with amidoamine Mix-26 (224.5 g), deionized water (322 g), citric acid (1.5 g), and aqueous sodium monochloroacetate (57 g of SMCA in 200 g of DI water). After the SMCA addition is complete, the mixture is heated to 90° C. for 2 h. Additional SMCA (3.5 g) is added and the mixture is maintained at 90° C. for 2 h. NaCl content: 3.82%. $^1$H NMR analysis of a dried aliquot shows 44% free amine and 56% quaternized amine.

C18-37: C18 DiDMAPA Betaine AO (100% trans-)

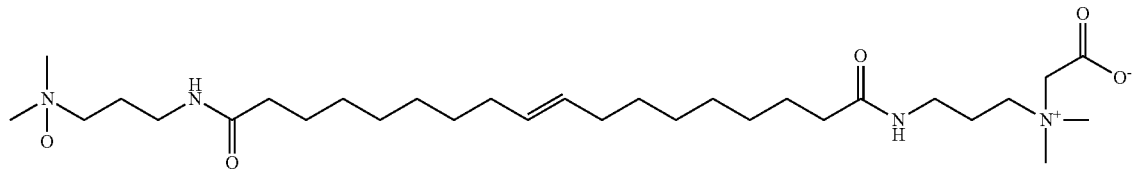

Molten monobetaine C18-36 (35% solids, 415.2 g) is charged to a flask and heated to 70° C. Aqueous $H_2O_2$ (35%, 23.6 g) is added dropwise over 0.5 h, maintaining reaction temperature below 78° C. After the peroxide addition is complete, the mixture is stirred at 70° C. for 9 h. $^1$H NMR ($CD_3OD$) of a dried aliquot indicates complete conversion of the monobetaine to the expected amine oxide. Evidence is the disappearance of the $N(CH_3)_2$ peak at 2.28 ppm for the amine and appearance of a peak at 3.15 ppm for the amine oxide $N(CH_3)_2$.

MIX-37: C18 DiDMAPA Betaine AO (80:20 trans-/cis-)

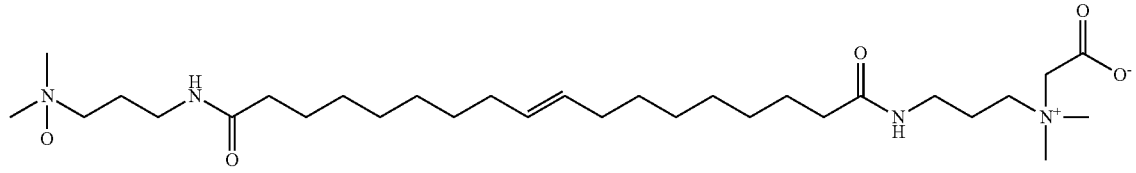

Monobetaine Mix-36 (35% solids, 470 g) is charged to a flask and heated to 60° C. Aqueous $H_2O_2$ (35%, 27.6 g) is added dropwise over 0.5 h, maintaining the temperature at 70° C. After the addition is complete, the mixture is stirred at 70° C. for 3 h. A small quantity of partially dried monobetaine (Mix-36) is added to react with excess peroxide. The mixture is maintained at 70° C. for 5 h. Free peroxide by titration: 0.18%. $^1$H NMR ($CD_3OD$) of a dried aliquot indicates complete conversion of the monobetaine to the expected amine oxide product. Integration of the amine oxide and betaine $N(CH_3)_2$ peaks indicates shows: betaine: 53.4 mol %; amine oxide: 46.6 mol %.

C18-38: C18 DiDMAPA Betaine Quat (100% trans-)

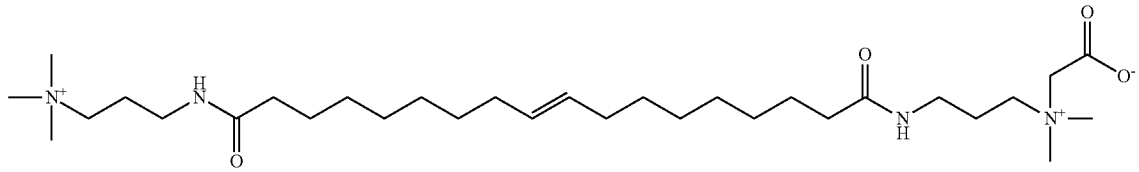 [SMILES: C[N+](C)(C)CCCNC(=O)CCCCCCC/C=C/CCCCCCCC(=O)NCCC[N+](C)(C)CC(=O)[O-]]

A nitrogen-purged flask is charged with monobetaine C18-36 (138.9 g), isopropyl alcohol (40 g), and ethanol (42.5 g). The mixture is warmed to 70° C. and dimethyl sulfate (21.77 g) is added dropwise. The mixture is cooled to maintain the temperature ~70° C. The mixture is held at 70° C. for 6 h, then at 85° C. for 2 h. The mixture is allowed to cool and is concentrated. Water is added to adjust the solids content to ~50 wt. %. Analysis of the product, C18-38, shows: pH: 7.59; NaCl: 1.09 wt. %; IPA: 0.49 wt. %; EtOH: 0.78 wt. %; moisture: 48.9 wt. %.

MIX-38: C18 DiDMAPA Betaine Quat (80:20 trans-/cis-)

a waxy, crystalline solid upon cooling (655 g, ~70% yield). Analysis of the product (following derivatization) by gas chromatography shows that it contains 94% acid/ester and 6% diacid. Quantitative $^{13}$C NMR shows an 86:14 trans:cis isomer ratio.

MIX-43: C18 Ester/DMAPA Amide (80:20 trans-/cis-)

The mixed acid/ester Mix-69 is converted to the acid chloride/ester by reaction with a slight excess of thionyl chloride (SOCl$_2$) in methylene chloride solution and the product is isolated by removal of the solvent and excess SOCl$_2$ under reduced pressure. $^1$H NMR analysis of the isolated product

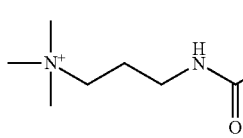
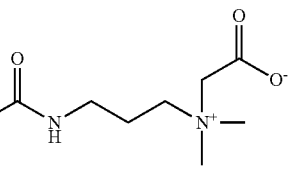

A nitrogen-purged flask is charged with monobetaine Mix-36 (113.9 g), isopropyl alcohol (66 g), and ethanol (30 g). The mixture is warmed to 70° C. and dimethyl sulfate (15.65 g) is added dropwise. The mixture is cooled to maintain the temperature ~70° C. The mixture is held at 70° C. for 3 h. Additional dimethyl sulfate (0.96 g) is added, and heating continues at 70° C. for 3 h, then at 85° C. for 2 h. The mixture is allowed to cool and is concentrated. Water (195 g) is added to ~40 wt. % solids. Analysis of the betaine quat product, Mix-38, shows: pH: 8.35 (1% in water); moisture: 47.7 wt. %; NaCl: 4.74 wt. %; sodium sulfate: 0.3 wt. %. $^1$H NMR data support the proposed structure.

MIX-69: C18 Ester/Acid (80:20 trans-/cis-)

shows essentially quantitative conversion to the acid chloride/ester, and the material is used without further purification.

A 3-L reaction vessel equipped with mechanical stirrer, nitrogen inlet, and thermocouple is charged with methylene chloride (200 mL), DMAPA (172.1 g), and pyridine (133.3 g). The previously prepared acid chloride/ester is added dropwise to the stirred DMAPA-pyridine solution. During the addition, the temperature is maintained at 25-40° C. by cooling with an ice bath as required, and the addition is completed in 1.5 h. A precipitate forms, and after stirring overnight at room temperature, the mixture has become a thick slurry. The mixture is diluted with methylene chloride (500 mL), and water (500 mL) is added, giving a clear homogeneous solu-

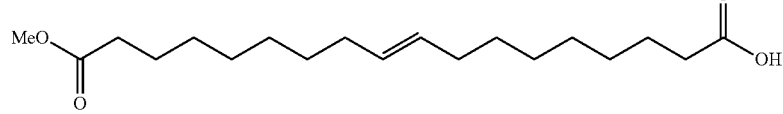

The half-acid/ester Mix-69 is prepared from the dibasic ester Mix-0 (used as received) as described in Organic Syntheses: Col. Vol. IV (1963) 635. Thus, Mix-0 (1 kg) is added to methanol (~9 L) and the mixture is stirred mechanically. In a separate vessel, Ba(OH)$_2$ (274.4 g) is dissolved in methanol (~4 L), and the solution is added in portions over 2 h to the stirred diester solution, resulting in the formation of a white precipitate. The solid is isolated by filtration, washed several times with methanol, and dried in air. The solid is then transferred to a 12-L reaction vessel and slurried in ethyl acetate (~3.5 L). Aqueous HCl (32%, Aldrich, 1248.6 g), is added in portions to the stirred slurry, resulting in dissolution of the solid and formation of a clear solution. The solution is washed three times with water, and the aqueous layers are removed and collected in a separate vessel. The combined aqueous layers are extracted once with ethyl acetate, and the organic phase is combined with the washed product solution. The mixture is dried (Na$_2$SO$_4$), filtered, and concentrated via rotary evaporator. Thorough drying under high vacuum gives tion. Addition of ethyl acetate fails to induce phase separation. However, addition of saturated NaCl solution causes slow separation of a lower aqueous phase, which is drained and discarded. Concentration of the organic phase via rotary evaporation gives a viscous brown oil. $^1$H NMR analysis shows free pyridine and indicates that the terminal tertiary amine of the DMAPA moiety is protonated. The material is taken up in acetone and the mixture is filtered to remove a small quantity of precipitated solid. The pH of the solution is adjusted to ~8.5 (measured on as-is material) with 50% aq. NaOH, resulting in the formation of a solid precipitate. The mixture is filtered again and the clear filtrate is concentrated and then dried under high vacuum. On cooling, the material solidifies. $^1$H NMR analysis is consistent with the target structure and shows the presence of free pyridine. The product is heated to 60° C., stirred, and sparged with sub-surface nitrogen under reduced pressure for 5 h, then at 105° C. for 30 min. After stripping, $^1$H NMR analysis of the product showed no residual pyridine.

MIX-44: C18 Ester DMAPA Quat (80:20 trans-/cis-)

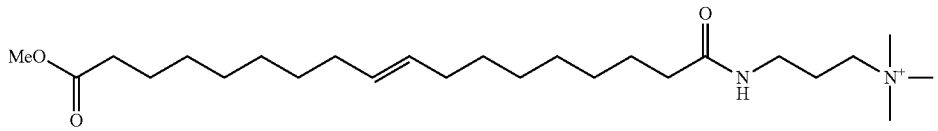 [SMILES: COC(=O)CCCCCCC/C=C/CCCCCCCC(=O)NCCC[N+](C)(C)C]

Ester-amidoamine Mix-43 (162.7 g) is charged to a flask equipped with mechanical stirring, thermocouple, and nitrogen inlet. Isopropanol (IPA; 47.8 g) is added, and the mixture is heated to 70° C. Perchloric acid titration of the ester/amide starting material is used to calculate the required amount of dimethylsulfate (DMS). The DMS (28.6 g) is added dropwise while maintaining the reaction temperature at 70° C. with external cooling. After the DMS addition is complete, the mixture is stirred at 70° C. for 3 h, then for 1 h at 85° C. Perchloric acid titration shows nearly complete consumption of the tertiary amine. The quat product, Mix-44, cools to give a waxy solid. Analysis for residual DMS via Drager apparatus is negative.

MIX-48: C18 Ester DMAPA Betaine (80:20 trans-/cis-)

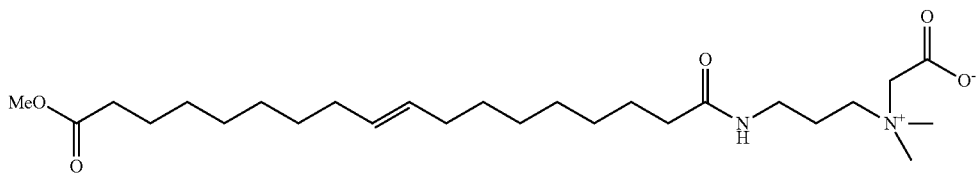 [SMILES: COC(=O)CCCCCCC/C=C/CCCCCCCC(=O)NCCC[N+](C)(C)CC(=O)[O-]]

A round-bottom flask fitted with a thermocouple, nitrogen inlet, and mechanical stirring is charged with ester-amidoamine Mix-43 (134.2 g, 0.327 mol). Water (250 mL) and sodium monochloroacetate (38.9 g, 0.334 mol) are added. The mixture is warmed to 70° C. and after approximately 1 h, it becomes clear. During the reaction, the pH of the mixture is maintained at ~8 with 50% aq. NaOH. Heating continues for 5 h at 70° C. The $^1$H NMR spectrum is consistent with the proposed structure and shows no residual tertiary amine. The product, ester-betaine Mix-48, is cooled and analyzed: water: 59.9%; NaCl: 4.29%.

C18-65: C18 DiDMAPA Benzyl Quat (100% trans-)

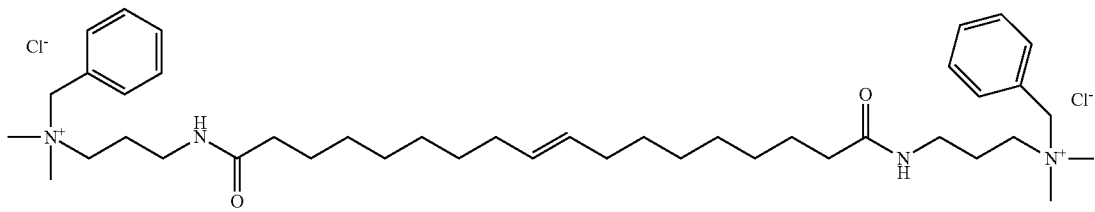

Bis(amidoamine) C18-26 (100 g) and methanol (67 g) are charged to a flask equipped with thermocouple, mechanical stirring, reflux condenser, and nitrogen inlet. The mixture is heated to 67° C. and benzyl chloride (44 gI is added dropwise while the temperature is allowed to rise to 82° C. During heat-up, the reflux condenser is replaced with a distillation side-arm and refluxing methanol distills from the mixture until the temperature reaches 82° C. The side-arm is replaced with a reflux condenser and the mixture stirs for 2 h at 82° C. Sodium hydroxide (50% aq., 0.33 g) is added, followed by more benzyl chloride (9 g), and the mixture is held at 82° C. for 2 h. The mixture is cooled to 50° C. and poured into water (67 g). After stirring for 5 min., the bis(benzyl quat) solution is analyzed: methanol: 16.4%; free tertiary amine: none detected; water: 26.8%; quat actives: 58.7%. $^1$H NMR spectrum is consistent with the target structure.

MIX-65: C18 DiDMAPA Benzyl Quat (80:20 trans-/cis-)

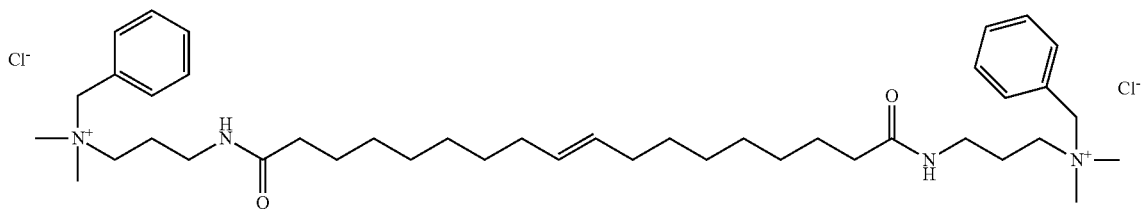

A round-bottom flask equipped with a stir bar, reflux condenser, and thermocouple is charged with bis(amidoamine) C18-26 (118.4 g) and methanol (44 g). The mixture is heated to 67° C. and benzyl chloride (50 g) is added dropwise. The addition rate is adjusted to maintain temperature below 95° C. After the benzyl chloride is added, the temperature was adjusted to 82° C. and held for 2 h. More methanol (21 g) is added to reduce viscosity. Sodium hydroxide (50% aq.; 0.33 g) is added, followed by more benzyl chloride (11.2 g), and the mixture is held at 82° C. for 2 h. $^1$H NMR analysis is consistent with the target structure and shows no residual tertiary amine. The hot benzyl quat is added to deionized water (140 g) with good agitation, and the mixture is allowed to cool. Analysis of the bis(benzyl quat), Mix-65, shows: MeOH: 10.8%; water: 39.7%; free tertiary amine: 0.027 meq/g; quat actives: 49.1%.

Modified Triglyceride Based on Soybean Oil ("MTG-0")

The procedures of Examples 1A and 1E are generally followed except that 1-butene is omitted.

Mod. Triglyceride from Cross-Metathesis of Soybean Oil and 1-Butene ("UTG-0")

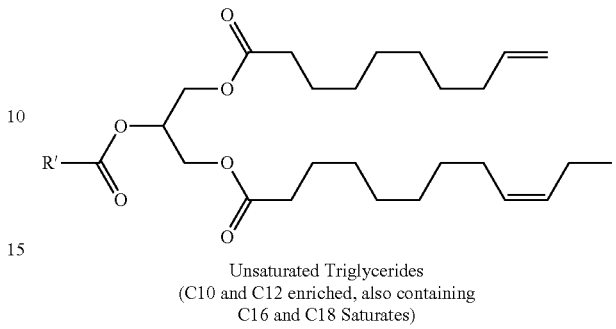

Unsaturated Triglycerides
(C10 and C12 enriched, also containing
C16 and C18 Saturates)

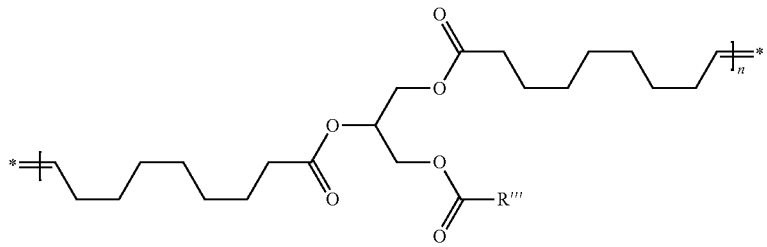

The procedures of Examples 1A and 1E are generally followed to produce UTG-0 from soybean oil and 1-butene.
Modified Triglyceride Based on Palm Oil ("PMTG-0")

The procedure used to make UTG-0 is followed, except that palm oil is used instead of soybean oil.
MTG-0 Feedstock Derivatives

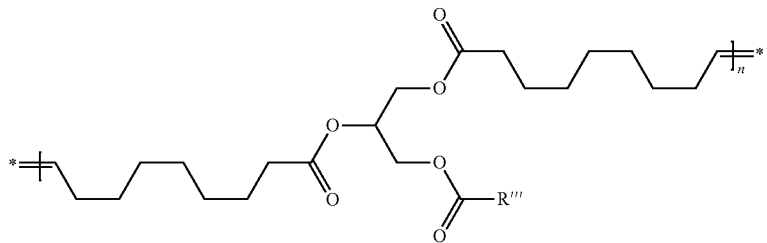

The procedure used to make MTG-0 is followed, except that palm oil is used instead of soybean oil.
Mod. Triglyceride From Cross-Metathesis of Palm Oil and 1-Butene ("PUTG-0")

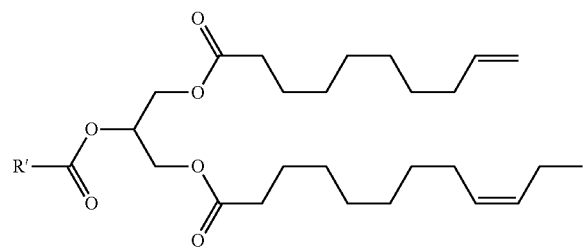

Unsaturated Triglycerides
(C10 and C12 enriched, also containing C16 and C18 Saturates)

TABLE 3

Summary of Modified Triglyceride Products

|  | Soybean Oil | | Palm Oil | |
| --- | --- | --- | --- | --- |
|  | Self-met. | X-met. | Self-met. | X-met. |
|  | MTG-0 | UTG-0 | PMTG-0 | PUTG-0 |
| DMAPA Betaine | MTG-6 | UTG-6 | PMTG-6 | PUTG-6 |
| DMAPA Sulfobetaine | MTG-11 | UTG-11 | PMTG-11 | PUTG-11 |
| DMAPA DMS Quat | MTG-13 | UTG-13 | PMTG-13 | PUTG-13 |
| DMAPA Benzyl Quat | MTG-14 | UTG-14 | PMTG-14 | PUTG-14 |

DMAPA = N,N-dimethyl-1,3-propanediamine.

Detailed procedures appear below for preparation of the MTG and PUTG products starting from MTG-0 or PUTG-0. The PMTG products have analogous structures to the MTG products. The UTG products have structures analogous to the PUTG products.

MTG-5: MTG DMAPA Amide Mix

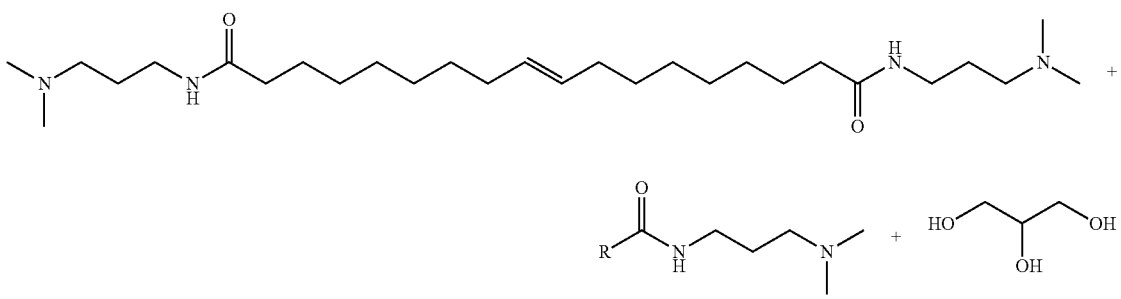

R = C16, C18 Sat. + Unsat.

A round-bottom flask is charged with MTG-0 (180 g, saponification value=226.5 mg KOH/g, 0.73 mol), and the contents are heated to 50° C. The mixture is purged with nitrogen for 1 h and dimethylaminopropylamine (DMAPA, 78 g, 0.76 mol) and NaBH$_4$ (0.1 g) are added. The mixture is heated to 160° C. for 18 h. Excess amine is removed by short-path distillation (135° C., 30 mm Hg), and the product is cooled to room temperature to afford amidoamine mixture MTG-5. Amine value: 172.9 mg KOH/g (eq. wt.: 324.45 g/mol). Free DMAPA: 1.80%; iodine value: 71.9 g I$_2$/100 g sample.

MTG-6: MTG DMAPA Betaine Mix

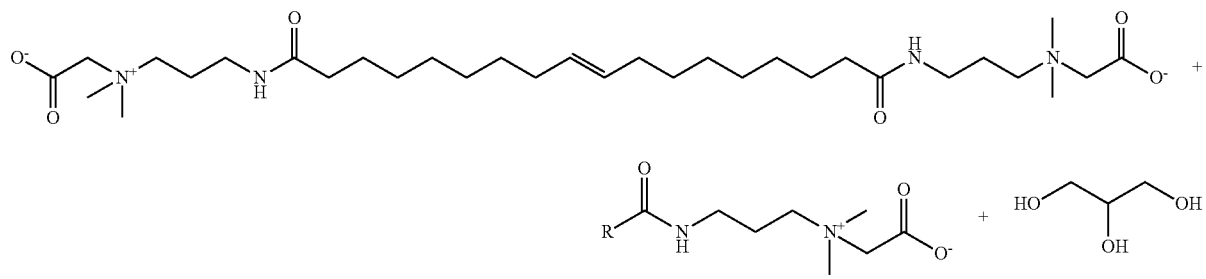

R = C16, C18 Sat. + Unsat.

A round-bottom flask is charged with MTG-5 (107.8 g, 0.32 mol), sodium monochloroacetate (SMCA, 38.4 g, 0.33 mol), and water (237 g). The mixture is heated to 80° C. for 1 h, and the mixture becomes homogeneous. The pH is maintained between 8.5-10 (measured as 10% dilution in IPA and/or water) using 50% aq. NaOH. After the pH stabilizes, the mixture is heated to 100° C. for 14 h. When the NaCl level stabilizes, the reaction is judged complete. The product is cooled to room temperature, and the pH is adjusted to 8.5. The betaine product, MTG-6, is a clear, homogeneous solution. NaCl content: 5.22%; solids: 39.4%; betaine actives: 34.2%.

MTG-11: MTG DMAPA Sulfobetaine

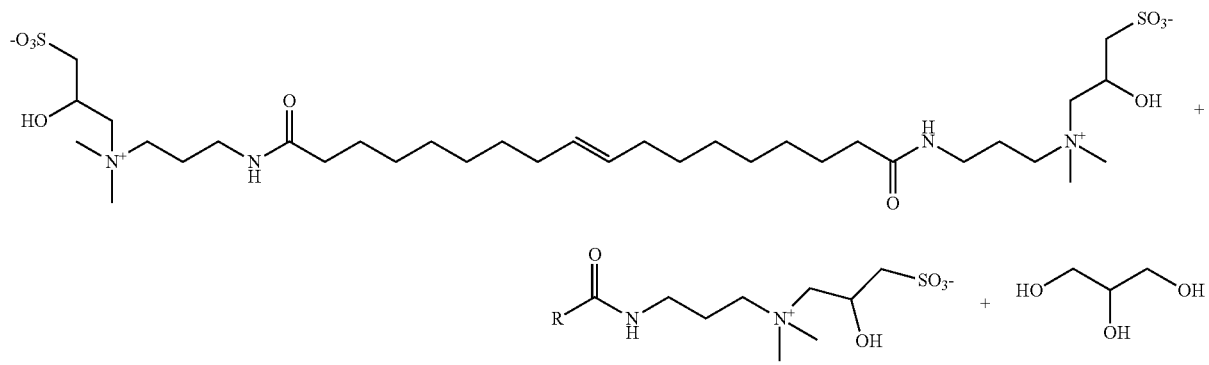

R = C16, C18 Sat. + Unsat.

A nitrogen-purged flask is charged with sodium metabisulfite (46.4 g) and water (250 g), and the mixture is warmed to 40° C. Aqueous NaOH (0.75 g of 50% solution) is added and stirred briefly. Epichlorohydrin (44.3 g) is added dropwise over 1 h allowing the mixture to warm to 70° C. The mixture stirs at 70° C. for 0.5 h and more 50% NaOH (0.75 g) is added. After briefly mixing, MTG-5 (150 g) is added in one portion. The mixture is held at 80° C. and stirred for 3 h. The pH is adjusted in the usual way from 8.2 to 10.3. After 3 h, the mixture cools to room temperature. The mixture is reheated to 80° C. and stirred for 1 h. With pH=10.35 and NaCl content=6.81%, the reaction is judged complete. The product cools to room temperature and the pH is adjusted to 8.60 with 50% aq. H$_2$SO$_4$. Analysis of the sulfobetaine, MTG-11, shows: NaCl: 5.65 wt. %; moisture: 49.7%; solids: 50.3%; sulfobetaine actives (by solids-NaCl): 44.7%. $^1$H NMR analysis of a dried aliquot supports the proposed structure.

MTG-13: MTG DMAPA DMS Quat

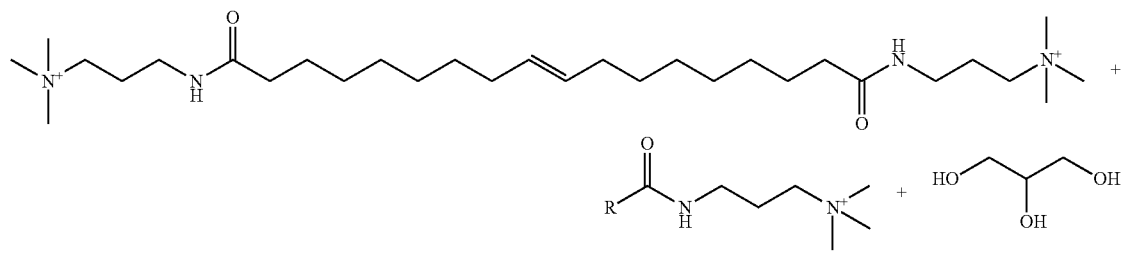

R = C16, C18 Sat. + Unsat.

A nitrogen-purged flask is charged with MTG-5 (159.9 g) and the contents are warmed to 80° C. Dimethyl sulfate (56.86 g) is added. The mixture is warmed to 95° C., but viscosity remains high, so temperature is reduced to 70° C. and isopropyl alcohol (25.5 g) is added. The reaction stirs for 3 h at 70° C. and is allowed to cool. Analysis of the quat product, MTG-13, shows: free amine: 0.055 meq/g; moisture: 0.13 wt. %; active quat: 1.80 meq/g.

MTG-14: MTG DMAPA Benzyl Quat

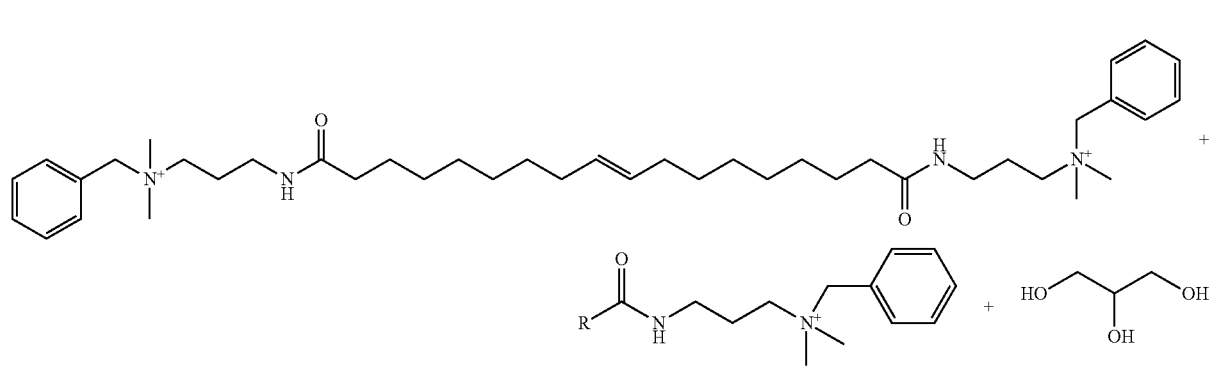

R = C16, C18 Sat. + Unsat.

A round-bottom flask equipped with stir bar, reflux condenser, and thermocouple, is charged with MTG-5 (118.4 g) and methanol (23 g). The mixture is heated to 67° C. and benzyl chloride (39.3 g) is added dropwise. The addition rate is adjusted to keep the temperature below 95° C. After the addition, the temperature is adjusted to 82° C. and held for 2 h. Aqueous sodium hydroxide (0.33 g of 50% solution) is added followed by more benzyl chloride (6.9 g), and the mixture is held at 82° C. for 2 h. $^1$H NMR shows the desired product. The hot benzyl quat is added to water (140 g) and the mixture cools to room temperature while stirring. The benzyl quat product, MTG-14 (300 g), is analyzed: pH: 6.7 (1% in 9:1 in IPA/water); free amine: 0.011 meq/g; moisture: 42.9 wt. %; active quat: 1.06 meq/g; tertiary amine: 0.023 meq/g.

PUTG-5: PUTG DMAPA Amide Mix

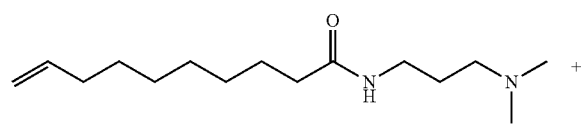

-continued

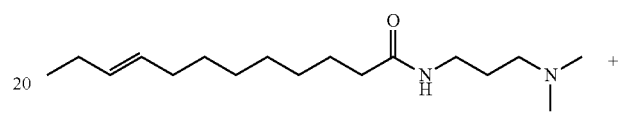

-continued

R = C16, C18 Sat.

Molten PUTG-0 (750 g, saponification value: 227.6 mg KOH/g, 3.04 mol) is charged to a reaction vessel equipped with a reflux condenser, thermocouple, nitrogen/vacuum take-off, and mechanical agitator. The mixture is stirred at 60° C. under nitrogen. Sodium borohydride (0.4 g) is added, and the mixture is stirred for 0.5 h. The mixture is degassed under full vacuum (0.5 h). The vacuum is released with nitrogen and dimethylaminopropylamine (DMAPA, 325 g, 3.18 mol) is then added. The temperature is increased until a gentle reflux of DMAPA occurs (~150° C.). The mixture is held at 150° C. until reflux slows. The temperature is then increased to 160° C. Stirring continues for 4 h at 160° C., and then the mixture is stirred overnight at 150° C. The mixture is cooled to 100° C. and excess DMAPA is removed using a gentle vacuum and dry-ice trap. Vacuum is slowly improved until full vacuum is reached. Stripping continues for 1 h. The waxy product, PUTG-5, is titrated with HCl. Acid value: 160.6 meq/g; eq. wt.: 349.4 g/mol. Amine value: 160.56 mg KOH/g; % free DMAPA: 0.08%. $^1$H NMR (CDCl$_3$), δ: 5.8 (CH$_2$=CH—);

5.4 (—CH═CH—); 4.9 (CH$_2$═CH—); 3.2 (—C(O)—NH—CH$_2$—); 2.15 (—N(CH$_3$)$_2$).

PUTG-6: PUTG DMAPA Betaine Mix

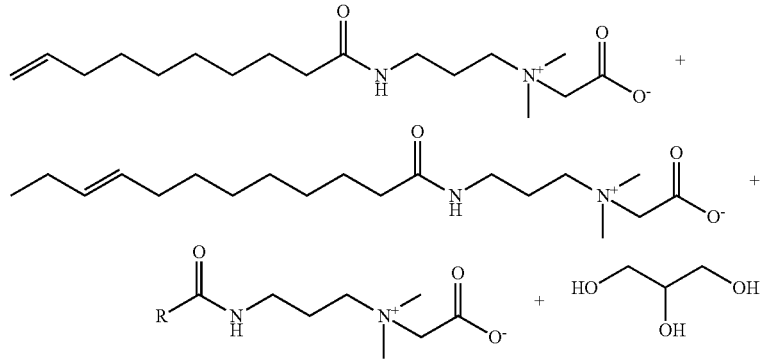

R = C16, C18 Sat.

Molten PUTG-5 (200 g, 0.57 mol) is charged to a reaction vessel, warmed to 50° C., and stirred mechanically while flushing the vessel with nitrogen for 0.5 h. A solution prepared from sodium monochloroacetate (SMCA, 0.58 mol, 68 g) and water (498 g) is added to the molten amine, and the temperature is increased to 70° C. The initially hazy mixture becomes clear and homogeneous. The pH is maintained at 8.5-10 (measured as 10% aqueous dilution) by adding 50% aqueous NaOH as required throughout the reaction. The mixture is also analyzed for NaCl periodically to judge reaction completion. After 4 h, the temperature is increased to 80° C. and held for 2 h before cooling to room temperature overnight. NaCl content: 4.21% (theoretical NaCl based on 100% conversion: 4.45%). The mixture is reheated to 80° C. Free amine (by titration): 0.43%. An additional charge of SMCA (1.10 g) is added, and stirring continues for 2 h at 80° C. Measured pH: 8.78; NaCl content: 4.35%. The reaction is judged complete and the product, PUTG-6, is cooled to room temperature. $^1$H NMR analysis of isolated solids is consistent with the target structure. The final pH is adjusted to 7.5 by adding 50% H$_2$SO$_4$ (1 g), giving the product as a clear aqueous solution. Solids content: 35.8%; free amine: 0.85%; NaCl: 4.39%.

PUTG-11: PUTG DMAPA Sulfobetaine

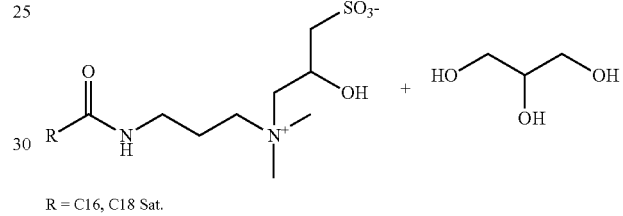

-continued

R = C16, C18 Sat.

The procedure used to make MTG-11 is generally followed with PUTG-5 (200 g), sodium metabisulfite (61.1 g), water (330.8 g), 50% aqueous NaOH (two 1.0-g portions), and epichlorohydrin (58.3 g). After the mixture cools to room temperature, additional water (10 g) is added to the waxy gel, and the mixture is reheated to 80° C. for 2.5 h. Again, the pH is kept between 8.4 and 9.2 with aqueous NaOH as required. When the NaCl level stabilizes at 5.49%, the reaction is judged complete. After cooling to room temperature, the thick product is warmed to 40° C. and water (15 g) is added. The pH is adjusted to 6.52 by adding 50% H$_2$SO$_4$ (aq.). On cooling the product again becomes a thick gel, requiring further dilution. Additional water was added to give an approximately 50% solids solution. The product, PUTG-11, is analyzed: NaCl: 5.29 wt. %; moisture: 51.2%; solids: 48.8%; sulfobetaine actives (by solids-NaCl): 43.5%. $^1$H NMR analysis of a dried aliquot supports the proposed structure.

PUTG-13: PUTG DMAPA DMS Quat

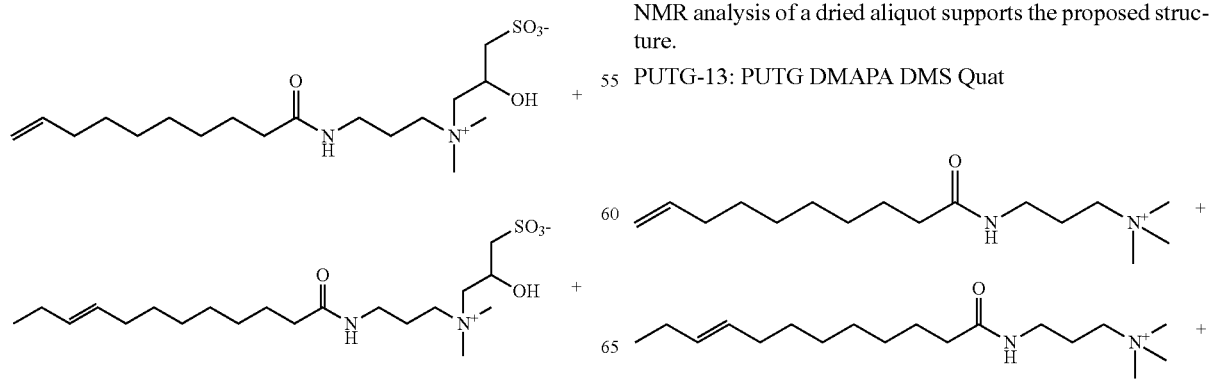

-continued

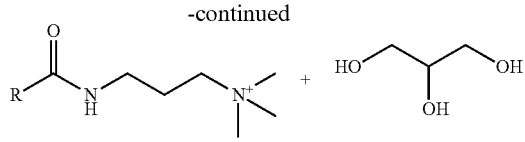

R = C16, C18 Sat.

A nitrogen-purged flask is charged with PUTG-5 (113.3 g) and the contents are warmed to 80° C. Dimethyl sulfate (40.23 g) is added. The mixture is warmed to 95° C. for 1 h. Viscosity remains high, and isopropyl alcohol (~20 g) is added. The mixture stirs for 1 h and then cools to room temperature. Analysis of the quat product, PUTG-13, shows: pH: 7.47 (1% in 9:1 2-propanol/water); iodine value: 21.55, free amine: 0.053 meq/g: moisture: 0.29 wt. %.

PUTG-14: PUTG DMAPA Benzyl Quat

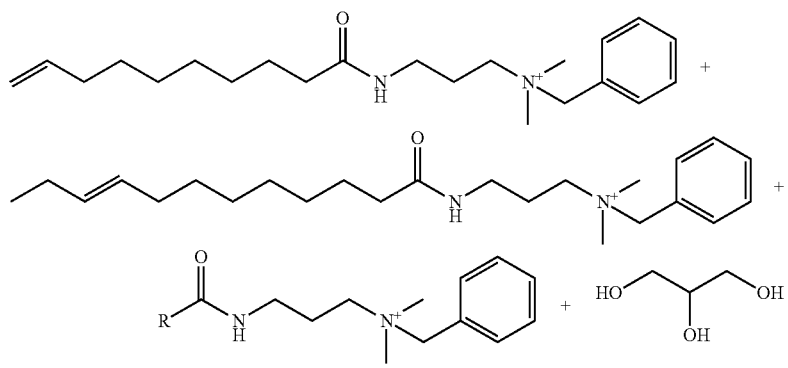

R = C16, C18 Sat.

A round-bottom flask equipped with stir bar, reflux condenser, and thermocouple, is charged with PUTG-5 (110 g) and methanol (21 g). The mixture is heated to 67° C. and benzyl chloride (34.4 g) is added dropwise. The addition rate is adjusted to keep the temperature below 95° C. After the addition, the temperature is adjusted to 82° C. and held for 2 h. Aqueous sodium hydroxide (0.30 g of 50% solution) is added followed by more benzyl chloride (5.5 g), and the mixture is held at 82° C. for 2 h. $^1$H NMR shows the desired product. A gel forms, and the mixture is rewarmed to 80° C. Water is added to give a clear solution, which is analyzed. The benzyl quat product, PUTG-14 (248 g), is analyzed: iodine value: 10.22; pH: 9.15 (1% in 9:1 2-propanol/water); NaCl: 7.12 wt. %; moisture: 32.1 wt. %; tertiary amine: 0.22 wt. %; actives (alkyl quats): 1.23 meq/g.

Agricultural Glyphosate Formulations: Formulation Stability

Sample Preparation:

A 44.0% acid equivalent (a.e.) formulation is prepared by first charging glyphosate acid (486.19 g, 90.5% a.e., product of Monsanto) to an ice-cooled 1-L reaction vessel equipped with a mixer and temperature probe. Deionized water (337.23 g) is added with mixing to generate a glyphosate acid slurry. Potassium hydroxide pellets (176.58 g, 86.6% KOH, Fisher) are slowly added such that the temperature of the solution does not exceed 50° C. The mixture is then allowed to cool to room temperature and is mixed until a clear glyphosate concentrate of 44% a.e. results. The pH of the concentrate is measured by preparing a 10% solution of the concentrate in deionized water and measuring it with a pH electrode. If the pH of the concentrate is between 4.2 and 4.4 the concentrate is used as is. If the pH needs to be adjusted, then glyphosate acid, KOH, and water are added in appropriate quantities to yield the correct pH while maintaining the 44% a.e. level of the concentrate required.

Stability Testing:

A test surfactant (5.0 g) is added to 45.0 g of the glyphosate concentrate above (44% a.e.) to yield a glyphosate formulation concentrate, ~39.6% a.e. (~540 g/L a.e. K salt). This concentrate is mixed until a clear solution results. If no clear solution results, an aliquot of lauryl dimethyl amine oxide (LDMAO, ~55-60% actives) is added to the surfactant to make a 90:10 surfactant:LDMAO blend. This is then tested for stability as above. If that does not pass, the procedure of adding LDMAO to the surfactant continues until a ratio is found that gives a stable glyphosate formulation. If no stable formulation can be made, the surfactant is deemed incompatible with glyphosate. If a clear homogeneous solution results, the sample is split in two and placed both in a 54° C. oven and a −10° C. freezer for two weeks. If there is no haziness or separation, the formulation is considered stable at that temperature.

The control surfactant is a $C_{12}$-$C_{14}$ DMEA esterquat. This is prepared by reacting a mixture of lauric ($0_{12}$) and myristic ($0_{14}$) acids with N,N-dimethylethanolamine (DMEA) at 140° C. for 5 h, then heating to 175° C. to complete the reaction. Quaternization with methyl chloride in propylene glycol at 80° C. at 40 psig in the usual way provides the desired esterquat. The control surfactant gives a clear formulation at room temperature but the formualation separates at −10C. Addition of amine oxide in a 9:1 to 1:1 ratio (control surfactant to amine oxide) is needed to give a desirable stability with the control.

As shown in Table 4, twenty-two samples performed as well as or better than similar compounds in the stability testing.

TABLE 4

Glyphosate Formulation Stability: 540 g.a.e./L K salts

| Sample | AO added | Stable at: | | | Comment | Rating |
| --- | --- | --- | --- | --- | --- | --- |
| | | RT | −10° C. | 54° C. | | |
| C18-35 | N | Y | Y | Y | | superior |
| Mix-35 | N | Y | Y | Y | | superior |
| C18-36 | N | Y | Y | Y | | superior |
| Mix-36 | N | Y | Y | Y | | superior |
| C18-37 | N | Y | Y | Y | | superior |

TABLE 4-continued

Glyphosate Formulation Stability: 540 g.a.e./L K salts

| Sample | AO added | Stable at: RT | -10° C. | 54° C. | Comment | Rating |
|---|---|---|---|---|---|---|
| Mix-44 | N | Y | Y | Y | 5% sample | superior |
| C10-41 | Y | Y | Y | Y | 5% sample | good |
| C10-42 | Y | Y | Y | Y | 5% sample | good |
| C12-18 | Y | Y | Y | Y | 6% sample | good |
| C12-40 | Y | Y | Y | Y | 5% sample | good |
| C12-45 | Y | Y | Y | Y | 5% sample | good |
| C16-13 | Y | Y | Y | Y | 5% sample + propylene glycol | good |
| C16-16 | Y | Y | Y | Y | 5% sample + propylene glycol | good |
| C18-27 | Y | Y | Y | Y | 5% sample | good |
| Mix-27 | Y | Y | Y | Y | 5% sample | good |
| C18-34 | N | Y | Y | Y | 6% sample | good |
| Mix-37 | N | Y | Y | Y | 5% sample | good |
| Mix-38 | Y | Y | Y | Y | 5% sample | good |
| PMTG-13 | N | Y | Y | Y | 60% sol. in propylene glycol passes | good |
| PUTG-13 | Y | Y | Y | Y | 5% sample | good |
| MTG-13 | Y | Y | Y | Y | 6% sample, 2.5% PG, 1.5% AO | good |
| UTG-6 | Y | Y | Y | Y | 5% sample | good |

Water-Soluble Herbicide Formulation Testing

Surfactant candidates for water soluble herbicide applications are examined as a replacement for the anionic, nonionic, or anionic/nonionic blend portion and compared to a known industry standard for use in paraquat, a water soluble herbicide concentrate formulation. A standard dilution test is conducted whereby the concentrates are diluted in water to determine if solubility is complete.

Control: Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h. Results of the solubility testing appear in Table 5 below.

Anionic Test Sample:

Paraquat (4.57 g of 43.8% active material) is added to a 20-mL glass vial. An eight to ten mole alkyl phenol alkoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic Test Sample:

Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample. See Table 5 for solubility results.

Adjuvant (Anionic/Nonionic) Test Sample:

Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample. Criteria for emulsion solubility: Test samples should be as good or better than the control with no separation after one hour. Thirty-three test samples perform as well as or better than the control in the emulsion stability test. Results appear in Table 5.

TABLE 5

Water-Soluble Herbicide Formulation: Emulsion stability, mL separation

| test sample | Anionic sol | 1 h | 24 h | Nonionic sol | 1 h | 24 h | Adjuvant sol | 1 h | 24 h | Rating |
|---|---|---|---|---|---|---|---|---|---|---|
| C10-19 | S | 0 | 0 | D | Tr | 0.5 | S | 0 | 0 | good |
| C10-22 | S | 0 | 0 | D | Tr | 0.5 | S | 0 | 0 | good |
| C10-24 | S | 0 | 0 | D | 0.5 | 0.5 | S | 0 | 0 | good |
| C10-40 | S | 0 | 0 | I | 0.5 | 0.5 | S | 0 | 0 | good |
| C10-41 | S | 0 | 0 | I | MP | MP | S | 0 | 0 | good |
| C10-42 | S | 0 | 0 | I | FL | FL | S | 0 | 0 | good |
| C10-43 | S | 0 | 0 | I | FL | FL | S | 0 | 0 | good |
| C12-22 | S | 0 | 0 | D | 0 | Tr | S | 0 | 0 | good |
| C12-23 | S | 0 | 0 | D | Tr | 0.25 | S | 0 | 0 | good |
| C12-24 | S | 0 | 0 | D | 0.25 | 1 | S | 0 | 0 | good |
| C12-27 | S | 0 | 0 | I | MP | MP | S | 0 | 0 | good |
| C12-40 | S | 0 | 0 | I | >1 | >1 | S | 0 | 0 | good |
| C12-45 | S | 0 | 0 | D | 0 | 0 | S | 0 | 0 | good |
| C12-46 | S | 0 | 0 | I | FL | FL | S | 0 | 0 | good |
| C16-13 | S | 0 | 0.25 | — | — | — | — | — | — | good |
| Mix-27 | S | 0 | 0 | D | 0 | 0 | S | 0 | 0 | good |
| C18-28 | S | 0 | 0 | D | Tr | Tr | S | 0 | 0 | good |
| Mix-31 | S | 0 | 0 | D | 0 | Tr | S | 0 | 0 | good |
| Mix-32 | S | 0 | 0 | D | 0 | Tr | S | 0 | 0 | good |
| C18-33 | S | 0 | 0 | D | 1 | 1 | S | 0 | 0 | good |
| Mix-35 | S | 0 | 0 | I | 5 | 1 | S | 0 | 0 | good |

TABLE 5-continued

Water-Soluble Herbicide Formulation: Emulsion stability, mL separation

| test | Anionic | | | Nonionic | | | Adjuvant | | | |
|------|-----|-----|------|-----|-----|------|-----|-----|------|--------|
| sample | sol | 1 h | 24 h | sol | 1 h | 24 h | sol | 1 h | 24 h | Rating |
| C18-36 | S | 0 | 0 | D | 0 | Tr | D | 0 | 0 | good |
| Mix-36 | S | 0 | 0 | D | 0 | 0 | S | Tr | Tr | good |
| C18-37 | S | 0 | 0 | D | 0 | Tr | S | 0 | 0 | good |
| Mix-37 | S | 0 | Tr | D | 0 | 0 | S | Tr | 0.5 | good |
| Mix-38 | S | Tr | Tr | D | 0 | 0 | S | 0.5 | 0.5 | good |
| Mix-48 | S | 0 | 0 | D | 0 | 0.5 | S | 0 | 0 | good |
| PMTG-6 | S | 0 | 0 | D | 0 | Tr | S | 0 | 0 | good |
| PMTG-11 | S | 0 | 0 | D | 1 | 1.5 | S | 1 | 1 | good |
| MTG-11 | S | 0 | 0 | D | 1 | 1.5 | S | 0 | 0 | good |
| UTG-6 | S | 0 | Tr | D | 0 | Tr | S | 0 | 0 | good |
| UTG-11 | S | 0 | 0 | D | 0.75 | 1 | S | 0 | 0 | good |
| UTG-13 | S | 0 | 0 | D | 0 | 0 | S | 0 | 0 | good |

D = dispersable; S = soluble; I = insoluble; Tr = trace; MP = moderate precipitate; FL = flock
Control result: Solubility: D; 1 h: 0 mL; 24 h: Tr.

Agricultural Products: Anionic Emulsifiers

Anionic surfactant samples contain a relatively high amount of water (>20%) and are prepared as oil-in-water (EW) concentrates. These are tested against controls containing a standard surfactant or a blank. Enough is formulated to test two water hardnesses (34 ppm and 1000 ppm) for each of the three samples.

Sample Preparation:

Pyraflufen (97.8% active, 0.30 g) is combined and with Stepan® C-25 (methyl caprylate/caprate, 7.20 g), and N-methyl-2-pyrrolidone (1.20 g), and the mixture is stirred magnetically until dissolved. In a separate container, Toximul® 8242 (castor oil ethoxylate, POE 40, product of Stepan) 0.96 g), Ninex® MT-630F (fatty acid ethoxylate, POE 30, Stepan, 0.19 g), Ninex® MT-615 (fatty acid ethoxylate, POE 15, Stepan, 0.17 g), Aromatic 150 solvent (ExxonMobil, 0.37 g), and the anionic sample to be tested (0.71 g) are blended. If needed, the anionic sample is melted in an oven at 50-60° C. prior to combining with the other surfactants. When the pyraflufen has dissolved, the entire surfactant blend is added and magnetically stirred until homogeneous. Deionized water (0.90 g) is slowly added with mixing to prevent gelling. Turbidity changes are noted and recorded.

Control 1 Sample:

The same procedure is followed except that the anionic sample is replaced with Ninate® 60 L (calcium alkylbenzenesulfonate, Stepan, 0.71 g).

Control 2 Sample:

No Ninate 60 L (or anionic sample) is included, and the Aromatic 150 amount is increased to 1.08 g.

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type; (4) excellent: thick emulsion cloud reaches the bottom of the cylinder without separation of any type.

Results are provided in Table 6. The four samples indicated below are rated "good" overall as an anionic surfactant.

TABLE 6

Performance as an Anionic Emulsifier: % Separation

| | 34 ppm water | | | 1000 ppm water | | |
|---|---|---|---|---|---|---|
| | Spont. | 1 h | 24 h | Spont. | 1 h | 24 h |
| Control 1 | G | <0.2 C | 1.3 C | G | <0.2 C | 1.3 C |
| Control 2 | F | 4 C | 4.4 C | F | 4 C | 4.4 C |
| C10-19 | F | 3 C | 3 C | F | 3.4 C | 4 C |
| C12-23 | F | 3 C | 3.5 C | F | 3 C | 3 C |
| C18-28 | F− | 4 C | 4.5 C | F− | 3.4 C | 3.9 C |
| C18-33 | F− | 4 C | 4.5 C | F− | 3 C | 3.4 C |

"C" denotes separation in the form of a cream, not a creamy oil or an oil. "Tr" denotes trace of oil observed. "O" denotes oil separated
"Spon." = spontaneity or bloom, rated as E (excellent), G (good), F (fair), P (poor).
Control 1 = native anionic; control 2 = no anionic emulsifier.

Antimicrobial Products: Biocide Actives

Biocidalh efficiency is evaluated using the rapid screen assay, an ATP-based method that measures relative kill % of bacteria in a 5-min. period. The control used is first-generation ADBAC BTC 835 (benzyldimethylammonium chloride). Test organisms: Pseudomonas aeruginosa and Staphylococcus aureas.

Twenty-four hour old test organism cultures are prepared in Mueller Hinton broth and incubated. Samples are accurately weighed in deionized water or 400 ppm water to make a 1000 ppm solution taking into account the actives level of the sample. The 24-h culture is diluted to 10 vol. % to obtain a cell concentration of ~$10^7$ cfu/mL (colony forming units per mL). Reagents are prepared using the instructions provided in the BacTiter-Glo™ Microbial Cell Viability Assay kit (product of Promega) and calibrated at room temperature for 15 min. Each formulation type is dispensed (90 µL at 1000 ppm) into each row of a 96-well plate. Blank medium, i.e., Mueller Hinton broth (10 µL) is dispensed in three replicate wells (1-3) to determine baseline, while the organism to be tested (10 µL) is dispensed in nine experimental replicate wells (4-12). The timer is started, and the test plate (baseline and experimental) is shaken for 30 s. At the end of an appropriate contact time (e.g. 5 min or 10 min), an equal amount of BacTiter-Glo reagent mix is added to each reaction mixture, starting with the experimental samples and ending with the baseline samples. After shaking to ensure thorough mixing, the relative luminescence units (RLUs) of each well are measured and recorded. The % kill of $10^7$ cfu/mL after 5 min. contact time for each organism in DI or hard water is calculated from:

% Kill=[1−(Ave. RLU of Wells$_{Experimental}$−Ave. RLU of Wells$_{Baseline\ Controls}$)]/80000

As shown in Tables 7A and 7B, twenty of the tested compositions perform as well as or better than the control when tested as antimicrobial actives.

TABLE 7A

Performance as Antimicrobial Active
% Kill at 5 min. contact time, $10^7$ cfu/mL, 1000 ppm

|  | Pseudomonas aeruginosa | | Staphylococcus aureas | | Overall |
| --- | --- | --- | --- | --- | --- |
|  | DI water | 400 ppm | DI water | 400 ppm | Rating |
| control | 17.9 | 38.9 | 82.8 | 70.3 |  |
| C10-31 | 47.5 | 47.4 | 79.7 | 65.5 | superior |
| control | 38.4 | 41.5 | 49.0 | 47.1 |  |
| C10-40 | 67.1 | 60.1 | 70.1 | 72.0 | superior |
| control | 25.4 | 19.9 | 32.2 | 35.4 |  |
| C16-17 | 42.6 | 39.4 | 48.1 | 42.5 | superior |
| control | 29.0 | 20.1 | 48.2 | 41.7 |  |
| UTG-14 | 83.0 | 85.5 | 86.2 | 85.2 | superior |
| control | 23.4 | 18.7 | 72.2 | 73.3 |  |
| C10-18 | 29.6 | 28.9 | 75.9 | 71.8 | good |
| control | 23.1 | 35.5 | 49.1 | 47.8 |  |
| C12-18 | 58.7 | 40.5 | 42.4 | 66.3 | good |
| control | 23.1 | 19.7 | 49.1 | 47.8 |  |
| C12-27 | 51.2 | 59.5 | 46.0 | 63.5 | good |
| control | 23.1 | 19.7 | 49.1 | 47.8 |  |
| C12-41 | 48.9 | 49.0 | 42.0 | 61.9 | good |
| control | 41.1 | 26.9 | 48.8 | 43.2 |  |
| C12-45 | 59.3 | 25.7 | 43.0 | 35.2 | good |
| control | 17.9 | 38.9 | 82.8 | 70.3 |  |
| PMTG-14 | 19.9 | 46.7 | 80.4 | 63.0 | good |
| control | 17.9 | 38.9 | 82.8 | 70.3 |  |
| PUTG-14 | 21 | 50 | 80 | 63 | good |
| control | 17.9 | 38.9 | 82.8 | 70.3 |  |
| MTG-14 | 17.4 | 50.0 | 80.4 | 64.3 | good | control = dimethylbenzylammonium chloride

TABLE 7B

Performance as Antimicrobial Active
% Kill at 5 min. contact time, $10^7$ cfu/mL, 1000 ppm

|  | Pseudomonas aeruginosa | | Staphylococcus aureas | | Overall |
| --- | --- | --- | --- | --- | --- |
|  | DI water | 400 ppm | DI water | 400 ppm | Rating |
| control | 38.4 | 26.8 | 61.2 | 35.7 |  |
| C18-27 | 38.9 | 19.8 | 55.4 | 17.7 | good |
| Mix-27 | 52.4 | 23.2 | 56.1 | 23.2 | good |
| Mix-34 | 47.5 | 24.1 | 57.5 | 28.6 | good |
| C18-35 | 29.3 | 34.4 | 55.1 | 35.7 | good |
| Mix-35 | 31.4 | 22.1 | 55.6 | 20.9 | good |
| C18-38 | 42.2 | 18.8 | 57.4 | 30.3 | good |
| C18-65 | 30.4 | 24.7 | 55.6 | 20.6 | good |
| Mix-65 | 30.5 | 26.1 | 55.3 | 22.1 | good | control = dimethylbenzylammonium chloride

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active material).

Nonionic and Amphoteric Test Samples:

A neutral, dilutable all-purpose cleaner is prepared from propylene glycol n-propyl ether (4.0 g), butyl carbitol (4.0 g), sodium citrate (4.0 g), Stepanol WA-Extra PCK (sodium lauryl sulfate, 1.0 g), test sample (0.90 g if 100% active material), and deionized water (to 100.0 g solution). The control sample for nonionic/amphoteric testing replaces the test sample with Bio-Soft EC-690 (ethoxylated alcohol, 1.0 g, nominally 90% active material).

Soil Composition:

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco (1), olive oil (3), linoleic acid (3), and squalene (3).

Thirteen amphoteric (betaine, sulfobetaine) and five anionic (sulfonate) samples perform as well or better than the control in this test (see Tables 8 and 9). Note that quat sulfonates C10-19 and C12-19 are tested as replacements for Bio-Soft EC-690 because their net total charge is zero, although they are listed in Table 9 as "anionic" test samples.

TABLE 8

Control Runs for Gardner Straight Line Washability Test

|  | Ave. % clean after 2, 4, 6, 8, or 10 swipes | | | | |
| --- | --- | --- | --- | --- | --- |
|  | 2 | 4 | 6 | 8 | 10 |
| Control 2 | 47.0 | 57.3 | 61.0 | 63.7 | 65.2 |
| Control 3 | 54.6 | 61.4 | 64.3 | 68.4 | 72.2 |
| Control 4 | 52.5 | 58.2 | 59.5 | 60.9 | 63.3 |
| Control 6 | 51.2 | 57.6 | 62.7 | 62.6 | 66.0 |
| Control 7 | 52.3 | 56.0 | 61.5 | 64.3 | 65.0 |
| Control 8 | 49.6 | 55.9 | 56.8 | 62.8 | 64.1 |
| Control 9 | 55.5 | 61.5 | 66.0 | 65.9 | 68.4 |
| Control 10 | 60.3 | 63.5 | 66.2 | 65.8 | 68.7 |
| Control 11 | 53.0 | 61.0 | 63.6 | 64.6 | 66.2 |
| Control 17 | 54.7 | 63.7 | 64.6 | 66.1 | 69.6 |
| Control 23 | 60.2 | 64.7 | 66.7 | 68.3 | 68.7 |

TABLE 9

Gardner Straight-Line Washability
Nonionic/Amphoteric Test Samples

| Sample | Con. # | Compound class | Ave. % clean 2 | 4 | 6 | 8 | 10 | Rating |
|---|---|---|---|---|---|---|---|---|
| C12-24 | 3 | DMAPA sulfobetaine | 64.2 | 70.6 | 72.3 | 76.6 | 80.2 | superior |
| UTG-11 | 4 | DMAPA sulfobetaine | 63.3 | 65.3 | 69.1 | 69.9 | 70.5 | superior |
| C10-41 | 6 | betaine | 56.2 | 63.0 | 63.1 | 63.7 | 64.2 | equal |
| C10-43 | 23 | sulfobetaine | 55.5 | 63.2 | 66.0 | 66.5 | 67.2 | equal |
| C12-46 | 23 | sulfobetaine | 56.6 | 61.2 | 63.5 | 64.6 | 65.3 | equal |
| Mix-32 | 11 | diDMAPA dibetaine | 49.6 | 58.1 | 59.4 | 62.1 | 65.5 | equal |
| C18-36 | 8 | diDMAPA monobetaine | 50.2 | 57.3 | 59.9 | 65.5 | 67.8 | equal |
| Mix-36 | 11 | diDMAPA monobetaine | 40.1 | 53.7 | 58.4 | 60.4 | 63.6 | equal |
| C18-37 | 8 | diDMAPA betaine/AO | 54.2 | 60.1 | 62.4 | 63.9 | 66.6 | equal |
| PUTG-11 | 7 | DMAPA sulfobetaine | 53.9 | 60.5 | 62.2 | 66.4 | 67.1 | equal |
| UTG-6 | 11 | DMAPA betaine | 51.9 | 60.1 | 61.9 | 62.8 | 63.3 | equal |
| MTG-6 | 10 | DMAPA betaine | 62.8 | 66.7 | 68.7 | 70.2 | 72.7 | equal |
| MTG-11 | 7 | DMAPA sulfobetaine | 49.9 | 54.5 | 54.7 | 58.8 | 61.2 | equal |
| Anionic Test Samples | | | | | | | | |
| C10-19 | 2 | DMAPA quat sulfonate | 55.2 | 62.0 | 65.5 | 66.9 | 67.8 | superior |
| C12-23 | 2 | DMAPA betaine sulfonate | 55.7 | 61.5 | 64.8 | 67.4 | 70.1 | superior |
| C12-19 | 9 | DMAPA quat sulfonate | 55.5 | 61.7 | 64.5 | 66.1 | 66.6 | equal |
| C18-28 | 17 | DMAPA diquat sulfonate | 52.2 | 61.1 | 64.3 | 67.6 | 69.2 | equal |
| C18-33 | 17 | dibetaine sulfonate | 58.7 | 63.3 | 66.2 | 67.6 | 68.1 | equal |

Hard-Surface Cleaners: Foaming Glass and Window Cleaner

Control: Ammonyx® LO (lauramine oxide, 0.70 g, product of Stepan, nominally 30% active) and Bio-Terge® PAS-8S (2.00 g, sodium caprylyl sulfonate, product of Stepan, nominally 38% active) are combined with isopropyl alcohol (2.50 g) and diluted to 100 mL with deionized water.

Test formulation: Test sample (0.21 g if 100% active material) and Bio-Terge PAS-8S (2.00 g) are combined with isopropyl alcohol (2.50 g) and diluted to 100 mL with deionized water.

Method: The test formulation is evaluated for clarity; only clear formulations are evaluated in the low film/low streak test. The test measures the ability of the cleaner to leave a streak and film-free surface on a test mirror. The test formula is applied to a mirror in a controlled quantity and wiped with a standard substrate back and forth, leaving the spread product to dry. Once dry, the mirrors are inspected and evaluated by a two-person panel. Ratings of "better than," "equal" or "worse than" the control are assigned. The formulation used here is used to evaluate amphoteric and nonionic surfactants.

Eight samples, C16-13, C16-16, MTG-6, MTG-11, PMTG-6, PMTG-11, PUTG-6, and PUTG-11, perform equal to the control in the test.

Cold-Water Cleaning Performance of Compaction Laundry Detergents

This method evaluates the overall cold-water (55° F.) cleaning performance of a laundry detergent formula comprising a concentrated blend of anionic and nonionic surfactants, a builder, $C_{16}$ MES, and an experimental sample. The formulations are prepared as described below. The experimental sample is tested for its ability to improve the overall cleaning performance relative to cocamide DEA.

Preparation of Concentrated Blend:

Deionized water (90% of the required total amount) is first combined and mixed at 50° C. with Bio-Soft® S-101 (dodecylbenzene sulfonic acid, 3.27 wt. %, product of Stepan). Sodium hydroxide (50% aq. solution) is added to pH 11 (about 24% of the total amount of 4 wt. % required). Citric acid (50% aq. solution, 6.2 wt. %) is added, followed by triethanolamine (3.45 wt. %). Bio-Soft® EC-690 (laureth-7, 90% actives, 27.8 wt. %, product of Stepan) is slowly added. The pH is adjusted to the 7.8 to 8.4 range, targeting 8.1 with the remaining aqueous sodium hydroxide solution. Sodium xylene sulfonate (40% actives, 4.30 wt. %) is added, followed by a preservative and the remaining deionized water (q.s. to 100 wt. %).

Preparation of an Ultra Laundr Detergent with $C_{16}$ MES and the Blend:

Deionized water (q.s. to 100 wt. %) is charged at 55-60° C. The concentrated blend prepared above (58.0 wt. %) is added while maintaining temperature between 50° C. and 60° C. The $C_{16}$ MES (87% actives, 10.34 wt. %) is slowly added and allowed to dissolve. The mixture is then allowed to cool to 35° C. The experimental sample or cocamide DEA standard (5.0 wt. %) is then added slowly and mixing continues until the batch is homogeneous.

Cold-Water Cleaning Evaluation:

Laundry detergent (30 g, see Part A) is charged to the laundry machine, followed by soiled/stained fabric swatches that are attached to pillowcases. Wash temperature: 55° F. Rinse: 55° F. The swatches are detached from pillowcases, dried, and ironed. Swatches are scanned to measure the L*a*b* values, which are used to calculate a soil removal index (SRI) for each type of swatch. Finally, the ΔSRI is calculated, which equals the experimental sample SRI minus the SRI of a pre-determined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The following standard soiled/stained fabric swatches are used: dust sebum on cotton (DSC); beef tallow (BT); kaolin clay and wool fat on polyester (WFK 30C), grass on cotton (GC); blueberry on cotton (BC); cocoa on cotton (EMPA 112); and blood/ink/milk on cotton (EMPA 116). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L*a*b* values to calculate the SRI for every type of swatch, and the stain removal index (SRI) is calculated as follows:

$$SRI = 100 - \sqrt{(L^*_{clean} - L^*_{washed})^2 + (a^*_{clean} - a^*_{washed})^2 + (b^*_{clean} - b^*_{washed})^2}$$

$$\Delta SRI = SRI_{sample} - SRI_{standard}$$

As shown in Table 10, two of the test samples perform as well or better than cocamide DEA when evaluated for cold-water cleaning performance.

TABLE 10

Performance in Cold-Water Cleaning:
|ΔSRI| Values v. Cocamide DEA in a $C_{16}$
Methyl Ester Sulfonate (MES) Formulation

| | ΔSRI values | |
|---|---|---|
| test sample | C10-41 | UTG-11 |
| dust sebum on cotton (DSC) | −0.7 | −0.8 |
| beef tallow (BT) | 2.4 | 3.7 |
| pigment/lanolin (WFK 30C) | −0.2 | −1.7 |
| grass on cotton (GC) | −0.7 | −1.2 |
| blueberry on cotton (BC) | 1.7 | 0.7 |
| cocoa on cotton (EMPA 112) | 1.2 | −0.3 |
| blood/ink/milk on cotton (EMPA 116) | 0.3 | −0.4 |
| overall rating | superior | good |

Booster for Bargain Laundry Detergent

This method evaluates the cleaning boosting ability of an experimental sample when used as an additive in a bargain laundry detergent formulation that contains neutralized dodecylbenzene sulfonic acid, a non-ionic surfactant such as an ethoxylated synthetic $C_{12}$-$C_{15}$ alcohol (7 EO), citric acid, monoethanolamine, triethanolamine, and a preservative. The experimental sample is tested for its ability to improve the overall cleaning performance at 1% solids level relative to Ammonyx® LO (lauramine oxide, Stepan, standard booster). Laundry detergent formula (46 g) is charged to the laundry machine, followed by soiled/stained fabric swatches that are attached to pillowcases. Wash temperature: 90° F. Rinse: 70° F. The swatches are detached from pillowcases, dried, and ironed.

The bargain laundry detergent with booster is prepared from sodium hydroxide-neutralized dodecylbenzene sulfonic acid (NaLAS, Bio-Soft® S-101, Stepan, 33.9% actives, 41.3 wt. %), Bio-Soft® N25-7 (fatty alcohol ethoxylate, product of Stepan, 5.00 wt. %), booster (either the experimental sample or Ammonyx LO, which is 30% actives, 3.33 wt. %, citric acid (50% aq. solution, 1.00 wt. %), monoethanolamine (1.00 wt. %), triethanolamine (1.00 wt. %), and deionized water plus preservative (balance to 100 wt. %).

The formulation is made by charging 90% of the total amount of water at 50° C., then adding in order, with mixing, citric acid solution, monoethanolamine, triethanolamine, neutralized sulfonic acid, Bio-Soft N25-7, and booster. The pH is adjusted to 9.5 with 25% aq. NaOH solution, and then preservative and the balance of the water are added.

The following standard soiled/stained fabric swatches are used: dust sebum on cotton (DSC); dust sebum on cotton/polyester (DSCP); beef tallow (BT); clay on cotton (CC); clay on cotton/polyester (CCP); grass on cotton (GC); red wine on cotton (RWC); blueberry on cotton (BC); coffee on cotton (COFC); cocoa on cotton (EMPA 112); blood/ink/milk on cotton (EMPA 116); and make-up on cotton (EMPA 143). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L*a*b* values to calculate the SRI for every type of swatch, and the stain removal index (SRI) is calculated as described in the cold-water cleaning procedure discussed above.

As shown in Table 11, one test sample performs as well as the lauramine oxide control when evaluated as a booster for bargain laundry detergents.

TABLE 11

Performance as a Booster for a Bargain Detergent Formulation:
|ΔSRI| Values versus Ammonyx LO (Lauramine Oxide)

| test sample | ΔSRI values PMTG-11 |
|---|---|
| dust sebum on cotton (DSC) | 0.6 |
| dust sebum on cotton/polyester (DSCP) | 0.9 |
| beef tallow (BT) | −0.7 |
| clay on cotton (CC) | −0.2 |
| clay on cotton/polyester (CCP) | −0.5 |
| grass on cotton (GC) | −0.7 |
| red wine on cotton (RWC) | −0.2 |
| blueberry on cotton (BC) | −0.9 |
| coffee on cotton (COFC) | −0.7 |
| cocoa on cotton (EMPA 112) | 0.5 |
| blood/ink/milk on cotton (EMPA 116) | 0.1 |
| make-up on cotton (EMPA 143) | 0.1 |
| overall rating | good |

Gas Well Foamers: Batch Dynamic Test

In this procedure, test surfactant, brine, and/or condensate are added to a column and then agitated with nitrogen to produce foam. The wt. % of foam carried over the column after 5 min. is a measure of the test sample's performance. Results are collected as a function of brine composition, concentration of surfactant, and percent condensate present in the solution.

Brines are prepared at 12.5% and 25% total dissolved solids (TDS). The brines are an 80:20 ratio of NaCl to $CaCl_2$. The density of the 12.5% TDS is 1.087 g/mL and the density of the 25% TDS is 1.184 g/mL. Brine solutions are filtered to eliminate particulates.

Surfactant samples are tested at 5000, 2000, 1000, and 500 parts per million of actives in each of the brine solutions listed above. A test solution consists of brine, surfactant, and condensate when applicable. The equation below indicates how much surfactant is needed based on actives level and the density of the brine used.

$$\text{Surfactant (g)} = \frac{\left[\frac{\text{desired } ppm}{1000}\right]}{\text{actives}} \times \left[\frac{\text{Total } Sol'n \text{ (g)}}{\text{Density of Brine (g/mL)}}\right] \frac{1}{1000}$$

sure the amount of foam collected. Weight is recorded every second over the course of a 10-minute run. The % of liquid carried over as foam after 5 min. for each brine solution at each % condensate level is reported in Table 12.

As shown in Table 12, eight of the test samples perform as well as or better than the control when evaluated as potential gas well foamers.

TABLE 12

Performance in Gas Well Foamers

| % TDS brine | % Condensate | Conc, ppm | % Carry Over at 5 min. | | | | | | | |
|---|---|---|---|---|---|---|---|---|---|---|
| | | | C10-23 | C10-24 | C10-41 | C10-43 | C12-22 | C12-24 | C12-40 | UTG-11 |
| 12.5 | 0 | 500 | 23 | — | 0 | 7 | 44 | 54 | 46 | 36 |
| 12.5 | 10 | 500 | 15 | 15 | 37 | 32 | 56 | 52 | 70 | 24 |
| 12.5 | 20 | 500 | 12 | 35 | 42 | 30 | 48 | 47 | 61 | 13 |
| 25.0 | 0 | 500 | 45 | — | 0 | 0 | 35 | 44 | 52 | 28 |
| 25.0 | 10 | 500 | 22 | 36 | 49 | 0 | 31 | 46 | 31 | 23 |
| 25.0 | 20 | 500 | 9 | 36 | 46 | 24 | 15 | 37 | 3 | 7 |
| 12.5 | 0 | 1000 | 38 | — | 0 | 30 | 70 | 52 | 64 | 63 |
| 12.5 | 10 | 1000 | 34 | 42 | 48 | 46 | 67 | 68 | 74 | 62 |
| 12.5 | 20 | 1000 | 36 | 51 | 61 | 48 | 51 | 64 | 66 | 51 |
| 25.0 | 0 | 1000 | 46 | — | 0 | 33 | 59 | 53 | 60 | 40 |
| 25.0 | 10 | 1000 | 34 | 39 | 58 | 0 | 50 | 55 | 53 | 46 |
| 25.0 | 20 | 1000 | 33 | 33 | 48 | 43 | 37 | 42 | 39 | 27 |
| 12.5 | 0 | 2000 | 54 | — | 71 | 56 | 87 | 74 | 84 | 70 |
| 12.5 | 10 | 2000 | 52 | 57 | 55 | 60 | 80 | 77 | 76 | 69 |
| 12.5 | 20 | 2000 | 52 | 68 | 68 | 55 | 69 | 66 | 75 | 61 |
| 25.0 | 0 | 2000 | 54 | — | 52 | 67 | 72 | 62 | 82 | 62 |
| 25.0 | 10 | 2000 | 54 | 44 | 69 | 0 | 58 | 64 | 60 | 57 |
| 25.0 | 20 | 2000 | 56 | 24 | 60 | 59 | 47 | 56 | 44 | 39 |
| 12.5 | 0 | 5000 | 78 | — | 92 | 70 | 93 | 92 | 99 | 80 |
| 12.5 | 10 | 5000 | 73 | 91 | 90 | 85 | 76 | 82 | 84 | 69 |
| 12.5 | 20 | 5000 | 75 | 93 | 90 | 76 | 76 | 76 | 80 | 60 |
| 25.0 | 0 | 5000 | 79 | — | 78 | 73 | 80 | 87 | 90 | 67 |
| 25.0 | 10 | 5000 | 74 | 75 | 78 | 50 | 61 | 70 | 72 | 52 |
| 25.0 | 20 | 5000 | 64 | 42 | 72 | 70 | 53 | 64 | 61 | 41 |
| Rating | | | good | superior | good | good | superior | superior | superior | good |

This sample calculation shows how much of a 45% active surfactant is needed to make a 5000 ppm solution in 12.5% TDS brine:

$$\frac{\left[\frac{5000 \, ppm}{1000}\right]}{0.45 \text{ actives}} \times \frac{\left[\frac{238.053 \text{ g}}{1.087 \text{ g/mL}}\right]}{1000} =$$

2.43 g of Surfactant into 238.053 g of 12.5% *TDS* brine

The 5000 ppm solution is used to make a 2000 ppm solution, which is diluted to make a 1000 ppm solution, and so on. When condensate is included, the desired active level in the brine should be such that the active level in the total test solution remains constant with the varying amounts of condensate present. For example, when making a 5000 ppm solution with 10% condensate, the brine/surfactant solution will actually be 5556 ppm so that the solution plus condensate will be ~5000 ppm. When testing how well a product handles condensate, either 10% or 20% is added to a solution. This is done for both brine solutions at every concentration level.

The condensate used is a low-aromatic mineral spirit, Exxsol® D-40 (d=0.7636 g/mL), product of ExxonMobil. The desired amount of condensate is added to the column after the brine/surfactant solution is added. Nitrogen is fed through a glass frit in the bottom of the column and a mass-flow controller is used to feed 14 standard cubic feet per hour. DataStudio (from Pasco) software and a balance are used to mea- Personal Care: Cleansing Application Viscosity and mechanical shake foam tests are used to assess the likely value of a particular surfactant as a secondary surfactant in cleansing applications for personal care.

All experimental samples are evaluated for their performance versus a control (either cocamidopropylhydroxysultaine or cocamidopropylbetaine).

Viscosity curves are generated by preparing dilute aqueous solutions of the test material or control (3% active content) with 12% active sodium lauryl ether (1) sulfate (SLES-1), then measuring viscosity by means of a Brookfield DV-1+ viscometer. Sodium chloride is added incrementally (1-3 wt. %) and viscosity is recorded as a function of increasing NaCl concentration. A "good" result is a curve that shows a viscosity build comparable to the control sample. A "superior" rating indicates that the sample builds viscosity substantially more rapidly than the control.

Foaming properties are evaluated using a mechanical shake foam test. Sample solutions (calculated at 0.2% total surfactant active material) are thereafter made from aqueous solutions using 25° C. tap water. A 100.0-g portion of the solution is carefully transferred to a 500-mL graduated cylinder. Castor oil (2.0 g) is added. The cylinder is stoppered and mechanically inverted ten times, then allowed to settle for 15 s. Foam height is recorded. After 5 min., foam height is recorded again. The experiment is repeated without the castor oil. In one set of experiments, the cleansing base contains SLES-1 in both the experimental and control runs. In a second set of experiments, the cleansing base contains another widely used anionic surfactant, i.e., a mixture of sodium methyl 2-sulfolaurate and disodium 2-sulfolaurate, instead of SLES-1. A "good" result is recorded when the solution containing the test material results in foam heights that are within +/−25 mL of the control runs. Results >25 mL of the control garner a superior rating; results <25 mL of the control are rated inferior.

Ten test materials, identified in Table 13 show good overall performance in the viscosity and foam tests.

TABLE 13

Personal Care/Secondary Cleaner Viscosity and Shake Foam Test Results

| Sample | Viscosity Build | Foam Tests | Sample | Viscosity Build | Foam Tests |
|---|---|---|---|---|---|
| C10-24 | good[1] | good[1] | PMTG-6 | good[3] | good[2] |
| C12-24 | good[1] | good[1] | PMTG-13 | good[2] | good[2] |
| C12-40 | good[2] | good[2] | PUTG-6 | good[2] | good[2] |
| C16-13 | good[2] | inferior[2] | PUTG-11 | good[1] | good[1] |
| MTG-6 | good[3] | good[2] | MTG-14 | good[2] | good[2] |

[1]Control = cocamidopropyl hydroxysultaine;
[2]Control = cocamidopropyl betaine
[3]Control = cocamide MEA Personal Care/Antibacterial Handsoap:
Method to Determine Foam Enhancement Benefit Foam volume, which signals "clean" to consumers, is a desirable attribute in an antibacterial handsoap. Because cationic antibacterial actives are not compatible with anionic surfactants (the best foamers), achieving sufficient foam volume with them is challenging. The method below identifies surfactants that provide more foam volume than cocamidopropylbetaine (actives/actives basis) in an antibacterial handsoap base. Formulation: deionized water (q.s. to 100 wt. %), cocoglucoside (3.0 wt. %), lauramine oxide (3.0 wt. %), benzalkonium chloride (0.1 wt. %), and test molecule or cocamidopropylbetaine (3.0 wt. %).

Solutions are prepared by combining ingredients in the order prescribed above, stirring with a stir bar or mixing gently using an overhead stirrer or manually using a spatula. Heat may be applied if the test molecule is a solid at room temperature. Mixing is maintained to ensure a homogenous solution. The pH is adjusted to 6.5+/−0.5.

Test and control solutions are compared, with and without 2% castor oil, at 0.2% total surfactant active concentration (2.22 g solution to 100 mL with tap water from Lake Michigan, ~150 ppm Ca/Mg hardness) for foam volume using the cylinder inversion test. Initial and delayed (5 min.) measurements are taken.

Rating system: Superior: a result >25 mL over the cocamidopropylbetaine control in both oil and no-oil systems. Good: a result within 25 mL of the cocamidopropylbetaine control in both oil and no-oil systems. Inferior: a result >25 mL below that of the cocamidopropylbetaine control in both oil and no-oil systems.

Compared with the controls, the four test materials identified in Table 14 all show superior overall performance in the antibacterial handsoap tests:

TABLE 14

Superior Performance in Antibacterial Handsoap

| MTG-13 | PMTG-13 | UTG-13 | PUTG-13 |

Compared with the controls, the seventeen test materials identified in Table 15 all show good overall performance in the antibacterial handsoap tests:

TABLE 15

Good Performance in Antibacterial Handsoap

| C10-22 | C12-41 | C18-36 |
| C10-24 | C16-10 | Mix-65 |
| C12-19 | C18-32 | MTG-6 |
| C12-22 | C18-34 | UTG-6 |
| C12-24 | Mix-34 | UTG-14 |
| C12-40 | Mix-35 | |

Hair Conditioners: Procedure for Evaluation of Wet Compatibility

Hair tresses (10" lengths, 2-3 g) are prepared using a consistent and uniform hair type (double-bleached, blond). The tresses are collectively shampooed with a 15% active sodium lauryl sulfate solution. Care is taken to avoid excessive tangling during shampooing. The tresses are rinsed clean with 40° C. tap water. The process is repeated to simulate a double shampoo application. The tresses are separated and tagged for testing. A test conditioner preparation (2.0 cm$^3$) is applied to each clean, wet tress using a syringe. The base conditioner contains cetyl alcohol (2.0%), hydroxyethyl cellulose (0.7%), cetrimonium chloride (1.0%), and water (qs to 100%). Test samples are formulated as a 2 wt. % (actives) additive to the base conditioner.

The conditioner is worked through the hair for one minute with downward finger strokes. The tresses are rinsed thoroughly clean under 40° C. tap water. Excess water is squeezed from each tress to simulate towel-dry hair. The hair is combed through, at first, in the wet state. Ease of combing is evaluated for the test samples and the base conditioner, and qualitative ratings are assigned to the test samples in comparison to the results with base conditioner only.

For the quaternized compositions tested, the rating system is as follows: "superior" is an improvement of wet combing above that of the conditioner used as a control for testing; "equal" is wet combing comparable to the conditioner used as a control for testing; and "inferior" is wet combing worse than the conditioner used as a control for testing.

One sample, Mix-44, is superior to the base conditioner in this test, and two samples, C16-10 and PUTG-13, perform equal to the control.

Oilfield Corrosion Inhibition: Polarization Resistance Procedure

Polarization resistance is run in dilute NACE brine (3.5 wt. % NaCl; 0.111 wt. % $CaCl_2.2H_2O$; 0.068 wt. % $MgCl_2.6H_2O$) under sweet conditions ($CO_2$ sparged) at 50° C. The working electrode is cylindrical, made of C1018 steel, and rotates at 3000 rpm. The counter electrode is a platinum wire. The reference is a calomel electrode with an internal salt bridge. A baseline corrosion rate is established over at least a 3-h period. Once the baseline has been established, the corrosion inhibitor is injected and data is collected for the remainder of the test period. The desired inhibitor concentration is 0.00011-0.0010 meq/g active. Software details: initial delay is on at 1800 s with 0.05 mV/s stability; range: −0.02 to +0.02V; scan rate: 0.1 mV/s; sample perioerd: 1 s; data collection: ~24 h. The final corrosion rate is an average of the last 5-6 h of data collection. Protection rate is calculated from:

$$\text{Protection Rate} = \frac{\left(\text{Initial Protection Rate [no inhibitor]} - \text{Final Protection Rate [with inhibitor]}\right) * 100}{\text{Initial Protection Rate [no inhibitor]}}$$

As shown in Table 16, eight of the tested samples show overall performance as corrosion inhibitors that equals or exceeds that of the control.

TABLE 16

Performance in EOR Corrosion Inhibitors

| Sample | Protection Rate (%) | | | Overall Rating |
|---|---|---|---|---|
| | Low Dose | Mid Dose | High Dose | |
| Industry Std. A | 85 | 85 | 80 | |
| Control B | 66 | 83 | 76 | |
| Control C | 97 | 98 | 97 | |
| Control D | 90 | 98 | 85 | |
| MTG-14 | 97 | 98 | 96 | superior |
| UTG-14 | 97 | 95 | 95 | superior |
| C16-13 | 91 | 85 | 80 | good |
| Mix-36 | 3 | 57 | 98 | good |
| PMTG-6 | 4 | 87 | 85 | good |
| UTG-6 | 98 | 95 | 92 | good |
| PUTG-6 | 92 | 92 | 84 | good |
| PUTG-14 | 71 | 88 | 92 | good |

Oil Field Products: Paraffin Dispersants
Asphaltenes Screening Test

During acid stimulation of an oil well, a blend of HCl, HF, and corrosion inhibitor is pumped down a well, allowed to stand, and then pumped out. During the transfer of the acid, small amounts of iron chloride are developed in the acid solution. Once the acid blend dissolves scales and deposits in the well bore, crude oil begins to flow and mixes with the acid solution in the well. The crude oil can solidify after acidizing, and asphaltenes have been associated with the problem. Thus, dispersants are commonly added to the acid to prevent the solidification.

Test Method:

A stock solution of iron-contaminated acid is made by adding 1% $FeCl_3$ to a 15% HCl acid solution. The sample dispersant to be tested (0.2 wt. %) is added to the acid stock solution (7.5 mL). A 15-mL vial is charged with the acid/dispersant mixture and crude oil (2.5 mL), and the vial is shaken vigorously for 30 s. The initial appearance is recorded. After standing at room temperature for 1 h, the appearance is again noted. The vial is placed in an oven (50° C.) for 24 h and its appearance is recorded. The vial is allowed to cool to room temperature and appearance is again noted. Finally, after 24 h at room temperature, appearance is again noted. A blank sample containing crude oil and acid solution but no dispersant is run. A control sample containing soy amidoamine trimethylammonium chloride as the dispersant is also run. Yet another sample is run containing a 1:1 mixture of test dispersant and soy amidoamine trimethylammonium chloride.

One sample, C18-65, provides performance that is equal to the control in this test, while C18-27 demonstrates superior performance.

Performance as a Foamer or Foam Additive for Specialty Foamer Applications

Specialty foamer applications include (among others) gypsum, concrete, and fire-fighting foams. The tests below evaluate foam stability when the sample is used as the primary foamer and also evaluate the sample's performance as an additive when used as a foam stabilizer, enhancer, or destabilizer.

Particularly for gypsum, for which set-up times are rapid on commercial production lines, a desirable foam additive helps to control the coalescence of the bubble to provide a larger bubble within a prescribed time frame. Preferably, destabilization of the foam occurs at the end of the first minute in the tests below. These compositions are identified as "good" performers as gypsum foam destabilizers in Table 17 because they allow this balance to be struck effectively.

Foam Stability: Drainage Method

Surfactant solutions (0.4 wt. % active material) are prepared by mixing surfactant with waters having varying hardnesses (342 ppm hard water or 1000 ppm $CaSO_4$ water). Surfactant solution (100 mL) is carefully transferred to a stainless-steel mixing cup, then mixed at high speed (27K rpm) using a Hamilton Beach mixer for 10 s. The contents are quickly poured into a 100-mL graduated cylinder to the 100-mL mark, and a stopwatch is immediately started. The amount of liquid settling in the cylinder is recorded every 15 s for 4 min. Less liquid drained indicates greater foam stability.

Foam Stability: Foam Half Life

A sample of surfactant solution prepared as described above (100 g) is mixed at high speed for 30 s. The mixture is quickly poured into a 1000-mL graduated cylinder and a stopwatch is immediately started. Initial foam height is recorded. When 50 mL of liquid appears in the cylinder, the time and foam height are recorded as the foam half life (in seconds) and foam height at half life (in mL), respectively.

TABLE 17

Good Performance as a Foam Destabilizer for Gypsum Applications

| C10-22 | C16-10 | UTG-6 |
|---|---|---|
| C12-22 | Mix-44 | |

The preceding examples are meant only as illustrations. The following claims define the invention.

We claim:

1. A quaternary ammonium, betaine, or sulfobetaine composition derived from a fatty amine, wherein the fatty amine is made from a metathesis-derived $C_{10}$-$C_{17}$ monounsaturated acid, octadecene-1,18-dioic acid, or their ester derivatives; and wherein the quaternary ammonium composition has the formula:

$R^2(R^3)N^+(R^1)R^4 X^-$ 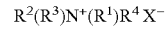

wherein $R^1$ is $-(CH_2)_8-CH=CHR^5$ or $-(CH_2)_8-CH=CH-(CH_2)_8-N^+(R^2)(R^3)R^4 X^-$; each of $R^2$ and $R^3$ is independently substituted or unsubstituted alkyl, aryl, alkenyl, oxyalkylene, or polyoxyalkylene; $R^4$ is $C_1$-$C_6$ alkyl; $X^-$ is a halide, bicarbonate, bisulfate, or alkyl sulfate; and $R^5$ is $C_1$-$C_7$ alkyl; or wherein the betaine or sulfobetaine has the formula:

$R^2(R^3)N^+(R^1)R^4$ 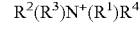

wherein $R^1$ is $-(CH_2)_8-CH=CHR^5$ or $-(CH_2)_8-CH=CH-(CH_2)_8-N^+(R^2)(R^3)R^4$; each of $R^2$ and $R^3$ is independently substituted or unsubstituted alkyl, aryl, alkenyl, oxyalkylene, or polyoxyalkylene; $R^4$ is $C_2$-$C_4$ alkylene carboxylate, $C_2$-$C_4$ alkylene sulfonate, or $C_2$-$C_4$ hydroxyalkylene sulfonate; and $R^5$ is hydrogen or $C_1$-$C_7$ alkyl; and wherein when $R^5$ is $C_1$-$C_7$ alkyl, the quaternary ammonium, betaine, or sulfobetaine composition has at least 1 mole % of trans-$\Delta^9$ unsaturation.

2. A derivative made by sulfonating or sulfitating the composition of claim 1.

3. The composition of claim 1 wherein the fatty amine is made by reacting the metathesis-derived acid or ester derivative with a secondary amine, followed by reduction of the resulting fatty amide.

4. The composition of claim 3 wherein the secondary amine is selected from the group consisting of N,N-dimethylamine, N,N-diethylamine, and N,N-diisopropylamine.

5. The composition of claim 1 wherein the fatty amine is made by reducing the metathesis-derived acid or ester derivative to give a fatty alcohol, followed by amination of the fatty alcohol.

6. The composition of claim 5 wherein the amination is performed in a single step by reacting the fatty alcohol with a secondary amine in the presence of an amination catalyst.

7. The composition of claim 1 wherein the ester derivative is a modified triglyceride made by self-metathesis of a natural oil.

8. The composition of claim 7 wherein the natural oil is selected from the group consisting of soybean oil, palm oil, rapeseed oil, algal oil, and mixtures thereof.

9. The composition of claim 1 wherein the ester derivative is an unsaturated triglyceride made by cross-metathesis of a natural oil with an olefin.

10. The composition of claim 9 wherein the natural oil is selected from the group consisting of soybean oil, palm oil, rapeseed oil, algal oil, and mixtures thereof, and the olefin is a $C_2$-$C_8$ α-olefin or a $C_4$-$C_9$ internal olefin.

11. A water-soluble herbicide composition comprising the quaternary ammonium, betaine, or sulfobetaine composition of claim 1.

12. A water-soluble herbicide composition comprising the derivative of claim 2.

\* \* \* \* \*